US008415517B2

(12) United States Patent
Gadewar et al.

(10) Patent No.: US 8,415,517 B2
(45) Date of Patent: Apr. 9, 2013

(54) CONTINUOUS PROCESS FOR CONVERTING NATURAL GAS TO LIQUID HYDROCARBONS

(75) Inventors: Sagar Gadewar, Goleta, CA (US); Michael Wyrsta, Santa Barbara, CA (US); Philip Grosso, Auburn, CA (US); Aihua Zhang, Santa Barbara, CA (US); Eric W. McFarland, Santa Barbara, CA (US); Zachary J. A. Komon, Cardiff by the Sea, CA (US); Jeffrey H. Sherman, Sebastian, FL (US); Peter Stoimenov, Goleta, CA (US); Hongfei Lin, Madison, WI (US); Shawn Huff, Portland, OR (US); Shouli Sun, Santa Barbara, CA (US)

(73) Assignee: GRT, Inc., Santa Barbara, CA (US)

( * ) Notice: Subject to any disclaimer, the term of this patent is extended or adjusted under 35 U.S.C. 154(b) by 581 days.

(21) Appl. No.: 12/504,865

(22) Filed: Jul. 17, 2009

(65) Prior Publication Data

US 2010/0099929 A1 Apr. 22, 2010

Related U.S. Application Data

(60) Provisional application No. 61/081,976, filed on Jul. 18, 2008, provisional application No. 61/082,000, filed on Jul. 18, 2008, provisional application No. 61/082,115, filed on Jul. 18, 2008, provisional application No. 61/082,143, filed on Jul. 18, 2008.

(51) Int. Cl.
*C07C 1/00* (2006.01)

(52) U.S. Cl.
USPC .......................................... 585/310; 585/943

(58) Field of Classification Search .................. None
See application file for complete search history.

(56) References Cited

U.S. PATENT DOCUMENTS

| | | | |
|---|---|---|---|
| 2,168,260 A | 8/1939 | Heisel et al. |
| 2,246,082 A | 6/1941 | Vaughan et al. |
| 2,488,083 A | 11/1949 | Gorin et al. |
| 2,677,598 A | 5/1954 | Crummett et al. |
| 2,941,014 A | 6/1960 | Rothweiler et al. |
| 3,076,784 A | 2/1963 | Huermann et al. |
| 3,172,915 A | 3/1965 | Borkowski et al. |
| 3,246,043 A | 4/1966 | Rosset et al. |
| 3,273,964 A | 9/1966 | Rosset |
| 3,294,846 A | 12/1966 | Livak et al. |
| 3,310,380 A | 3/1967 | Lester |
| 3,346,340 A | 10/1967 | Louvar et al. |
| 3,353,916 A | 11/1967 | Lester |
| 3,353,919 A | 11/1967 | Stockman |
| 3,496,242 A | 2/1970 | Berkowitz et al. |
| 3,562,321 A | 2/1971 | Borkowski et al. |
| 3,598,876 A | 8/1971 | Bloch |
| 3,657,367 A | 4/1972 | Blake et al. |
| 3,670,037 A | 6/1972 | Dugan |
| 3,673,264 A | 6/1972 | Kuhn |
| 3,679,758 A | 7/1972 | Schneider |
| 3,702,886 A | 11/1972 | Argauer et al. |
| 3,705,196 A | 12/1972 | Turner |
| 3,799,997 A | 3/1974 | Schmerling |
| 3,865,886 A | 2/1975 | Schindler et al. |
| 3,876,715 A | 4/1975 | McNulty et al. |
| 3,879,473 A | 4/1975 | Stapp |
| 3,879,480 A | 4/1975 | Riegel et al. |
| 3,883,651 A | 5/1975 | Woitun et al. |
| 3,886,287 A | 5/1975 | Kobayashi et al. |
| 3,894,103 A | 7/1975 | Chang et al. |
| 3,894,104 A | 7/1975 | Chang et al. |
| 3,894,105 A | 7/1975 | Chang et al. |
| 3,894,107 A | 7/1975 | Butter et al. |
| 3,894,927 A | 7/1975 | Kane et al. |
| 3,907,917 A | 9/1975 | Forth |
| 3,919,336 A | 11/1975 | Kurtz |
| 3,920,764 A | 11/1975 | Riegel et al. |
| 3,923,913 A | 12/1975 | Antonini et al. |
| 3,928,483 A | 12/1975 | Chang et al. |
| 3,965,205 A | 6/1976 | Garwood et al. |
| 3,974,062 A | 8/1976 | Owen et al. |
| 3,976,447 A | 8/1976 | Merchant et al. |
| 3,987,119 A | 10/1976 | Kurtz et al. |
| 3,992,466 A | 11/1976 | Plank et al. |
| 4,006,169 A | 2/1977 | Anderson et al. |
| 4,011,278 A | 3/1977 | Plank et al. |
| 4,025,571 A | 5/1977 | Lago |
| 4,025,572 A | 5/1977 | Lago |
| 4,025,575 A | 5/1977 | Chang et al. |
| 4,025,576 A | 5/1977 | Chang et al. |
| 4,035,285 A | 7/1977 | Owen et al. |
| 4,035,430 A | 7/1977 | Dwyer et al. |
| 4,039,600 A | 8/1977 | Chang |
| 4,044,061 A | 8/1977 | Chang et al. |
| 4,046,825 A | 9/1977 | Owen et al. |
| 4,049,734 A | 9/1977 | Garwood et al. |
| 4,052,471 A | 10/1977 | Pearsall |
| 4,052,472 A | 10/1977 | Given et al. |
| 4,058,576 A | 11/1977 | Chang et al. |

(Continued)

FOREIGN PATENT DOCUMENTS

| | | |
|---|---|---|
| BR | 0210054 | 8/2004 |
| CA | 1099656 | 4/1981 |

(Continued)

OTHER PUBLICATIONS

U.S. Appl. No. 60/487,364, filed Jul. 15, 2003, Lorkovic et al.

(Continued)

*Primary Examiner* — Sudhakar Katakam

(74) *Attorney, Agent, or Firm* — Adolph Locklar

(57) ABSTRACT

A method comprising: providing a first halogen stream; providing a first alkane stream; reacting at least a portion of the first halogen stream with at least a portion of the first alkane stream in a first reaction vessel to form a first halogenated stream; providing a second alkane stream comprising $C_2$ and higher hydrocarbons; providing a second halogen stream; and reacting at least a portion of the second halogen stream with at least a portion of the second alkane stream in a second reaction vessel to form a second halogenated stream.

8 Claims, 30 Drawing Sheets

U.S. PATENT DOCUMENTS

| | | |
|---|---|---|
| 4,060,568 A | 11/1977 | Rodewald |
| 4,071,753 A | 1/1978 | Fulenwider et al. |
| 4,072,733 A | 2/1978 | Hargis et al. |
| 4,087,475 A | 5/1978 | Jordan |
| 4,088,706 A | 5/1978 | Kaeding |
| 4,092,368 A | 5/1978 | Smith |
| 4,110,180 A | 8/1978 | Nidola et al. |
| 4,117,251 A | 9/1978 | Kaufhold et al. |
| 4,129,604 A | 12/1978 | Tsao |
| 4,133,838 A | 1/1979 | Pearson |
| 4,133,966 A | 1/1979 | Pretzer et al. |
| 4,138,440 A | 2/1979 | Chang et al. |
| 4,156,698 A | 5/1979 | Dwyer et al. |
| 4,169,862 A | 10/1979 | Eden |
| 4,172,099 A | 10/1979 | Severino |
| 4,187,255 A | 2/1980 | Dodd |
| 4,194,990 A | 3/1980 | Pieters et al. |
| 4,197,420 A | 4/1980 | Ferraris et al. |
| 4,219,680 A | 8/1980 | Konig et al. |
| 4,249,031 A | 2/1981 | Drent et al. |
| 4,270,929 A | 6/1981 | Dang Vu et al. |
| 4,272,338 A | 6/1981 | Lynch et al. |
| 4,282,159 A | 8/1981 | Davidson et al. |
| 4,300,005 A | 11/1981 | Li |
| 4,300,009 A | 11/1981 | Haag et al. |
| 4,301,253 A | 11/1981 | Warren |
| 4,302,619 A | 11/1981 | Gross et al. |
| 4,307,261 A | 12/1981 | Beard, Jr. et al. |
| 4,308,403 A | 12/1981 | Knifton |
| 4,311,865 A | 1/1982 | Chen et al. |
| 4,317,800 A | 3/1982 | Sloterdijk et al. |
| 4,317,934 A | 3/1982 | Seemuth |
| 4,317,943 A | 3/1982 | Knifton |
| 4,320,241 A | 3/1982 | Frankiewicz |
| 4,333,852 A | 6/1982 | Warren |
| 4,347,391 A | 8/1982 | Campbell |
| 4,350,511 A | 9/1982 | Holmes et al. |
| 4,371,716 A | 2/1983 | Paxson et al. |
| 4,373,109 A | 2/1983 | Olah |
| 4,376,019 A | 3/1983 | Gamlen et al. |
| 4,380,682 A | 4/1983 | Leitert et al. |
| 4,384,159 A | 5/1983 | Diesen |
| 4,389,391 A | 6/1983 | Dunn |
| 4,410,714 A | 10/1983 | Apanel |
| 4,412,086 A | 10/1983 | Beard, Jr. et al. |
| 4,418,236 A | 11/1983 | Cornelius et al. |
| 4,431,856 A | 2/1984 | Daviduk et al. |
| 4,433,189 A | 2/1984 | Young |
| 4,433,192 A | 2/1984 | Olah |
| 4,439,409 A | 3/1984 | Puppe et al. |
| 4,440,871 A | 4/1984 | Lok et al. |
| 4,443,620 A | 4/1984 | Gelbein et al. |
| 4,462,814 A | 7/1984 | Holmes et al. |
| 4,465,884 A | 8/1984 | Degnan et al. |
| 4,465,893 A | 8/1984 | Olah |
| 4,467,130 A | 8/1984 | Olah |
| 4,467,133 A | 8/1984 | Chang et al. |
| 4,489,210 A | 12/1984 | Judat et al. |
| 4,489,211 A | 12/1984 | Ogura et al. |
| 4,492,657 A | 1/1985 | Heiss |
| 4,496,752 A | 1/1985 | Gelbein et al. |
| 4,497,967 A | 2/1985 | Wan |
| 4,499,314 A | 2/1985 | Seddon et al. |
| 4,506,105 A | 3/1985 | Kaufhold |
| 4,509,955 A | 4/1985 | Hayashi |
| 4,513,092 A | 4/1985 | Chu et al. |
| 4,513,164 A | 4/1985 | Olah |
| 4,523,040 A | 6/1985 | Olah |
| 4,524,227 A | 6/1985 | Fowles et al. |
| 4,524,228 A | 6/1985 | Fowles et al. |
| 4,524,231 A | 6/1985 | Fowles et al. |
| 4,538,014 A | 8/1985 | Miale et al. |
| 4,538,015 A | 8/1985 | Miale et al. |
| 4,540,826 A | 9/1985 | Banasiak et al. |
| 4,543,434 A | 9/1985 | Chang |
| 4,544,781 A | 10/1985 | Chao et al. |
| 4,547,612 A | 10/1985 | Tabak |
| 4,550,217 A | 10/1985 | Graziani et al. |
| 4,550,218 A | 10/1985 | Chu |
| 4,568,660 A | 2/1986 | Klosiewicz |
| 4,579,977 A | 4/1986 | Drake |
| 4,579,992 A | 4/1986 | Kaufhold et al. |
| 4,579,996 A | 4/1986 | Font Freide et al. |
| 4,587,375 A | 5/1986 | Debras et al. |
| 4,588,835 A | 5/1986 | Torii et al. |
| 4,590,310 A | 5/1986 | Townsend et al. |
| 4,599,474 A | 7/1986 | Devries et al. |
| 4,605,796 A | 8/1986 | Isogai et al. |
| 4,605,803 A | 8/1986 | Chang et al. |
| 4,621,161 A | 11/1986 | Shihabi |
| 4,621,164 A | 11/1986 | Chang et al. |
| 4,633,027 A | 12/1986 | Owen et al. |
| 4,634,800 A | 1/1987 | Withers, Jr. et al. |
| 4,642,403 A | 2/1987 | Hyde et al. |
| 4,642,404 A | 2/1987 | Shihabi |
| 4,652,688 A | 3/1987 | Brophy et al. |
| 4,654,449 A | 3/1987 | Chang et al. |
| 4,655,893 A | 4/1987 | Beale |
| 4,658,073 A | 4/1987 | Tabak |
| 4,658,077 A | 4/1987 | Kolts et al. |
| 4,665,259 A | 5/1987 | Brazdil et al. |
| 4,665,267 A | 5/1987 | Barri |
| 4,665,270 A | 5/1987 | Brophy et al. |
| 4,675,410 A | 6/1987 | Feitler et al. |
| 4,690,903 A | 9/1987 | Chen et al. |
| 4,695,663 A | 9/1987 | Hall et al. |
| 4,696,985 A | 9/1987 | Martin |
| 4,704,488 A | 11/1987 | Devries et al. |
| 4,704,493 A | 11/1987 | Devries et al. |
| 4,709,108 A | 11/1987 | Devries et al. |
| 4,720,600 A | 1/1988 | Beech, Jr. et al. |
| 4,720,602 A | 1/1988 | Chu |
| 4,724,275 A | 2/1988 | Hinnenkamp et al. |
| 4,735,747 A | 4/1988 | Ollivier et al. |
| 4,737,594 A | 4/1988 | Olah |
| 4,748,013 A | 5/1988 | Saito et al. |
| 4,769,504 A | 9/1988 | Noceti et al. |
| 4,774,216 A | 9/1988 | Kolts et al. |
| 4,775,462 A | 10/1988 | Imai et al. |
| 4,777,321 A | 10/1988 | Harandi et al. |
| 4,781,733 A | 11/1988 | Babcock et al. |
| 4,783,566 A | 11/1988 | Kocal et al. |
| 4,788,369 A | 11/1988 | Marsh et al. |
| 4,788,377 A | 11/1988 | Chang et al. |
| 4,792,642 A | 12/1988 | Rule et al. |
| 4,795,732 A | 1/1989 | Barri |
| 4,795,737 A | 1/1989 | Rule et al. |
| 4,795,843 A | 1/1989 | Imai et al. |
| 4,795,848 A | 1/1989 | Teller et al. |
| 4,804,797 A | 2/1989 | Minet et al. |
| 4,804,800 A | 2/1989 | Bortinger et al. |
| 4,808,763 A | 2/1989 | Shum |
| 4,814,527 A | 3/1989 | Diesen |
| 4,814,532 A | 3/1989 | Yoshida et al. |
| 4,814,535 A | 3/1989 | Yurchak |
| 4,814,536 A | 3/1989 | Yurchak |
| 4,849,562 A | 7/1989 | Buhs et al. |
| 4,849,573 A | 7/1989 | Kaeding |
| 4,851,602 A | 7/1989 | Harandi et al. |
| 4,851,606 A | 7/1989 | Ragonese et al. |
| 4,886,925 A | 12/1989 | Harandi |
| 4,886,932 A | 12/1989 | Leyshon |
| 4,891,463 A | 1/1990 | Chu |
| 4,895,995 A | 1/1990 | James, Jr. et al. |
| 4,899,000 A | 2/1990 | Stauffer |
| 4,899,001 A | 2/1990 | Kalnes et al. |
| 4,899,002 A | 2/1990 | Harandi et al. |
| 4,902,842 A | 2/1990 | Kalnes et al. |
| 4,925,995 A | 5/1990 | Robschlager |
| 4,929,781 A | 5/1990 | James, Jr. et al. |
| 4,939,310 A | 7/1990 | Wade |
| 4,939,311 A | 7/1990 | Washecheck et al. |
| 4,945,175 A | 7/1990 | Hobbs et al. |
| 4,950,811 A | 8/1990 | Doussain et al. |
| 4,950,822 A | 8/1990 | Dileo et al. |
| 4,956,521 A | 9/1990 | Volles |
| 4,962,252 A | 10/1990 | Wade |

| | | | | | |
|---|---|---|---|---|---|
| 4,973,776 A | 11/1990 | Allenger et al. | 5,319,132 A | 6/1994 | Ozawa et al. |
| 4,973,786 A | 11/1990 | Karra | 5,334,777 A | 8/1994 | Miller et al. |
| 4,982,024 A | 1/1991 | Lin et al. | 5,345,021 A | 9/1994 | Casci et al. |
| 4,982,041 A | 1/1991 | Campbell | 5,354,916 A | 10/1994 | Horvath et al. |
| 4,988,660 A | 1/1991 | Campbell | 5,354,931 A | 10/1994 | Jan et al. |
| 4,990,696 A | 2/1991 | Stauffer | 5,366,949 A | 11/1994 | Schubert |
| 4,990,711 A | 2/1991 | Chen et al. | 5,371,313 A | 12/1994 | Ostrowicki |
| 5,001,293 A | 3/1991 | Nubel et al. | 5,382,704 A | 1/1995 | Krespan et al. |
| 5,004,847 A | 4/1991 | Beaver et al. | 5,382,743 A | 1/1995 | Beech, Jr. et al. |
| 5,013,424 A | 5/1991 | James, Jr. et al. | 5,382,744 A | 1/1995 | Abbott et al. |
| 5,013,793 A | 5/1991 | Wang et al. | 5,385,718 A | 1/1995 | Casci et al. |
| 5,019,652 A | 5/1991 | Taylor et al. | 5,395,981 A | 3/1995 | Marker |
| 5,026,934 A | 6/1991 | Bains et al. | 5,399,258 A | 3/1995 | Fletcher et al. |
| 5,026,937 A | 6/1991 | Bricker | 5,401,890 A | 3/1995 | Parks |
| 5,026,944 A | 6/1991 | Allenger et al. | 5,401,894 A | 3/1995 | Brasier et al. |
| 5,034,566 A | 7/1991 | Ishino et al. | 5,406,017 A | 4/1995 | Withers, Jr. |
| 5,043,502 A | 8/1991 | Martindale et al. | 5,414,173 A | 5/1995 | Garces et al. |
| 5,055,235 A | 10/1991 | Brackenridge et al. | 5,430,210 A | 7/1995 | Grasselli et al. |
| 5,055,633 A | 10/1991 | Volles | 5,430,214 A | 7/1995 | Smith et al. |
| 5,055,634 A | 10/1991 | Volles | 5,430,219 A | 7/1995 | Sanfilippo et al. |
| 5,059,744 A | 10/1991 | Harandi et al. | 5,436,378 A | 7/1995 | Masini et al. |
| 5,068,478 A | 11/1991 | Miller et al. | 5,444,168 A | 8/1995 | Brown |
| 5,071,449 A | 12/1991 | Sircar | 5,446,234 A | 8/1995 | Casci et al. |
| 5,071,815 A | 12/1991 | Wallace | 5,453,557 A | 9/1995 | Harley et al. |
| 5,073,656 A | 12/1991 | Chafin et al. | 5,456,822 A | 10/1995 | Marcilly et al. |
| 5,073,657 A | 12/1991 | Warren | 5,457,255 A | 10/1995 | Kumata et al. |
| 5,082,473 A | 1/1992 | Keefer | 5,464,799 A | 11/1995 | Casci et al. |
| 5,082,816 A | 1/1992 | Teller et al. | 5,465,699 A | 11/1995 | Voigt |
| 5,085,674 A | 2/1992 | Leavitt | 5,470,377 A | 11/1995 | Whitlock |
| 5,087,779 A | 2/1992 | Nubel et al. | 5,480,629 A | 1/1996 | Thompson et al. |
| 5,087,786 A | 2/1992 | Nubel et al. | 5,486,627 A | 1/1996 | Quarderer et al. |
| 5,087,787 A | 2/1992 | Kimble et al. | 5,489,719 A | 2/1996 | Le et al. |
| 5,093,542 A | 3/1992 | Gaffney | 5,489,727 A | 2/1996 | Randolph et al. |
| 5,096,469 A | 3/1992 | Keefer | 5,500,297 A | 3/1996 | Thompson et al. |
| 5,097,083 A | 3/1992 | Stauffer | 5,510,525 A | 4/1996 | Sen et al. |
| 5,099,084 A | 3/1992 | Stauffer | 5,523,503 A | 6/1996 | Funk et al. |
| 5,105,045 A | 4/1992 | Kimble et al. | 5,525,230 A | 6/1996 | Wrigley et al. |
| 5,105,046 A | 4/1992 | Washecheck | 5,538,540 A | 7/1996 | Whitlock |
| 5,107,032 A | 4/1992 | Erb et al. | 5,563,313 A | 10/1996 | Chung et al. |
| 5,107,051 A | 4/1992 | Pannell | 5,565,092 A | 10/1996 | Pannell et al. |
| 5,107,061 A | 4/1992 | Ou et al. | 5,565,616 A | 10/1996 | Li et al. |
| 5,108,579 A | 4/1992 | Casci | 5,571,762 A | 11/1996 | Clerici et al. |
| 5,118,899 A | 6/1992 | Kimble et al. | 5,571,885 A | 11/1996 | Chung et al. |
| 5,120,332 A | 6/1992 | Wells | 5,599,381 A | 2/1997 | Whitlock |
| 5,132,343 A | 7/1992 | Zwecker et al. | 5,600,043 A | 2/1997 | Johnston et al. |
| 5,138,112 A | 8/1992 | Gosling et al. | 5,600,045 A | 2/1997 | Van Der Aalst et al. |
| 5,139,991 A | 8/1992 | Taylor et al. | 5,609,654 A | 3/1997 | Le et al. |
| 5,146,027 A | 9/1992 | Gaffney | 5,633,419 A | 5/1997 | Spencer et al. |
| 5,157,189 A | 10/1992 | Karra | 5,639,930 A | 6/1997 | Penick |
| 5,160,502 A | 11/1992 | Kimble et al. | 5,653,956 A | 8/1997 | Zones |
| 5,166,452 A | 11/1992 | Gradl et al. | 5,656,149 A | 8/1997 | Zones et al. |
| 5,175,382 A | 12/1992 | Hebgen et al. | 5,661,097 A | 8/1997 | Spencer et al. |
| 5,178,748 A | 1/1993 | Casci et al. | 5,663,465 A | 9/1997 | Clegg et al. |
| 5,185,479 A | 2/1993 | Stauffer | 5,663,474 A | 9/1997 | Pham et al. |
| 5,188,725 A | 2/1993 | Harandi | 5,675,046 A | 10/1997 | Ohno et al. |
| 5,191,142 A | 3/1993 | Marshall et al. | 5,675,052 A | 10/1997 | Menon et al. |
| 5,194,244 A | 3/1993 | Brownscombe et al. | 5,679,134 A | 10/1997 | Brugerolle et al. |
| 5,202,506 A | 4/1993 | Kirchner et al. | 5,679,879 A | 10/1997 | Mercier et al. |
| 5,202,511 A | 4/1993 | Salinas, III et al. | 5,684,213 A | 11/1997 | Nemphos et al. |
| 5,210,357 A | 5/1993 | Kolts et al. | 5,693,191 A | 12/1997 | Pividal et al. |
| 5,215,648 A | 6/1993 | Zones et al. | 5,695,890 A | 12/1997 | Thompson et al. |
| 5,223,471 A | 6/1993 | Washecheck | 5,698,747 A | 12/1997 | Godwin et al. |
| 5,228,888 A | 7/1993 | Gmelin et al. | 5,705,712 A | 1/1998 | Frey et al. |
| 5,233,113 A | 8/1993 | Periana et al. | 5,705,728 A | 1/1998 | Viswanathan et al. |
| 5,237,115 A | 8/1993 | Makovec et al. | 5,705,729 A | 1/1998 | Huang |
| 5,243,098 A | 9/1993 | Miller et al. | 5,708,246 A | 1/1998 | Camaioni et al. |
| 5,243,114 A | 9/1993 | Johnson et al. | 5,720,858 A | 2/1998 | Noceti et al. |
| 5,245,109 A | 9/1993 | Kaminsky et al. | 5,728,897 A | 3/1998 | Buysch et al. |
| 5,254,772 A | 10/1993 | Dukat et al. | 5,728,905 A | 3/1998 | Clegg et al. |
| 5,254,790 A | 10/1993 | Thomas et al. | 5,734,073 A | 3/1998 | Chambers et al. |
| 5,264,635 A | 11/1993 | Le et al. | 5,741,949 A | 4/1998 | Mack |
| 5,268,518 A | 12/1993 | West et al. | 5,744,669 A | 4/1998 | Kalnes et al. |
| 5,276,226 A | 1/1994 | Horvath et al. | 5,750,801 A | 5/1998 | Buysch et al. |
| 5,276,240 A | 1/1994 | Timmons et al. | 5,770,175 A | 6/1998 | Zones |
| 5,276,242 A | 1/1994 | Wu | 5,776,871 A | 7/1998 | Cothran et al. |
| 5,284,990 A | 2/1994 | Peterson et al. | 5,780,703 A | 7/1998 | Chang et al. |
| 5,300,126 A | 4/1994 | Brown et al. | 5,798,314 A | 8/1998 | Spencer et al. |
| 5,306,855 A | 4/1994 | Periana et al. | 5,814,715 A | 9/1998 | Chen et al. |
| 5,316,995 A | 5/1994 | Kaminsky et al. | 5,817,904 A | 10/1998 | Vic et al. |

| | | | |
|---|---|---|---|
| 5,821,394 A | 10/1998 | Schoebrechts et al. |
| 5,847,224 A | 12/1998 | Koga et al. |
| 5,849,978 A | 12/1998 | Benazzi et al. |
| 5,866,735 A | 2/1999 | Cheung et al. |
| 5,895,831 A | 4/1999 | Brasier et al. |
| 5,898,086 A | 4/1999 | Harris |
| 5,905,169 A | 5/1999 | Jacobson |
| 5,906,892 A | 5/1999 | Thompson et al. |
| 5,908,963 A | 6/1999 | Voss et al. |
| 5,952,538 A | 9/1999 | Vaughn et al. |
| 5,959,170 A | 9/1999 | Withers |
| 5,968,236 A | 10/1999 | Bassine |
| 5,969,195 A | 10/1999 | Stabel et al. |
| 5,977,402 A | 11/1999 | Sekiguchi et al. |
| 5,983,476 A | 11/1999 | Eshelman et al. |
| 5,986,158 A | 11/1999 | Van Broekhoven et al. |
| 5,994,604 A | 11/1999 | Reagen et al. |
| 5,998,679 A | 12/1999 | Miller |
| 5,998,686 A | 12/1999 | Clem et al. |
| 6,002,059 A | 12/1999 | Hellring et al. |
| 6,015,867 A | 1/2000 | Fushimi et al. |
| 6,018,088 A | 1/2000 | Olah |
| 6,022,929 A | 2/2000 | Chen et al. |
| 6,034,288 A | 3/2000 | Scott et al. |
| 6,053,007 A | 4/2000 | Victory et al. |
| 6,056,804 A | 5/2000 | Keefer et al. |
| 6,068,679 A | 5/2000 | Zheng |
| 6,072,091 A | 6/2000 | Cosyns et al. |
| 6,087,294 A | 7/2000 | Klabunde et al. |
| 6,090,312 A | 7/2000 | Ziaka et al. |
| 6,096,932 A | 8/2000 | Subramanian |
| 6,096,933 A | 8/2000 | Cheung et al. |
| 6,103,215 A | 8/2000 | Zones et al. |
| 6,107,561 A | 8/2000 | Thompson |
| 6,117,371 A | 9/2000 | Mack |
| 6,124,514 A | 9/2000 | Emmrich et al. |
| 6,127,588 A | 10/2000 | Kimble et al. |
| 6,130,260 A | 10/2000 | Hall et al. |
| 6,143,939 A | 11/2000 | Farcasiu et al. |
| 6,169,218 B1 | 1/2001 | Hearn et al. |
| 6,180,841 B1 | 1/2001 | Fatutto et al. |
| 6,187,871 B1 | 2/2001 | Thompson et al. |
| 6,187,983 B1 | 2/2001 | Sun |
| 6,203,712 B1 | 3/2001 | Bronner et al. |
| 6,207,864 B1 | 3/2001 | Henningsen et al. |
| 6,225,517 B1 | 5/2001 | Nascimento et al. |
| 6,248,218 B1 | 6/2001 | Linkous et al. |
| 6,265,505 B1 | 7/2001 | McConville et al. |
| 6,281,405 B1 | 8/2001 | Davis et al. |
| 6,320,085 B1 | 11/2001 | Arvai et al. |
| 6,337,063 B1 | 1/2002 | Rouleau et al. |
| 6,342,200 B1 | 1/2002 | Rouleau et al. |
| 6,368,490 B1 | 4/2002 | Gestermann |
| 6,369,283 B1 | 4/2002 | Guram et al. |
| 6,372,949 B1 | 4/2002 | Brown et al. |
| 6,376,731 B1 | 4/2002 | Evans et al. |
| 6,380,328 B1 | 4/2002 | McConville et al. |
| 6,380,423 B2 | 4/2002 | Banning et al. |
| 6,380,444 B1 | 4/2002 | Bjerrum et al. |
| 6,395,945 B1 | 5/2002 | Randolph |
| 6,403,840 B1 | 6/2002 | Zhou et al. |
| 6,406,523 B1 | 6/2002 | Connor et al. |
| 6,423,211 B1 | 7/2002 | Randolph et al. |
| 6,426,441 B1 | 7/2002 | Randolph et al. |
| 6,426,442 B1 | 7/2002 | Ichikawa et al. |
| 6,452,058 B1 | 9/2002 | Schweizer et al. |
| 6,455,650 B1 | 9/2002 | Lipian et al. |
| 6,462,243 B1 | 10/2002 | Zhou et al. |
| 6,465,696 B1 | 10/2002 | Zhou et al. |
| 6,465,699 B1 | 10/2002 | Grosso |
| 6,472,345 B2 | 10/2002 | Hintermann et al. |
| 6,472,572 B1 | 10/2002 | Zhou et al. |
| 6,475,463 B1 | 11/2002 | Elomari et al. |
| 6,475,464 B1 | 11/2002 | Rouleau et al. |
| 6,479,705 B2 | 11/2002 | Murata et al. |
| 6,482,997 B2 | 11/2002 | Petit-Clair et al. |
| 6,486,368 B1 | 11/2002 | Zhou et al. |
| 6,495,484 B1 | 12/2002 | Holtcamp |
| 6,509,485 B2 | 1/2003 | Mul et al. |
| 6,511,526 B2 | 1/2003 | Jagger et al. |
| 6,514,319 B2 | 2/2003 | Keefer et al. |
| 6,518,474 B1 | 2/2003 | Sanderson et al. |
| 6,518,476 B1 | 2/2003 | Culp et al. |
| 6,525,228 B2 | 2/2003 | Chauvin et al. |
| 6,525,230 B2 | 2/2003 | Grosso |
| 6,528,693 B1 | 3/2003 | Gandy et al. |
| 6,538,162 B2 | 3/2003 | Chang et al. |
| 6,540,905 B1 | 4/2003 | Elomari |
| 6,545,191 B1 | 4/2003 | Stauffer |
| 6,547,958 B1 | 4/2003 | Elomari |
| 6,548,040 B1 | 4/2003 | Rouleau et al. |
| 6,552,241 B1 | 4/2003 | Randolph et al. |
| 6,566,572 B2 | 5/2003 | Okamoto et al. |
| 6,572,829 B2 | 6/2003 | Linkous et al. |
| 6,585,953 B2 | 7/2003 | Roberts et al. |
| 6,616,830 B2 | 9/2003 | Elomari |
| 6,620,757 B2 | 9/2003 | McConville et al. |
| 6,632,971 B2 | 10/2003 | Brown et al. |
| 6,635,793 B2 | 10/2003 | Mul et al. |
| 6,641,644 B2 | 11/2003 | Jagger et al. |
| 6,646,102 B2 | 11/2003 | Boriack et al. |
| 6,669,846 B2 | 12/2003 | Perriello |
| 6,672,572 B2 | 1/2004 | Werlen |
| 6,679,986 B1 | 1/2004 | Da Silva et al. |
| 6,680,415 B1 | 1/2004 | Gulotty, Jr. et al. |
| 6,692,626 B2 | 2/2004 | Keefer et al. |
| 6,692,723 B2 | 2/2004 | Rouleau et al. |
| 6,710,213 B2 | 3/2004 | Aoki et al. |
| 6,713,087 B2 | 3/2004 | Tracy et al. |
| 6,713,655 B2 | 3/2004 | Yilmaz et al. |
| RE38,493 E | 4/2004 | Keefer et al. |
| 6,723,808 B2 | 4/2004 | Holtcamp |
| 6,727,400 B2 | 4/2004 | Messier et al. |
| 6,740,146 B2 | 5/2004 | Simonds |
| 6,753,390 B2 | 6/2004 | Ehrman et al. |
| 6,765,120 B2 | 7/2004 | Weber et al. |
| 6,797,845 B1 | 9/2004 | Hickman et al. |
| 6,797,851 B2 | 9/2004 | Martens et al. |
| 6,821,924 B2 | 11/2004 | Gulotty, Jr. et al. |
| 6,822,123 B2 | 11/2004 | Stauffer |
| 6,822,125 B2 | 11/2004 | Lee et al. |
| 6,825,307 B2 | 11/2004 | Goodall |
| 6,825,383 B2 | 11/2004 | Dewkar et al. |
| 6,831,032 B2 | 12/2004 | Spaether |
| 6,838,576 B1 | 1/2005 | Wicki et al. |
| 6,841,063 B2 | 1/2005 | Elomari |
| 6,852,896 B2 | 2/2005 | Stauffer |
| 6,866,950 B2 | 3/2005 | Connor et al. |
| 6,869,903 B2 | 3/2005 | Matsunaga |
| 6,875,339 B2 | 4/2005 | Rangarajan et al. |
| 6,878,853 B2 | 4/2005 | Tanaka et al. |
| 6,888,013 B2 | 5/2005 | Paparatto et al. |
| 6,900,363 B2 | 5/2005 | Harth et al. |
| 6,902,602 B2 | 6/2005 | Keefer et al. |
| 6,903,171 B2 | 6/2005 | Rhodes et al. |
| 6,909,024 B1 | 6/2005 | Jones et al. |
| 6,921,597 B2 | 7/2005 | Keefer et al. |
| 6,933,417 B1 | 8/2005 | Henley et al. |
| 6,946,566 B2 | 9/2005 | Yaegashi et al. |
| 6,953,868 B2 | 10/2005 | Boaen et al. |
| 6,953,873 B2 | 10/2005 | Cortright et al. |
| 6,956,140 B2 | 10/2005 | Ehrenfeld |
| 6,958,306 B2 | 10/2005 | Holtcamp |
| 6,984,763 B2 | 1/2006 | Schweizer et al. |
| 7,001,872 B2 | 2/2006 | Pyecroft et al. |
| 7,002,050 B2 | 2/2006 | Santiago Fernandez et al. |
| 7,011,811 B2 | 3/2006 | Elomari |
| 7,019,182 B2 | 3/2006 | Grosso |
| 7,026,145 B2 | 4/2006 | Mizrahi et al. |
| 7,026,519 B2 | 4/2006 | Santiago Fernandez et al. |
| 7,037,358 B2 | 5/2006 | Babicki et al. |
| 7,045,670 B2 | 5/2006 | Johnson et al. |
| 7,049,388 B2 | 5/2006 | Boriack et al. |
| 7,053,252 B2 | 5/2006 | Boussand et al. |
| 7,057,081 B2 | 6/2006 | Allison et al. |
| 7,060,865 B2 | 6/2006 | Ding et al. |
| 7,064,238 B2 | 6/2006 | Waycuilis |
| 7,064,240 B2 | 6/2006 | Ohno et al. |

| | | |
|---|---|---|
| 7,067,448 B1 | 6/2006 | Weitkamp et al. |
| 7,083,714 B2 | 8/2006 | Elomari |
| 7,084,308 B1 | 8/2006 | Stauffer |
| 7,091,270 B2 | 8/2006 | Zilberman et al. |
| 7,091,387 B2 | 8/2006 | Fong et al. |
| 7,091,391 B2 | 8/2006 | Stauffer |
| 7,094,936 B1 | 8/2006 | Owens et al. |
| 7,098,371 B2 | 8/2006 | Mack et al. |
| 7,105,710 B2 | 9/2006 | Boons et al. |
| 7,138,534 B2 | 11/2006 | Forlin et al. |
| 7,141,708 B2 | 11/2006 | Marsella et al. |
| 7,145,045 B2 | 12/2006 | Harmsen et al. |
| 7,148,356 B2 | 12/2006 | Smith, III et al. |
| 7,148,390 B2 | 12/2006 | Zhou et al. |
| 7,151,199 B2 | 12/2006 | Martens et al. |
| 7,161,050 B2 | 1/2007 | Sherman et al. |
| 7,169,730 B2 | 1/2007 | Ma et al. |
| 7,176,340 B2 | 2/2007 | Van Broekhoven et al. |
| 7,176,342 B2 | 2/2007 | Bellussi et al. |
| 7,182,871 B2 | 2/2007 | Perriello |
| 7,193,093 B2 | 3/2007 | Murray et al. |
| 7,196,239 B2 | 3/2007 | Van Egmond et al. |
| 7,199,083 B2 | 4/2007 | Zevallos |
| 7,199,255 B2 | 4/2007 | Murray et al. |
| 7,208,641 B2 | 4/2007 | Nagasaki et al. |
| 7,214,750 B2 | 5/2007 | McDonald et al. |
| 7,220,391 B1 | 5/2007 | Huang et al. |
| 7,226,569 B2 | 6/2007 | Elomari |
| 7,226,576 B2 | 6/2007 | Elomari |
| 7,230,150 B2 | 6/2007 | Grosso et al. |
| 7,230,151 B2 | 6/2007 | Martens et al. |
| 7,232,872 B2 | 6/2007 | Shaffer et al. |
| 7,238,846 B2 | 7/2007 | Janssen et al. |
| 7,244,795 B2 | 7/2007 | Agapiou et al. |
| 7,244,867 B2 | 7/2007 | Waycuilis |
| 7,250,107 B2 | 7/2007 | Benazzi et al. |
| 7,250,542 B2 | 7/2007 | Smith, Jr. et al. |
| 7,252,920 B2 | 8/2007 | Kurokawa et al. |
| 7,253,327 B2 | 8/2007 | Janssens et al. |
| 7,253,328 B2 | 8/2007 | Stauffer |
| 7,265,193 B2 | 9/2007 | Weng et al. |
| 7,267,758 B2 | 9/2007 | Benazzi et al. |
| 7,268,263 B1 | 9/2007 | Frey et al. |
| 7,271,303 B1 | 9/2007 | Sechrist et al. |
| 7,273,957 B2 | 9/2007 | Bakshi et al. |
| 7,282,603 B2 | 10/2007 | Richards |
| 7,285,698 B2 | 10/2007 | Liu et al. |
| 7,297,825 B2 * | 11/2007 | Fujimoto et al. ............... 585/310 |
| 7,304,193 B1 | 12/2007 | Frey et al. |
| 7,342,144 B2 | 3/2008 | Kaizik et al. |
| 7,348,295 B2 | 3/2008 | Zones et al. |
| 7,348,464 B2 | 3/2008 | Waycuilis |
| 7,357,904 B2 | 4/2008 | Zones et al. |
| 7,361,794 B2 | 4/2008 | Grosso |
| 7,390,395 B2 | 6/2008 | Elomari |
| 8,053,616 B2 * | 11/2011 | Gadewar et al. ............... 585/310 |
| 2002/0102672 A1 | 8/2002 | Mizrahi |
| 2002/0198416 A1 | 12/2002 | Zhou et al. |
| 2003/0004380 A1 | 1/2003 | Grumann |
| 2003/0065239 A1 | 4/2003 | Zhu |
| 2003/0069452 A1 | 4/2003 | Sherman et al. |
| 2003/0078456 A1 | 4/2003 | Yilmaz et al. |
| 2003/0120121 A1 | 6/2003 | Sherman et al. |
| 2003/0125589 A1 | 7/2003 | Grosso |
| 2003/0166973 A1 | 9/2003 | Zhou et al. |
| 2004/0006246 A1 | 1/2004 | Sherman et al. |
| 2004/0062705 A1 | 4/2004 | Leduc |
| 2004/0152929 A1 | 8/2004 | Clarke |
| 2004/0158107 A1 | 8/2004 | Aoki |
| 2004/0158108 A1 | 8/2004 | Snoble |
| 2004/0187684 A1 | 9/2004 | Elomari |
| 2005/0047927 A1 | 3/2005 | Lee et al. |
| 2005/0148805 A1 | 7/2005 | Jones |
| 2005/0171393 A1 | 8/2005 | Lorkovic |
| 2005/0192468 A1 | 9/2005 | Sherman et al. |
| 2005/0215837 A1 | 9/2005 | Hoffpauir |
| 2005/0234276 A1 | 10/2005 | Waycuilis |
| 2005/0245772 A1 | 11/2005 | Fong |
| 2005/0245777 A1 | 11/2005 | Fong |
| 2005/0267224 A1 | 12/2005 | Herling |
| 2006/0025617 A1 | 2/2006 | Begley |
| 2006/0100469 A1 | 5/2006 | Waycuilis |
| 2006/0135823 A1 | 6/2006 | Jun |
| 2006/0138025 A1 | 6/2006 | Zones |
| 2006/0138026 A1 | 6/2006 | Chen |
| 2006/0149116 A1 | 7/2006 | Slaugh |
| 2006/0229228 A1 | 10/2006 | Komon et al. |
| 2006/0229475 A1 | 10/2006 | Weiss et al. |
| 2006/0270863 A1 | 11/2006 | Reiling |
| 2006/0288690 A1 | 12/2006 | Elomari |
| 2007/0004955 A1 | 1/2007 | Kay |
| 2007/0078285 A1 | 4/2007 | Dagle |
| 2007/0100189 A1 | 5/2007 | Stauffer |
| 2007/0129584 A1 | 6/2007 | Basset |
| 2007/0142680 A1 | 6/2007 | Ayoub |
| 2007/0148067 A1 | 6/2007 | Zones |
| 2007/0148086 A1 | 6/2007 | Zones |
| 2007/0149778 A1 | 6/2007 | Zones |
| 2007/0149789 A1 | 6/2007 | Zones |
| 2007/0149819 A1 | 6/2007 | Zones |
| 2007/0149824 A1 | 6/2007 | Zones |
| 2007/0149837 A1 | 6/2007 | Zones |
| 2007/0197801 A1 | 8/2007 | Bolk |
| 2007/0197847 A1 | 8/2007 | Liu |
| 2007/0213545 A1 | 9/2007 | Bolk |
| 2007/0238905 A1 | 10/2007 | Arredondo |
| 2007/0238909 A1 * | 10/2007 | Gadewar et al. ............... 585/16 |
| 2007/0251382 A1 | 11/2007 | Gadewar |
| 2007/0276168 A1 | 11/2007 | Garel |
| 2007/0284284 A1 | 12/2007 | Zones |
| 2008/0171898 A1 | 7/2008 | Waycuilis |
| 2008/0183022 A1 | 7/2008 | Waycuilis |
| 2008/0188697 A1 | 8/2008 | Lorkovic |
| 2008/0269534 A1 | 10/2008 | Lorkovic |
| 2008/0314758 A1 | 12/2008 | Grosso |
| 2009/0069606 A1 | 3/2009 | Komon |
| 2009/0127163 A1 | 5/2009 | Weiss |
| 2010/0096588 A1 | 4/2010 | Gadewar |
| 2010/0099928 A1 | 4/2010 | Gadewar |
| 2010/0099930 A1 | 4/2010 | Stoimenov |
| 2010/0105972 A1 | 4/2010 | Lorkovic |
| 2010/0121119 A1 | 5/2010 | Sherman |

FOREIGN PATENT DOCUMENTS

| | | |
|---|---|---|
| CA | 1101441 | 5/1981 |
| CA | 1202610 | 4/1986 |
| CA | 2447761 A1 | 11/2002 |
| CA | 2471295 A1 | 7/2003 |
| CA | 2542857 | 5/2005 |
| CA | 2236126 | 8/2006 |
| CA | 2203115 | 9/2006 |
| CA | 2510093 | 12/2006 |
| EP | 0021497 | 1/1981 |
| EP | 0164798 A1 | 12/1985 |
| EP | 0418971 A1 | 3/1991 |
| EP | 0418974 A1 | 3/1991 |
| EP | 0418975 A1 | 3/1991 |
| EP | 0510238 A1 | 10/1992 |
| EP | 0526908 A2 | 2/1993 |
| EP | 0346612 B1 | 8/1993 |
| EP | 0560546 A1 | 9/1993 |
| EP | 0976705 A1 | 7/1998 |
| EP | 1186591 A2 | 3/2002 |
| EP | 1253126 A1 | 10/2002 |
| EP | 1312411 A2 | 5/2003 |
| EP | 1395536 | 3/2004 |
| EP | 1404636 | 4/2004 |
| EP | 1235769 B1 | 5/2004 |
| EP | 1435349 A2 | 7/2004 |
| EP | 1440939 A1 | 7/2004 |
| EP | 1474371 | 11/2004 |
| EP | 1235772 B1 | 1/2005 |
| EP | 1661620 A1 | 5/2006 |
| EP | 1760057 A1 | 3/2007 |
| EP | 1689728 B1 | 4/2007 |
| EP | 1808227 A1 | 7/2007 |
| EP | 1837320 A1 | 9/2007 |
| GB | 5125 | 0/1912 |

| | | |
|---|---|---|
| GB | 156122 | 3/1922 |
| GB | 294100 | 6/1929 |
| GB | 363009 | 12/1931 |
| GB | 402928 | 12/1933 |
| GB | 474922 A | 11/1937 |
| GB | 536491 | 5/1941 |
| GB | 553950 | 6/1943 |
| GB | 586483 | 3/1947 |
| GB | 775590 | 5/1957 |
| GB | 793214 | 4/1958 |
| GB | 796048 | 6/1958 |
| GB | 796085 | 6/1958 |
| GB | 883256 | 11/1961 |
| GB | 950975 | 3/1964 |
| GB | 950976 | 3/1964 |
| GB | 991303 | 5/1965 |
| GB | 995960 | 6/1965 |
| GB | 1015033 | 12/1965 |
| GB | 1104294 | 2/1968 |
| GB | 1133752 | 11/1968 |
| GB | 1172002 | 11/1969 |
| GB | 1212240 | 11/1970 |
| GB | 1233299 | 5/1971 |
| GB | 1253618 | 11/1971 |
| GB | 1263806 A | 2/1972 |
| GB | 1446803 | 8/1976 |
| GB | 1542112 | 3/1979 |
| GB | 2095243 A | 9/1982 |
| GB | 2095245 A | 9/1982 |
| GB | 2095249 A | 9/1982 |
| GB | 2116546 A | 9/1982 |
| GB | 2120249 A | 11/1983 |
| GB | 2185754 A | 7/1987 |
| GB | 2191214 A | 12/1987 |
| JP | 2004-529189 | 9/2004 |
| WO | 83/00859 | 3/1983 |
| WO | 85/04863 | 11/1985 |
| WO | 85/04867 | 11/1985 |
| WO | 90/08120 | 7/1990 |
| WO | 90/08752 | 8/1990 |
| WO | 91/18856 | 12/1991 |
| WO | 92/03401 | 3/1992 |
| WO | 92/12946 | 8/1992 |
| WO | 93/16798 | 9/1993 |
| WO | 96/22263 | 7/1996 |
| WO | 97/44302 | 11/1997 |
| WO | 98/12165 | 3/1998 |
| WO | 99/07443 | 2/1999 |
| WO | 00/07718 A1 | 2/2000 |
| WO | 00/09261 A1 | 2/2000 |
| WO | 01/14300 A1 | 3/2001 |
| WO | 01/38275 A1 | 5/2001 |
| WO | 01/44149 A1 | 6/2001 |
| WO | 02/094749 A1 | 11/2002 |
| WO | 02/094750 A1 | 11/2002 |
| WO | 02/094751 A2 | 11/2002 |
| WO | 02/094752 A1 | 11/2002 |
| WO | 03/000635 A1 | 1/2003 |
| WO | 03/002251 A2 | 1/2003 |
| WO | 03/018524 A1 | 3/2003 |
| WO | 03/020676 A1 | 3/2003 |
| WO | 03/022827 A1 | 3/2003 |
| WO | 03/043575 A2 | 5/2003 |
| WO | 03/051813 A1 | 6/2003 |
| WO | 03/062143 A1 | 7/2003 |
| WO | 03/062172 A2 | 7/2003 |
| WO | 03/078366 A1 | 9/2003 |
| WO | 2004/018093 A2 | 3/2004 |
| WO | 2004/067487 A2 | 8/2004 |
| WO | 2005/014168 A1 | 2/2005 |
| WO | 2005/019143 A1 | 3/2005 |
| WO | 2005/021468 A1 | 3/2005 |
| WO | 2005/035121 A2 | 4/2005 |
| WO | 2005/037758 A1 | 4/2005 |
| WO | 2005/054120 A2 | 6/2005 |
| WO | 2005/056525 A2 | 6/2005 |
| WO | 2005/058782 A1 | 6/2005 |
| WO | 2005/090272 A1 | 9/2005 |
| WO | 2005/095310 A2 | 10/2005 |
| WO | 2005/105709 A1 | 11/2005 |
| WO | 2005/105715 A1 | 11/2005 |
| WO | 2005/110953 A1 | 11/2005 |
| WO | 2005/113437 A1 | 12/2005 |
| WO | 2005/113440 A1 | 12/2005 |
| WO | 2006/007093 A1 | 1/2006 |
| WO | 2006/015824 A1 | 2/2006 |
| WO | 2006/019399 A2 | 2/2006 |
| WO | 2006/020234 A1 | 2/2006 |
| WO | 2006/036293 A1 | 4/2006 |
| WO | 2006/039213 A1 | 4/2006 |
| WO | 2006/039354 A2 | 4/2006 |
| WO | 2006/043075 A1 | 4/2006 |
| WO | 2006/053345 A1 | 5/2006 |
| WO | 2006-067155 A2 | 6/2006 |
| WO | 2006/067188 A1 | 6/2006 |
| WO | 2006/067190 A1 | 6/2006 |
| WO | 2006/067191 A1 | 6/2006 |
| WO | 2006/067192 A1 | 6/2006 |
| WO | 2006/067193 A1 | 6/2006 |
| WO | 2006/069107 A2 | 6/2006 |
| WO | 2006/071354 A1 | 7/2006 |
| WO | 2006/076942 A1 | 7/2006 |
| WO | 2006/083427 A1 | 8/2006 |
| WO | 2006-100312 A2 | 9/2006 |
| WO | 2006/104909 A2 | 10/2006 |
| WO | 2006/104914 A1 | 10/2006 |
| WO | 2006/111997 A1 | 10/2006 |
| WO | 2006/113205 A2 | 10/2006 |
| WO | 2006/118935 A1 | 11/2006 |
| WO | 2007/001934 A2 | 1/2007 |
| WO | 2007/017900 A2 | 2/2007 |
| WO | 2007/044139 A1 | 4/2007 |
| WO | 2007/046986 A2 | 4/2007 |
| WO | 2007/050745 A1 | 5/2007 |
| WO | 2007/071046 A1 | 6/2007 |
| WO | 2007/079038 A2 | 7/2007 |
| WO | 2007/091009 A2 | 8/2007 |
| WO | 2007/094995 | 8/2007 |
| WO | 2007/094995 A2 | 8/2007 |
| WO | 2007/107031 A1 | 9/2007 |
| WO | 2007/111997 A2 | 10/2007 |
| WO | 2007/114479 A1 | 10/2007 |
| WO | 2007/125332 A1 | 11/2007 |
| WO | 2007/130054 A1 | 11/2007 |
| WO | 2007/130055 A1 | 11/2007 |
| WO | 2007/141295 A1 | 12/2007 |
| WO | 2007/142745 A1 | 12/2007 |
| WO | 2008/036562 | 3/2008 |
| WO | 2008/036563 | 3/2008 |
| WO | 2008/106319 | 9/2008 |
| WO | 2008/157043 | 12/2008 |
| WO | 2008/157044 | 12/2008 |
| WO | 2008/157045 | 12/2008 |
| WO | 2008/157046 | 12/2008 |
| WO | 2008/157047 | 12/2008 |
| WO | 2010/009376 | 1/2010 |

OTHER PUBLICATIONS

U.S. Appl. No. 60/559,844, filed Apr. 6, 2004, Sherman et al.
U.S. Appl. No. 60/765,115, filed Feb. 3, 2006, Gadewar et al.
Abstract of JP2007045756, Hydrogenation method using diaphragm type hydrogenation catalyst, hydrogenation reaction apparatus and diaphragm type hydrogenation catalyst, Publication date: Feb. 22, 2007, Inventor: Shuji et al., esp@cenet database—worldwide.
Abstract of JP2007061594, Method for decomposing organohalogen compound and mobile decomposition system, Publication date: Mar. 15, 2007, Inventor: Koichi et al., esp@cenet database—worldwide.
Abstract of JP2007099729, Method for producing alpha-methylstyrene or cumene, Publication date: Apr. 19, 2007, Inventor: Toshio, esp@cenet database—worldwide.
Abstract of RO119778, Process for preparing perchloroethylene, Publication date: Mar. 30, 2005, Inventor: Horia et al., esp@cenet database—worldwide.
Abstract of WO0105737, Method for preparing a carboxylic acid, Publication date: Jan. 25, 2001, Inventor: Pascal et al., esp@cenet database—worldwide.

Abstract of WO0105738, Method for preparing a carboxylic acid, Publication date: Jan. 25, 2001, Inventor: Pascal et al., esp@cenet database—worldwide.
Abstract of WO2004092099, Method for producing cyclic enols, Publication date: Oct. 28, 2004, Inventor: Marko et al., esp@cenet database—worldwide.
Abstract of WO2006063852, Electroluminescent polymers and use thereof, Publication date: Jun. 22, 2006, Inventor: Arne et al., esp@cenet database—worldwide.
Abstract of WO2006136135, Method for decarboxylating C-C cross-linking of carboxylic acids with carbon electrophiles, Publication date: Dec. 28, 2006, Inventor: Goossen Lukas et al., esp@cenet database—worldwide.
Abstract of WO2007028761, Method for chlorinating alcohols, Publication date: Mar. 15, 2007, Inventor: Rohde et al., esp@cenet database—worldwide.
Abstract of WO2007128842, Catalytic transalkylation of dialkyl benzenes, Publication date: Nov. 15, 2007, Inventor: Goncalvesalmeida et al., esp@cenet database—worldwide.
Abstract of WO2007137566, Method for catalytic conversion of organic oxygenated compounds from biomaterials, Publication date: Dec. 6, 2007, Inventor: Reschetilowski, esp@cenet database—worldwide.
Abstract of WO9721656, Method for making fluoroalkanols, Publication date: Jun. 19, 1997, Inventor: Gillet, esp@cenet database—worldwide.
Abstract of WO9950213, Method for producing dialkyl ethers, Publication date: Oct. 7, 1999, Inventor: Falkowski Juergen et al., esp@cenet database—worldwide.
Adachi, et al.; Synthesis of Sialyl Lewis X Ganglioside Analogs Containing a Variable Length Spacer Between the Sugar and Lipophilic Moieties; J. Carbohydrate Chem., vol. 17, No. 4-5, (1998), pp. 595-607, XP009081720.
Abstract of EP0039471, Process for the preparation of 2-chloro-1,1,1,2,3,3,3-heptafluoropropane, Publication date: Nov. 11, 1981, Inventor: Von Halasz, esp@cenet database—worldwide.
Abstract of EP0101337, Process for the production of methylene chloride, Publication date: Feb. 22, 1984, Inventor: Olah et al., esp@cenet database—worldwide.
Abstract of EP0407989, Method for the production of 1,1,1-trifluoro-2,2-dichloroethane by photochlorination, Publication date: Jan. 16, 1991, Inventor: Cremer et al., esp@cenet database—worldwide.
Abstract of EP0442258, Process for the preparation of a polyunsaturated olefin, Publication date: Aug. 21, 1991, Inventor: Gaudin et al., esp@cenet database—worldwide.
Abstract of EP0465294, Process for the preparation of unsaturated bromides, Publication date: Jan. 8, 1992, Inventor: Decaudin et al., esp@cenet database—worldwide.
Abstract of EP0549387, Synthesis of n-perfluorooctylbromide, Publication date: Jun. 30, 1993, Inventor: Drivon et al., esp@cenet database—worldwide.
Abstract of EP0850906, Process and apparatus for the etherification of olefinic hydrocarbon feedstocks, Publication date: Jul. 1, 1998, Inventor: Masson, esp@cenet database—worldwide.
Abstract of EP0858987, Process for the conversion of lighter alkanes to higher hydrocarbons, Publication date: Aug. 19, 1998, Inventor: Amariglio et al., esp@cenet database—worldwide.
Bakker, et al.; An Exploratory Study of the Addition Reaction of Ethyleneglcol, 2-Chloroethanlo and 1, 3-Dichloro-2-Propanol to 1-Dodecene; J. Am. Oil Chem. Soc., vol. 44, No. 9 (1967), pp. 517-521; XP009081570.
Abstract of EP0235110, Process for the stabilization of silicalite catalysts, Publication date: Sep. 2, 1987, Inventor: Debras et al., esp@cenet database—worldwide.
Bouzide et al.; Highly Selective Silver (I) Oxide Mediated Monoprotection of Symmetricl Diols; Tetrahedron Letters, Elsevier, vol. 38, No. 34 (1997), pp. 5945-5948; XP004094157.
Combined International Search Report and Written Opinion Dated Apr. 17, 2007 for PCT/US06/13394, in the name of GRT, Inc.
Gibson; Phase-Transfer Synthesis of Monoalkyl Ethers of Oligoethylene Glycols; Journal of Organic Chemistry, vol. 45, No. 6 (1980) pp. 1095-1098; XP002427776.

Klabunde, Kenneth J., et al., Changes in Texture and Catalytic Activity of Nanocrystalline MgO during Its Transformation to MgC12 in the Reaction with 1-Chiorobutane, J. Phys. Chem. B 2001, 105, 3937-3941.
Loiseau et al.; Multigram Synthesis of Well-Defined Extended Bifunctional Polyethylene Glycol (PEG) Chains; J. of Organic Chem., vol. 69, No. 3 (2004), pp. 639-647; XP002345040.
Mihai et al.; Application of Bronsted-type LFER in the study of phospholipase C mechanism; J. Am. Chem. Soc., vol. 125, No. 11 (2003) pp. 3236-3242; XP002427799.
Motupally et al., Recycling Chlorine from Hydrogen Chloride: A New and Economical Electrolytic Process, The Electrochemical Society Interface, Fall 1998.
Nishikawa et al.; Ultrasonic Relaxations in Aqueous Solutions of Alcohols and the Balance Between Hydrophobicity and Hydrophilicity of the Solutes; J. Phys. Chem. vol. 97, No. 14 (1993), pp. 3539-3544; XP002427775.
Prelog et al.; Chirale 2,2'-Polyoxaalkano-9,9'-Spirobifluorene; Helvetica Chimica ACTA, vol. 62, No. 7, (1979) pp. 2285-2302; XP002030901.
Shimizu et al., Gas-Phase Electrolysis of Hydrobromic Acid Using PTFE-Bonded Carbon Eletrode, Int. J. Hydrogen Energy, vol. 13, No. 6. pp. 345-349, 1988.
Velzen et al., HBr Electrolysis in the Ispra Mark 13A Flue Gas Desulphurization Process: Electrolysis in a DEM Cell, J. Of Applied Electrochemistry, vol. 20, pp. 60-68, 1990.
Whitesides et al.; Nuclear Magnetic Resonance Spectroscopy. The Effect of Structure on Magnetic Nonequivalence Due to Molecular Asymmetry; J. Am. Chem. Soc., vol. 86, No. 13 (1964) pp. 2628-2634; XP002427774.
JLM Technology Ltd.; "The Miller GLS Technology for Conversion of Light Hydrocarbons to Alcohols"; New Science for the Benefit of Humanity; May 31, 2000; pp. 1-10.
Jaumain, Denis and Su, Bao-Lian; "Direct Catalytic Conversion of Chloromethane to Higher Hydrocarbons Over Various Protonic and Cationic Zeolite Catalysts as Studied by in-situ FTIR and Catalytic Testing"; 2000; pp. 1607-1612; Studies in Surface Science and Catalysis 130; Elsevier Science B.V.
Taylor, Charles E.; "Conversion of Substituted Methanes Over ZSM-Catalysts"; 2000; pp. 3633-3638; Studies in Surface Science and Catalysis 130; Elsevier Science B.V.
ZSM-5 Catalyst; http://chemelab.ucsd.edu/methanol/memos/ZSM-5.html; Nov. 6, 2003; p. 1.
Final Report; "Abstract"; http://chemelab.ucsd.edu/methanol/memos/final.html; May 9, 2004; pp. 1-7.
Driscoll, Daniel J.; "Direct Methane Conversion"; Federal Energy Technology Center, U.S. Department of Energy; M970779; 2001; pp. 1-10.
Olah et al.; "Selective Monohalogenation of Methane over Supported Acid or Platinum Metal Catalysts and Hydrolysis of Methyl Halides . . ."; J. American Chemical Society 1985, vol. 107; 0002-7863/85/1507-7097$01.50/0; pp. 7097-7105.
Murray et al.; "Conversion of Methyl Halides to Hydrocarbons on Basic Zeolites: A Discovery by in Situ NMR"; J. American Chemical Society 1993, vol. 115; pp. 4732-4741.
Lorkovic et al.; "A Novel Integrated Process for the Functionalization of Methane and Ethane: Bromine as Mediator", Catalysis Today 98; 2004; pp. 317-322.
Lorkovic et al.; "C1 Oxidative Coupling via Bromine Activation and Tandem Catalytic Condensation over CaO/Zeolite Composites II . . ."; Catalysis Today 98; 2004; pp. 589-594.
Olah et al.; "Antimony Pentafluoride/Graphite Catalyzed Oxidative Conversion of Methyl Halides with Copper Oxides (or Copper/Oxygen) to Dimethyl Ether"; J. Org. Chem. 1990, 55; 1990 American Chemical Society; pp. 4289-4293.
Taylor, Charles E. et al.; "Direct Conversion of Methane to Liquid Hydrocarbons Through Chlorocarbon Intermediates"; 1988 Elsevier Science Publishers B.V. Amsterdam, Netherlands; pp. 483-489.
Chang, Clarence D. et al.; "The Conversion of Methanol and Other O-Compounds to Hydrocarbons over Zeolite Catalysts"; Journal of Catalysis 47; 1977; Academic Press, Inc.; pp. 249-259.

Zhou, Xiao-Ping et al.; "An Integrated Process for Partial Oxidation of Alkanes"; Chem. Commun. 2003; The Royal Society of Chemistry 2003; pp. 2294-2295.

Sun, Shouli et al.; "A General Integrated Process for Synthesizing Olefin Oxides"; Chem. Commun. 2004; The Royal Society of Chemistry 2004; pp. 2100-2101.

Lorkovic, Ivan M. et al.; "C1 Oxidative Coupling via Bromine Activation and Tandem Catalytic Condensation and Neutralization over CaO/Zeolite Composites 11 . . ."; Catalysis Today 98; 2004; pp. 589-594.

Yilmaz, Aysen et al.; "Bromine Mediated Partial Oxidation of Ethane over Nanostructured Zirconia Supported Metal Oxide/Bromide"; Microporous and Mesporous Materials, 79; 2005; pp. 205-214.

Taylor, Charles E.; "PETC's On-Site Natural Gas Conversion Efforts"; Preprints of the Fuel Division, 208th National Meeting of the American Chemical Society, 39 (4); 1994; pp. 1228-1232.

Ione et al.; "Syntheses of Hydrocarbons from Compounds Containing One Carbon Atom Using Bifunctional Zeolite Catalysts"; Solid Fuel Chemistry (Khimiya Tverdogo Topliva); 1982; pp. 29-43; vol. 16, No. 6; Allerton Press. Inc.

Olah, George A. et al.; "Hydrocarbons Through Methane Derivatives"; Hydrocarbon Chemistry; 1995; pp. 89-90; John Wiley & Sons, Inc.

Akhrem, Irene S. et al.; "Ionic Bromination of Ethane and Other Alkanes (Cycloalkanes) with Bromine Catalyzed by the Polyhalomethane-2AlBr3 Aprotic Organic Superacids Under Mild Conditions"; Tetrahedron Letters, vol. 36, No. 51, 1995; pp. 9365-9368; Pergamon; Great Britain.

Smirnov, Vladimir V. et al.; "Selective Bromination of Alkanes and Arylalkanes with CBr4"; Mendeleev Commun. 2000; pp. 175-176.

Olah, George A.; "Electrophilic Methane Conversion"; Acc. Chem. Res. 1987, 20; pp. 422-428; American Chemical Society, Loker Hydrocarbon Research Institute and Dept. of Chemistry; University of Southern California.

Olah, George A. et al.; "Antimony Pentafluoride/Graphite Catalyzed Oxidative Carbonylation of Methyl Halides with Carbon Monoxide and Copper Oxides (or Copper/Oxygen) to Methyl Acetate"; J. Org. Chem. 1990, 55; pp. 4293-4297; Loker Hydrocarbon Research Institute and Dept. of Chemistry; University of Southern California.

Bagno, Alessandro et al.; "Superacid-Catalyzed Carbonylation of Methane, Methyl Halides, Methyl Alcohol, and Dimethyl Ether to Methyl Acetate and Acetic Acid"; J. Org. Chem. 1990, 55; pp. 4284-4289; Loker Hydrocarbon Research Institute; University of Southern California.

Olah, George A. et al.; "Onium Ylide Chemistry. 1. Bifunctional Acid-Base-Catalyzed Conversion of Heterosubstituted Methanes into Ethylene and Derived Hydrocarbons. The Onium Ylide Mechanism of the C1-C2 Conversion"; J. Am. Chem. Soc. 1984, 106; pp. 2143-2149.

Mochida, Isao et al.; "The Catalytic Dehydrohalogenation of Haloethanes on Solid Acids and Bases"; Bulletin of the Chemical Society of Japan, vol. 44; 1971; pp. 3305-3310.

Richards, Ryan et al.; "Nanocrystalline Ultra High Surface Area Magnesium Oxide as a Selective Base Catalyst"; Scripta Materialia, 44; 2001; pp. 1663-1666; Elsevier Science Ltd.

Sun, Naijian et al.; "Nanocrystal Metal Oxide—Chlorine Adducts: Selective Catalysts for Chlorination of Alkanes"; J. Am. Chem. Soc. 1999, 121; pp. 5587-5588; American Chemical Society.

Mishakov, Ilya V. et al.; "Nanocrystalline MgO as a Dehydrohalogenation Catalyst"; Journal of Catalysis 206; 2002; pp. 40-48; Elsevier Science, USA.

Wagner, George W. et al.; "Reactions of VX, GD, and HD with Nanosize CaO: Autocatalytic Dehydrohalogenation of HD"; J. Phys. Chem. B 2000, 104; pp. 5118-5123; 2000 American Chemical Society.

Fenelonov, Vladimir B. et al.; "Changes in Texture and Catalytic Activity of Nanocrystalline MgO during Its Transformation to MgCl2 in the Reaction with 1-Chlorobutane"; J. Phys. Chem. B 2001, 105; pp. 3937-3941; 2001 American Chemical Society.

http://webbook.nist.gov/; "Welcome to the NIST Chemistry WebBook"; 2005; U.S. Secretary of Commerce on Behalf of the United States of America.

Claude, Marion C. et al.; "Monomethyl-Branching of Long n-Alkanes in the Range from Decane to Tetracosane on Pt/H-ZSM-22 Bifunctional Catalyst"; Journal of Catalysis 190; 2000; pp. 39-48.

Thomas, J. M. et al.; "Synthesis and Characterization of a Catalytically Active Nickel-Silicoaluminophosphate Catalyst for the Conversion of Methanol to Ethene"; Chem. Mater.; 1991, 3; pp. 667-672; 1991 American Chemical Society.

Thomas, John Meurig et al.; "Catalytically Active Centres in Porous Oxides: Design and Performance of Highly Selective New Catalysts"; Chem. Commun.; 2001; pp. 675-687.

Lorkovic, Ivan et al.; "C1 Coupling via Bromine Activation and Tandem Catalytic Condensation and Neutralization over CaO/Zeolite Composites"; Chem. Commun., 2004; pp. 566-567.

Tamura, Masuhiko et al.; "The Reactions of Grignard Reagents with Transition Metal Halides: Coupling, Disproportionation, and Exchange with Olefins"; Bulletin of the Chemical Society of Japan, vol. 44.; Nov. 1971; pp. 3063-3073.

Weissermel, Klaus et al.; "Industrial Organic Chemistry"; 3rd Edition 1997. pp. 160-162, and 208.

Abstract of BE812868, Aromatic hydrocarbons prodn. from chlorinated hydrocarbons, Publication date: Sep. 27, 1974, esp@cenet database—worldwide.

Abstract of BE814900, Volatile aramatic cpds. prodn., Publication date: Sep. 2, 1974, esp@cenet database—worldwide.

Abstract of CN1199039, Pentanol and its production process, Publication date: Nov. 18, 1998, Inventor: Kailun, esp@cenet database—worldwide.

Abstract of CN1210847, Process for producing low carbon alcohol by directly hydrating low carbon olefines, Publication date: Mar. 17, 1999, Inventor: Zhenguo et al., esp@cenet database—worldwide.

Abstract of CN1321728, Method for preparing aromatic hydrocarbon and hydrogen gas by using low-pressure gas, Publication date: Nov. 14, 2001, Inventor: Jie et al., esp@cenet database—worldwide.

Abstract of CN1451721, Process for non-catalytic combustion deoxidizing coal mine gas for producing methanol, Publication date: Oct. 29, 2003, Inventor: Pengwan et al., esp@cenet database—worldwide.

Abstract of CN1623969, Method for preparing 1, 4-benzene dimethanol, Publication date: Jun. 8, 2005, Inventor: Jiarong et al., esp@cenet database—worldwide.

Abstract of CN1657592, Method for converting oil to multiple energy fuel product, Publication date: Aug. 8, 2005, Inventor: Li, esp@cenet database—worldwide.

Abstract of CN1687316, Method for producing biologic diesel oil from rosin, Publication date: Oct. 26, 2005, Inventor: Jianchun et al., esp@cenet database—worldwide.

Abstract of CN1696248, Method for synthesizing biologic diesel oil based on ion liquid, Publication date: Nov. 16, 2005, Inventor. Sun, esp@cenet database—worldwide.

Abstract of CN1699516, Process for preparing bio-diesel-oil by using microalgae fat, Publication date: Nov. 23, 2005, Inventor: Miao, esp@cenet database—worldwide.

Abstract of CN1704392, Process for producing alkylbenzene, Publication date: Dec. 7, 2005, Inventor: Gao, esp@cenet database—worldwide.

Abstract of CN1724612, Biological diesel oil catalyst and method of synthesizing biological diesel oil using sai catalyst, Publication date: Jan. 25, 2006, Inventor: Gu, esp@cenet database—worldwide.

Abstract of CN1986737, Process of producing biodiesel oil with catering waste oil, Publication date: Jun. 27, 2007, Inventor: Chen, esp@cenet database—worldwide.

Abstract of CN100999680, Esterification reaction tech. of preparing biodiesel by waste oil, Publication date: Jul. 18, 2007, Inventor: Weiming, esp@cenet database—worldwide.

Abstract of CN101016229, Refining method for bromomeoamyl alcohol, Publication date: Aug. 15, 2007, Inventor: Tian, esp@cenet database—worldwide.

Abstract of DE3209964, Process for the preparation of chlorinated hydrocarbons, Publication date: Nov. 11, 1982, Inventor: Pyke et al., esp@cenet database—worldwide.

Abstract of DE3210196, Process for the preparation of a monochlorinated olefin, Publication date: Jan. 5, 1983, Inventor: Pyke et al., esp@cenet database—worldwide.

Abstract of DE3226028, Process for the preparation of monochlorinated olefin, Publication date: Feb. 3, 1983, Inventor: Pyke et al., esp@cenet database—worldwide.

Abstract of DE3334225, Process for the preparation of 1, 2-dichloroethane, Publication date: Apr. 4, 1985, Inventor: Hebgen et al., esp@cenet database—worldwide.

Abstract of DE4232056, 2,5-Di:methyl-hexane-2, 5-di:ol continuous prodn. from tert. butanol—by oxidative dimerisation in two phase system with vigorous stirring, using aq. phase with specified density to facilitate phase sepn., Publication date: Mar. 31, 1994, Inventor: Gnann et al., esp@cenet database—worldwide.

Abstract of DE4434823, Continuous prodn. of hydroxy-benzyl alkyl ether, Publication date: Apr. 4, 1996, Inventor: Stein et al., esp@cenet database—worldwide.

Abstract of FR2692259, Aromatisation of 2-4C hydrocarbons—using a fixed-mobile-catalytic bed process, Publication date: Dec. 17, 1993, Inventor: Alario et al., esp@cenet database—worldwide.

Abstract of FR2880019, Manufacturing 1, 2-dichloroethane, comprises cracking core hydrocarbonated source, separating into fractions, sending into chlorination reaction chamber and oxychlorination reaction chamber and separating from chambers, Publication date: Jun. 30, 2006, Inventor: Strebelle et al., esp@cenet database—worldwide.

Abstract of FR2883870, Formation of 1, 2-dichloroethane useful in manufacture of vinyl chloride involves subjecting mixture of cracking products obtained by cracking of hydrocarbon source, to a succession of aqueous quenching, alkaline washing, and oxidation steps, Publication date: Oct. 6, 2006, Inventor: Balthasart et al., esp@cenet database—worldwide.

Abstract of FR2883871, Preparing 1, 2-dichloroethane comprises cracking hydrocarbon to form mixture, sending mixture into storage reservoir, supplying mixture into chlorination and/or oxychloration reactor, and separating 1, 2-dichloroethane from reactor, Publication date: Oct. 6, 2006, Inventor: Balthasart et al., esp@cenet database—worldwide.

Abstract of 1T1255246, Process for the preparation of dinitrodiphenylmethanes, Publication date: Oct. 20, 1995, Applicant:. Enichem Spa et al., esp@cenet database—worldwide.

Abstract of 1T1255358, Process for the synthesis of 1, 4-butanediol, Publication date: Oct. 31, 1995, Inventor Marco, esp@cenet database—worldwide.

Abstract of JP2142740, Production of fluoroalcohol, Publication date: May 31, 1990, Inventor: Tsutomu et al., esp@cenet database—worldwide.

Abstract of JP2144150, Chemical process and catalyst used therefore, Publication date: Jun. 1, 1990, Inventor Deidamusu et al., esp@cenet database—worldwide.

Abstract of JP4305542, Production of halogenated hydrocarbon compounds, Publication date: Oct. 28, 1992, Inventor: Shinsuke et al., esp@cenet database—worldwide.

Abstract of JP6172225, Method for fluorinating halogenated hydrocarbon, Publication date: Jun. 21, 1994, Inventor: Takashi et al., esp@cenet database—worldwide.

Abstract of JP6206834, Production of tetrachloroethanes, Publication date: Jul. 26, 1994, Inventor: Toshiro et al., esp@cenet database—worldwide.

Abstract of JP8266888, Method for decomposing aromatic halogen compound, Publication date: Oct. 15, 1996, Inventor. Yuuji et al., esp@cenet database—worldwide.

Abstract of JP2001031605, Production of 3-hydroxy-1-cycloalkene, Publication date: Feb. 6, 2001, Inventor: Hideo et al, esp@cenet database—worldwide.

Abstract of JP2004075683, Method for producing optically active halogenohydroxypropyl compound and glycidyl compound, Publication date: Mar. 11, 2004, Inventor: Keisuke et al., esp@cenet database—worldwide.

Abstract of JP2004189655, Method for fluorinating with microwave, Publication date: Jul. 8, 20048, Inventor: Masaharu et al., esp@cenet database—worldwide.

Abstract of JP2005075798, Method for Producing adamantyl ester compound, Publication date: Mar. 24, 2005, Inventor Norihiro et al., esp@cenet database—worldwide.

Abstract of JP2005082563, Method for producing 1, 3-adamantanediol, Publication date: Mar. 31, 2005, Inventor Norihiro et al., esp@cenet database—worldwide.

Abstract of JP2005145977, Process for catalytically oxidizing olefin and cycloolefin for the purpose of forming enol, olefin ketone, and epoxide, Publication date: Jun. 9, 2005, Inventor Cancheng et al., esp@cenet database—worldwide.

Abstract of JP2005254092, Method of manufacturing alkynes, Publication date: Sep. 22, 2005, Inventor: Shirakawa Eiji, esp@cenet database—worldwide.

Abstract of JP2006151892, Preparation method of alcohol derivative, Publication date: Jun. 15, 2006, Inventor: Baba Akio et al., esp@cenet database—worldwide.

Abstract of JP2006152263, Organic-inorganic hybrid-type mesoporous material, method for producing the same, and solid catalyst, Publication date: Jun. 15, 2006, Inventor: Junko et al., esp@cenet database—worldwide.

Abstract of JP2006193473, Aryl polyadamantane derivative having carboxy or acid anhydride group and method for producing the same, Publication date: Jul. 27, 2006, Inventor: Yasuto et al., esp@cenet database—worldwide.

Abstract of JP2006231318, Phosphorus containing macromolecule immobilizing palladium catalyst and method for using the same, Publication date: Sep. 7, 2006, Inventor: Osamu et al., esp@cenet database—worldwide.

Abstract of JP2006263567, Optical resolution method of optical isomer and optical resolution device, Publication date: Oct. 5, 2006, Inventor: Yoshikazu et al., esp@cenet database—worldwide.

Abstract of JP2006265157, Method for catalytically activating silicated nucleating agent using phosphazene base, Publication date: Oct. 5, 2006, Inventor: Yoshinori et al., esp@cenet database—worldwide.

Abstract of JP2006306758, Method for producing biaryl compound, Publication date: Nov. 9, 2006, Inventor: Yuji et al., esp@cenet database—worldwide.

Abstract of JP2007001942, Production method of para-xylene, Publication date: Jan. 11, 2007, Inventor: Kazuyoshi, esp@cenet database—worldwide.

Abstract of JP2007015994, Method for synthesizing organic compound in ultra high rate under high temperature and high pressure water, and system of high temperature and high pressure reaction, Publication date: Jan. 25, 2007, Inventor: Hajime et al., esp@cenet database—worldwide.

U.S. Office Action from U.S. Appl. No. 10/826,885 dated Oct. 31, 2005.

U.S. Office Action from U.S. Appl. No. 10/826,885 dated Apr. 19, 2006.

U.S. Office Action from U.S. Appl. No. 10/826,885 dated Jul. 27, 2006.

U.S. Office Action from U.S. Appl. No. 10/826,885 dated Nov. 2, 2006.

U.S. Office Action from U.S. Appl. No. 10/826,885 dated Jan. 24, 2007.

U.S. Office Action from U.S. Appl. No. 11/101,886 dated Jan. 24, 2007.

U.S. Office Action from U.S. Appl. No. 11/254,438 dated Jan. 24, 2007.

U.S. Office Action from U.S. Appl. No. 11/254,438 dated Nov. 1, 2007.

U.S. Office Action from U.S. Appl. No. 10/893,418 dated Jan. 2, 2008.

U.S. Office Action from U.S. Appl. No. 10/893,418 dated Jun. 14, 2007.

U.S. Office Action from U.S. Appl. No. 11/091,130 dated Oct. 3, 2007.

U.S. Office Action from U.S. Appl. No. 10/365,346 dated Jun. 12, 2006.

U.S. Office Action from U.S. Appl. No. 11/103,326 dated Aug. 31, 2007.

U.S. Office Action from U.S. Appl. No. 11/103,326 dated Dec. 6, 2006.

U.S. Office Action from U.S. Appl. No. 11/098,997 dated Nov. 20, 2008.

U.S. Office Action from U.S. Appl. No. 12/215,326 dated Feb. 10, 2009.
U.S. Office Action from U.S. Appl. No. 10/430,240 dated Mar. 6, 2006.
U.S. Office Action from U.S. Appl. No. 10/369,148 dated Oct. 16, 2006.
U.S. Office Action from U.S. Appl. No. 10/369,148 dated Mar. 14, 2006.
U.S. Office Action from U.S. Appl. No. 10/894,165 dated Aug. 16, 2006.
U.S. Office Action from U.S. Appl. No. 12/080,594 dated Dec. 22, 2008.
U.S. Office Action from U.S. Appl. No. 11/703,358 dated Jun. 11, 2008.
International Search Report for PCT/US09/50955 dated Nov. 2, 2009.
International Search Report for PCT/US07/03091 dated Jun. 7, 2008.
Office Action from U.S. Appl. No. 12/496,348 dated Feb. 3, 2011.
Communication from European Patent Office regarding Application No. 07749992.9 dated Jun. 9, 2011.
Communication from New Zealand Intellectual Property Office regarding Application No. 591207 dated Jun. 10, 2011.
Communication from New Zealand Intellectual Property Office regarding Application No. 588129 dated Feb. 9, 2012.
Office Action from U.S. Appl. No. 12/504,894 dated Apr. 1, 2011.
Office Action from U.S. Appl. No. 12/504,894 dated Jul. 19, 2011.
Office Action from U.S. Appl. No. 12/504,880 dated Mar. 2, 2012.

* cited by examiner

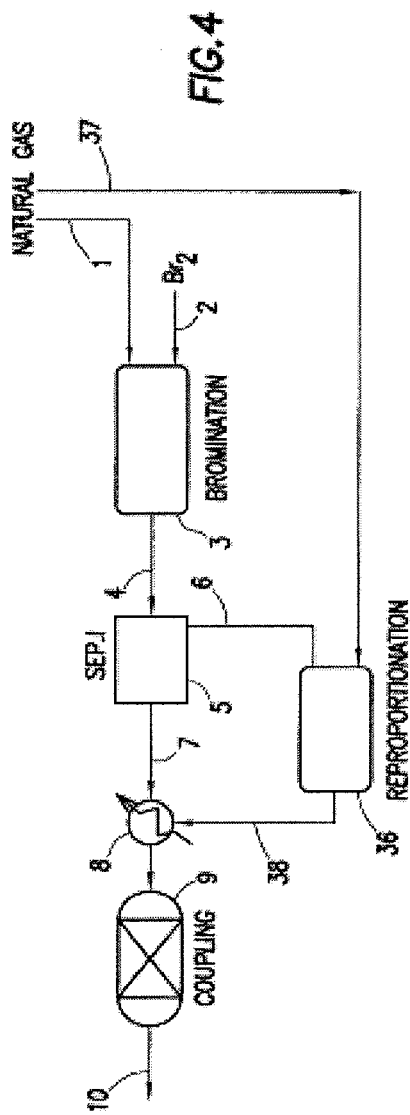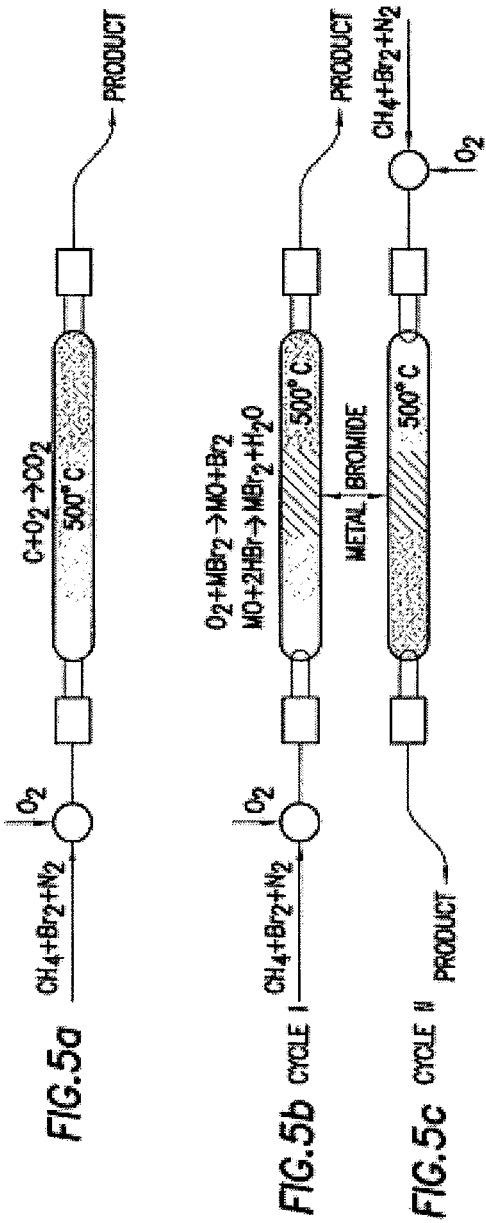

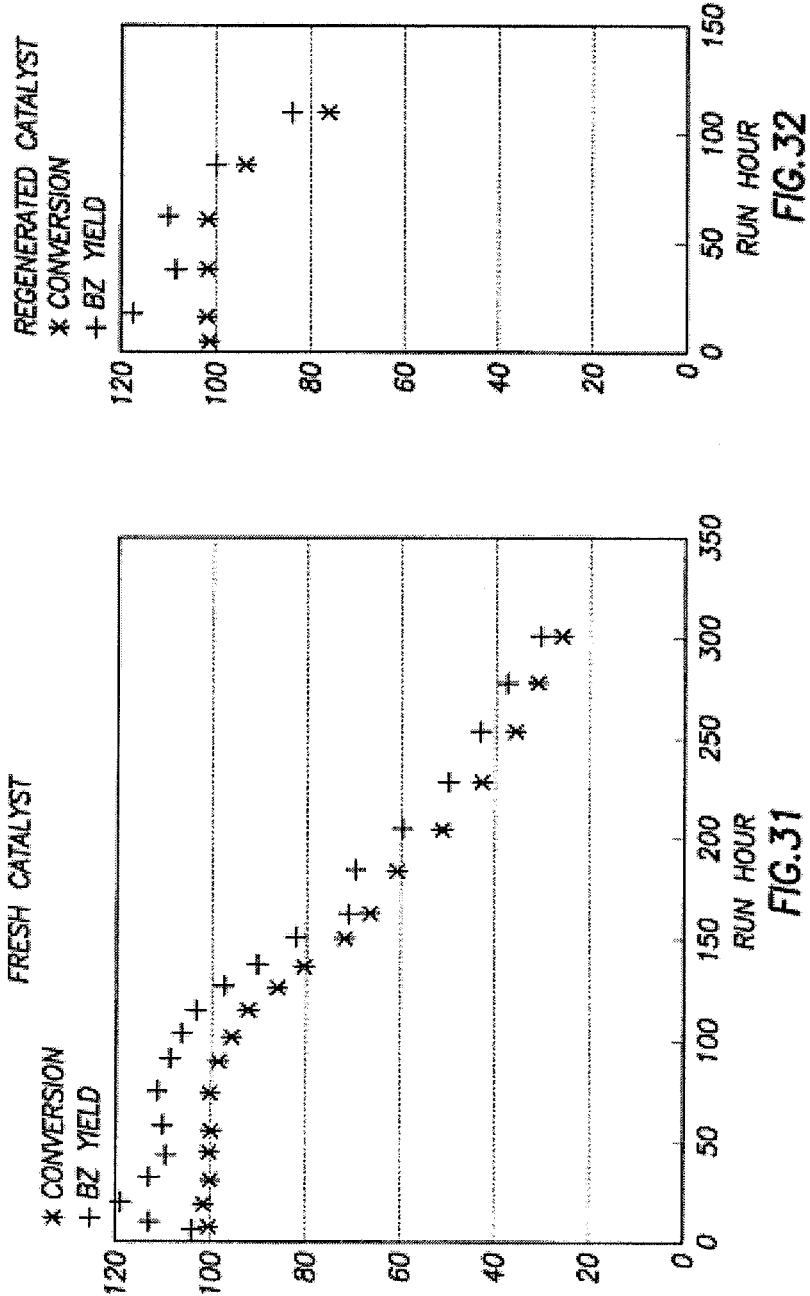

CONTINUOUS PROCESS FOR CONVERTING NATURAL GAS TO LIQUID HYDROCARBONS

CROSS-REFERENCE TO RELATED APPLICATION

This application is based on and claims priority U.S. Provisional Patent Application No. 61/081,976, filed Jul. 18, 2008, U.S. Provisional Patent Application No. 61/082,000, filed Jul. 18, 2008, U.S. Provisional Patent Application No. 61/082,115, filed Jul. 18, 2008, U.S. Provisional Patent Application No. 61/082,143, filed Jul. 18, 2008, and U.S. patent application Ser. No. 12/496,348, filed Jul. 1, 2009 which is a continuation of Ser. No. 11/703,358 filed Feb. 5, 2007, the entire contents of each provisional and application are incorporated by reference herein.

FIELD OF THE INVENTION

This invention generally relates to carbon-carbon coupling and, more particularly, to methods for converting hydrocarbon feedstocks into useful products.

BACKGROUND OF THE INVENTION

Scientists have long sought efficient ways to convert methane and other hydrocarbons into longer chain hydrocarbons, olefins, aromatic hydrocarbons, and other products. CH bond activation has been the focus of intense research for decades, with mixed results. More efficient processes may create value in a number of ways, including facilitating the utilization of remotely located hydrocarbon feedstocks (such as stranded natural gas) through conversion into more easily transportable and useful fuels and feedstocks, and allowing the use of inexpensive feedstocks (e.g., methane and other light hydrocarbons) for end products often made from higher hydrocarbons.

U.S. Pat. No. 6,525,230 discloses methods of converting alkanes to other compounds using a "zone reactor" comprised of a hollow, unsegregated interior defining first, second, and third zones. Oxygen reacts with metal bromide in the first zone to provide bromine; bromine reacts with the alkane in the second zone to form alkyl bromide and hydrogen bromide; and the alkyl bromide reacts with metal oxide in the third zone to form the corresponding product. In one embodiment, the flow of gases through the reactor may be reversed to convert the metal oxide back to metal bromide and to convert the metal bromide back to the metal oxide. The reactor may essentially operated in a cyclic mode.

Other processes may include an oxidative halogenation process for producing alkyl halides from an alkane, hydrogen halide, and, preferably, oxygen, using a rare earth halide or oxyhalide catalyst. A metal halide catalyst may also be used for oxidative halogenation of alkanes. Oxidative halogenation, however, has several disadvantages, including the production of perhalogenated products and an unacceptable quantity of deep oxidation products ($CO$ and $CO_2$).

Other processes include a bromine-based process for converting gaseous alkanes to liquid hydrocarbons. Several basic steps may be used, including (1) reacting bromine with alkanes to produce alkyl bromides and hydrobromic acid (bromination), (2) reacting the alkyl bromide and hydrobromic acid product with a crystalline alumino-silicate catalyst to form higher molecular weight hydrocarbons and hydrobromic acid (coupling), (3) neutralizing the hydrobromic acid by reaction with an aqueous solution of partially oxidized metal bromide salts (as metal oxides/oxybromides/bromides) to produce a metal bromide salt and water in an aqueous solution, or by reaction of the hydrobromic acid with air over a metal bromide catalyst, and (4) regenerating bromine by reaction of the metal bromide salt with oxygen to yield bromine and an oxidized salt. Potential drawbacks of the processes may include low methane conversions; short space-times and the resulting potential for less than 100% bromine conversion; wasteful overbromination of ethane, propane, and higher alkanes, resulting in the formation of dibromomethane and other polybrominated alkanes, which will likely form coke under the disclosed reaction conditions; comparatively low alkyl bromide conversions; the need to separate the hydrocarbon product stream from an aqueous hydrohalic acid stream; and inadequate capture of halogen during the regeneration of the catalyst to remove halogen-containing coke. In addition, the proposed venting of this bromine-containing stream may be both economically and environmentally unacceptable.

The process described above may also requires operation at relatively low temperatures to prevent significant selectivity to methane. One result may be incomplete conversion of alkyl bromide species and, because the process relies on stream splitting to recover products, a considerable amount of unconverted alkyl bromides may leave the process with the products. This represents an unacceptable loss of bromine (as unconverted methyl bromide) and a reduced carbon efficiency.

The neutralization of hydrobromic acid by reaction with an aqueous solution of partially oxidized metal bromide salts and subsequent reaction of the metal bromide salts formed with oxygen to yield bromine and an oxidized salt may also have a number of disadvantages. First, any carbon dioxide present may form carbonates in the slurry, which may not be regenerable. Second, the maximum temperature may be limited due to pressure increases which are intolerable above approximately 200° C., thus preventing complete recovery of halogen. Third, although the use of redox-active metal oxides (e.g., oxides of V, Cr, Mn, Fe, Co, Ce, and Cu) may contribute to molecular bromine formation during the neutralization of hydrobromic acid, incomplete HBr conversion due to the use of a solid bromide salt may in turn result in a significant loss of bromine from the system (in the water phase). Provided an excess of air was used, the bromide salt might eventually be converted to the oxide form, stopping any further loss of HBr in the water discard.

To separate water from bromine, a process may utilize condensation and phase separation to produce semi-dry liquid bromine and a water/bromine mixture. Other means for separating water from bromine, such as using an inert gas to strip the bromine from the water phase or using adsorption-based methods have also been proposed; however, such methods are minimally effective and result in a significant overall loss of halogen.

An oxychlorination process may first remove the water from HCl (a costly step) and then reacts the HCl with oxygen and hydrocarbon directly. Oxychlorination processes rely on the separation of HCl from the unreacted alkanes and higher hydrocarbon products by using water absorption, and subsequent recovery of anhydrous HCl from the aqueous hydrochloric acid. Processes for the absorption of HCl in water may dissapate the heat of absorption by contacting the HCl gas with ambient air, and also by the vaporization of water. Such processes may produce aqueous hydrochloric acid with a concentration of at least 35.5 wt %. Other processes may allow for the recovery of anhydrous HCl gas by extractive distillation using a chloride salt. Still other processes allow for the production of gaseous HCl from dilute aqueous HCl using an amine together with an inert water-immiscible solvent.

Although researchers have made some progress in the search for more efficient CH bond activation pathways for converting natural gas and other hydrocarbon feedstocks into fuels and other products, there remains a tremendous need for a continuous, economically viable, and more efficient process.

SUMMARY

This invention generally relates to carbon-carbon coupling and, more particularly, to methods for converting hydrocarbon feedstocks into useful products.

An embodiment comprises a method comprising: providing a first halogen stream; providing a first alkane stream; reacting at least a portion of the first halogen stream with at least a portion of the first alkane stream in a first reaction vessel to form a first halogenated stream; providing a second alkane stream comprising $C_2$ and higher hydrocarbons; providing a second halogen stream; and reacting at least a portion of the second halogen stream with at least a portion of the second alkane stream in a second reaction vessel to form a second halogenated stream.

Another embodiment comprises a method comprising: providing a halogen stream; providing a first alkane stream; reacting at least a portion of the halogen stream with at least a portion of the first alkane stream to form a halogenated stream, wherein the halogenated stream comprises alkyl monohalides, alkyl polyhalides, and hydrogen halide; and contacting at least some of the alkyl monohalides with a coupling catalyst to form a product stream that comprises higher hydrocarbons and hydrogen halide.

Still another embodiment comprises A method comprising: providing an alkyl halide stream; contacting at least some of the alkyl halides with a coupling catalyst to form a product stream comprising higher hydrocarbons and hydrogen halide; contacting the product stream with an aqueous solution comprising a metal halide to remove at least a portion of the hydrogen halide from the product stream; separating at least some of the metal halide from the aqueous solution; and heating the separated metal halide to generate a corresponding halogen.

The features and advantages of the present invention will be apparent to those skilled in the art. While numerous changes may be made by those skilled in the art, such changes are within the spirit of the invention.

BRIEF DESCRIPTION OF THE DRAWINGS

FIG. 4 is a schematic view of a subprocess for reproportionating polyhalides according to an alternate embodiment of the invention;

FIG. 5 is a schematic view of one embodiment of a continuous process for a halogenation reactor;

FIG. 31 is a graph of bromobenzene conversion and benzene yield as a function of time, for an experiment conducted according to one embodiment of the invention; and FIG. 32 is a graph of catalyst effectiveness as a function of time, for an experiment conducted according to one embodiment of the invention.

DETAILED DESCRIPTION

Figure 1:
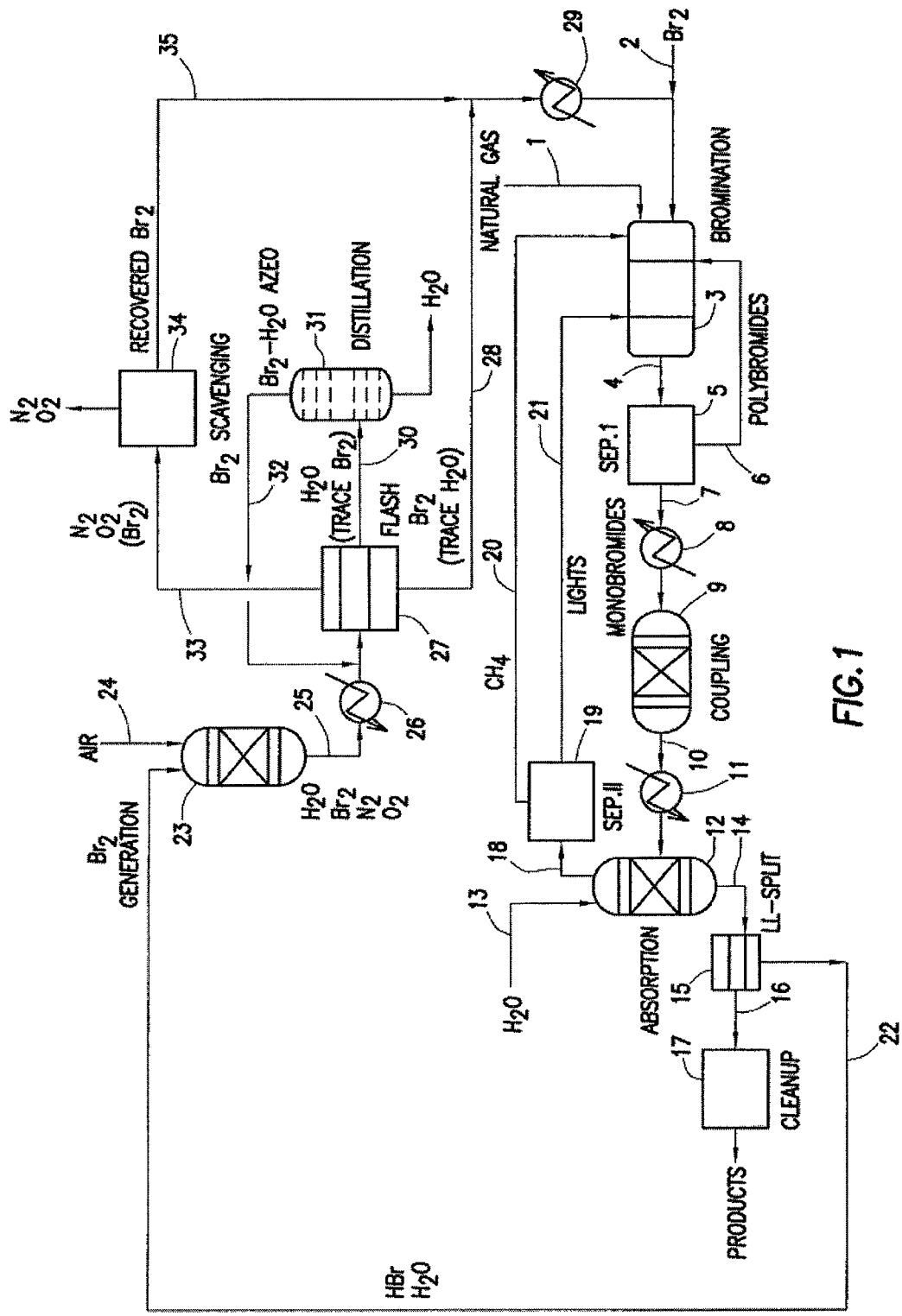
FIG. 1 is a schematic view of one embodiment of a continuous process for converting methane or natural gas into hydrocarbon chemicals according to the invention.

This invention generally relates to carbon-carbon coupling and, more particularly, to methods for converting hydrocarbon feedstocks into useful products.

The present invention provides a chemical process that enables natural gas and other hydrocarbon feedstocks to be converted into higher molecular weight hydrocarbon products, using molecular halogen to activate C—H bonds in the feedstock. According to one aspect of the invention, a continuous process for converting a hydrocarbon feedstock into one or more higher hydrocarbons may comprise the steps of (a) forming alkyl halides by reacting molecular halogen with a hydrocarbon feedstock (preferably a feedstock containing methane), under process conditions sufficient to form alkyl halides and hydrogen halide, whereby substantially all of the molecular halogen is consumed; (b) contacting the reproportionated alkyl halides with a first catalyst under process conditions sufficient to form higher hydrocarbons and additional hydrogen halide; (c) separating the higher hydrocarbons from the hydrogen halide; (d) regenerating molecular halogen under process conditions sufficient to form molecular halogen and water; and (e) repeating steps (a) through (d) a desired number of times. These steps can be carried out in the order presented or, alternatively, in a different order.

In each of the aspects and embodiments of the invention, it is intended that the alkyl halides formed in step (a) can be all the same (e.g., 100% bromomethane) or, more typically, different (e.g., mixtures of bromomethane, dibromomethane, dibromoethane, etc). Similarly, it is contemplated that the "higher hydrocarbons" formed in step (b) can be all the same (e.g., 100% isooctane) or, more typically, different (e.g., mixtures of aliphatic and/or aromatic compounds). As used herein, the term "higher hydrocarbons" refers to hydrocarbons having a greater number of carbon atoms than one or more components of the hydrocarbon feedstock, as well as olefinic hydrocarbons having the same or a greater number of carbon atoms as one or more components of the hydrocarbon feedstock. For instance, if the feedstock is natural gas—typically a mixture of light hydrocarbons, predominately methane, with lesser amounts of ethane, propane, and butane, and even smaller amounts of longer chain hydrocarbons such as pentane, hexane, etc. —the "higher hydrocarbon(s)" produced according to the invention can include a $C_2$ or higher hydrocarbon, such as ethane, propane, butane, $C_{5+}$ hydrocarbons, aromatic hydrocarbons, etc., and optionally ethylene, propylene, and/or longer olefins The term "light hydrocarbons" (sometimes abbreviated "LHCs") refers to $C_1$-$C_4$ hydrocarbons, e.g., methane, ethane, propane, ethylene, propylene, butanes, and butenes, all of which are normally gases at room temperature and atmospheric pressure.

Nonlimiting examples of hydrocarbon feedstocks appropriate for use in the present invention include alkanes, e.g., methane, ethane, propane, and even larger alkanes; olefins; natural gas and other mixtures of hydrocarbons. In most cases, the feedstock will be primarily aliphatic in nature. Certain oil refinery processes yield light hydrocarbon streams (so-called "light-ends," typically a mixture of $C_1$-$C_3$ hydrocarbons), which may be used with or without added methane as the hydrocarbon feedstock in one embodiment of the invention.

Representative halogens include bromine ($Br_2$) and chlorine ($Cl_2$). It is also contemplated that fluorine and iodine may be used, though not necessarily with equivalent results. Some of the problems associated with fluorine may likely be addressed by using dilute streams of fluorine (e.g., fluorine gas carried by helium, nitrogen, or other diluent). It is expected, however, that more vigorous reaction conditions will be required for alkyl fluorides to couple and form higher hydrocarbons, due to the strength of the fluorine-carbon bond. Similarly, problems associated with iodine (such as the endothermic nature of certain iodine reactions) may likely be addressed by carrying out the halogenation and/or coupling reactions at higher temperatures and/or pressures. The use of bromine or chlorine is preferred. While bromine and hydrogen bromide may be used in the descriptions contained herein, it should be understood that chlorine, fluorine, or iodine may be substituted unless otherwise specifically stated.

Figure 2:
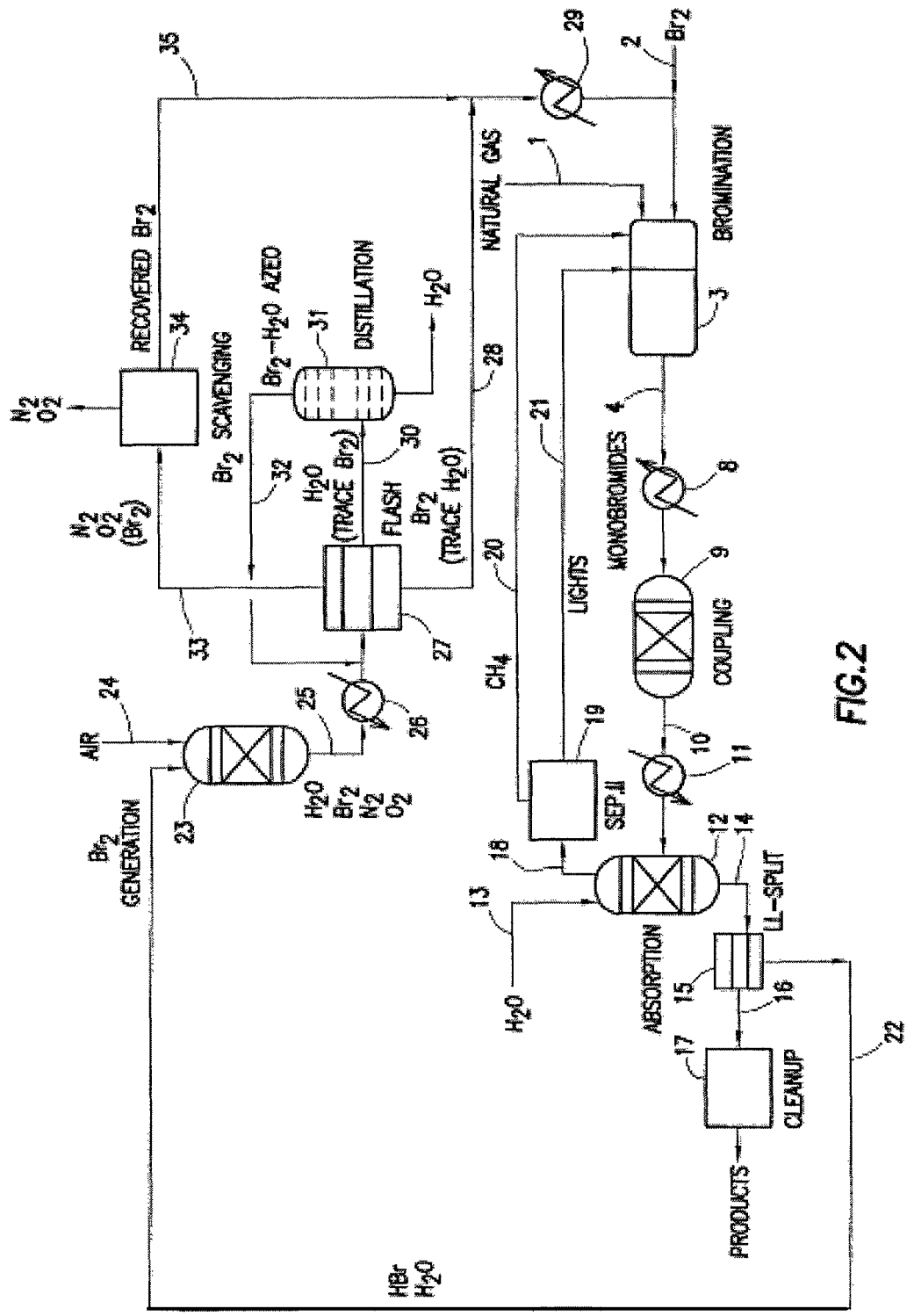
FIG. 2 is a schematic view of one embodiment of a continuous process for converting methane or natural gas into hydrocarbon fuels according to the invention.

FIGS. 1 and 2 schematically illustrate two nonlimiting embodiments of a process according to the invention, with FIG. 1 depicting a process for making hydrocarbon chemicals (e.g., benzene, toluene, xylenes, other aromatic compounds, etc.), and FIG. 2 depicting a process for making fuel-grade hydrocarbons, e.g., hydrocarbons comprising a predominant amount of $C_5$ and higher aliphatic hydrocarbons and (optionally) aromatic hydrocarbons. The primary difference in the two embodiments is that the process depicted in FIG. 2 lacks the first separation unit (SEP I) and does not return polybrominated species to the bromination reactor for "reproportionation." In the scheme shown in FIG. 2, the amount of polybromides produced may be reduced significantly by introducing light gasses into the bromination reactor. The polybromides (from methane bromination) may react with the light gasses to form monobromoalkanes. For convenience, the figures depict a bromine-based process. In alternate embodiments of the invention, however, chlorine or other halogens may be used.

As shown in FIG. 1, natural gas (or another hydrocarbon feedstock) and molecular bromine may be carried by separate lines 1, 2 into a heated bromination reactor 3 and allowed to react. Products (HBr, alkyl bromides, optionally olefins), and possibly unreacted hydrocarbons, exit the reactor and are carried by a line 4 into a first separation unit 5 (SEP I), where monobrominated hydrocarbons and HBr may be separated from polybrominated hydrocarbons. The polybromides may be carried by a line 6 back to the bromination reactor, where they may undergo "reproportionation" with methane and/or other light hydrocarbons, which may be present in the natural gas and/or introduced to the bromination reactor as described below.

Reproportionation of the polybromides formed during the bromination reaction enriches the outlet stream with monobromides and olefinic species, and reduces the amount of polybrominated hydrocarbons that enter the coupling reactor. This, in turn, may reduce the amount of coke that forms during the carbon-carbon coupling reactions. For large scale production of aromatic hydrocarbons, it may be possible to employ additional separation units, which may further purify the feed stream to the coupling reactor by separating and recycling the polybromides, thereby reducing the amount of coke and the overall bromine requirement.

Unreacted hydrocarbon feedstock, HBr, monobromides, and (optionally) olefins formed in the bromination reactor may be carried by a line 7, through a heat exchanger 8, and enter a heated coupling reactor 9, where the monobromides (and, optionally, any olefins present) may react in the presence of a coupling catalyst to form higher hydrocarbons. HBr, higher hydrocarbons, and (possibly) unreacted hydrocarbons and alkyl bromides may exit the coupling reactor and be carried by a line 10, through another heat exchanger 11, and enter an HBr absorption unit 12. Water may be introduced into the unit through a separate line 13. HBr may be absorbed in this unit, which may be a packed column or other gas-liquid contacting device. The effluent, containing liquid hydrocarbons and aqueous HBr, may be carried by a line 14 to a liquid-liquid splitter 15, which phase-separates liquid hydrocarbons from the aqueous HBr stream. The liquid hydrocarbon products may then be carried by a line 16 to a product clean-up unit 17 to yield final hydrocarbon products.

After HBr is separated from the hydrocarbon products and unreacted methane (and any other light hydrocarbons that may be present) in the HBr absorption unit, the methane (and other light hydrocarbons, if any) may be carried by a line 18 into a second separation unit 19 (SEP II), which employs pressure- or temperature-swing absorption, membrane-based separation, cryogenic distillation (preferable for large scale production), or another suitable separation technology. Methane, and possibly other light hydrocarbons, may be returned to the bromination reactor via one or more lines 20, 21. In the embodiment shown, methane may be directed to an upstream region or "zone" of the bromination reactor, while other light hydrocarbons may be directed to a mid- or downstream zone of the reactor (the latter to facilitate reproportionation of polybromides).

The aqueous HBr stream that evolves from the liquid-liquid splitter may be carried by a line 22 to a bromine generation unit 23. Oxygen, air, or oxygen-enriched gas may also be fed into the unit through a separate line 24. Bromine may be regenerated by reacting HBr with oxygen in the presence of a suitable catalyst. The resulting stream may contain water, molecular bromine, oxygen, nitrogen if air was used as the source of oxygen, and possibly other gases. This product stream may be carried by a line 25 through a heat exchanger 26 into a flash vaporization unit 27, which separates most of the molecular bromine from water, oxygen, nitrogen, and other gases (if any) that are present. Molecular bromine, either as a liquid or vapor and containing no more than a trace of $H_2O$, may be carried by a line 28 to a heat exchanger 29, and then returned to the bromination reactor.

Water from the flash vaporization unit containing up to about 3 wt % of molecular bromine may be sent by a line 30 to a distillation unit 31, which yields water as the bottoms stream and bromine or bromine-water azeotrope as a distillate. The distillate may be returned through a line 32 back to the flash vaporization unit.

The gaseous products of the flash vaporization unit (e.g., oxygen, nitrogen, optionally other gases, and no more than a minor or trace amount of bromine) may be carried by a line 33 to a bromine scavenging unit 34, which separates molecular bromine from the other gases. The recovered bromine may then be carried by a line 35 through a heat exchanger 29 and reintroduced into the bromination reactor. The amount of bromine entering the scavenger may be further reduced by increasing the amount of bromine recovered in the flash step by employing brine solutions and direct contact cooling to allow the use of temperatures below 0° C. The other gases (e.g., nitrogen, oxygen) may be vented to the atmosphere.

Figure 3:
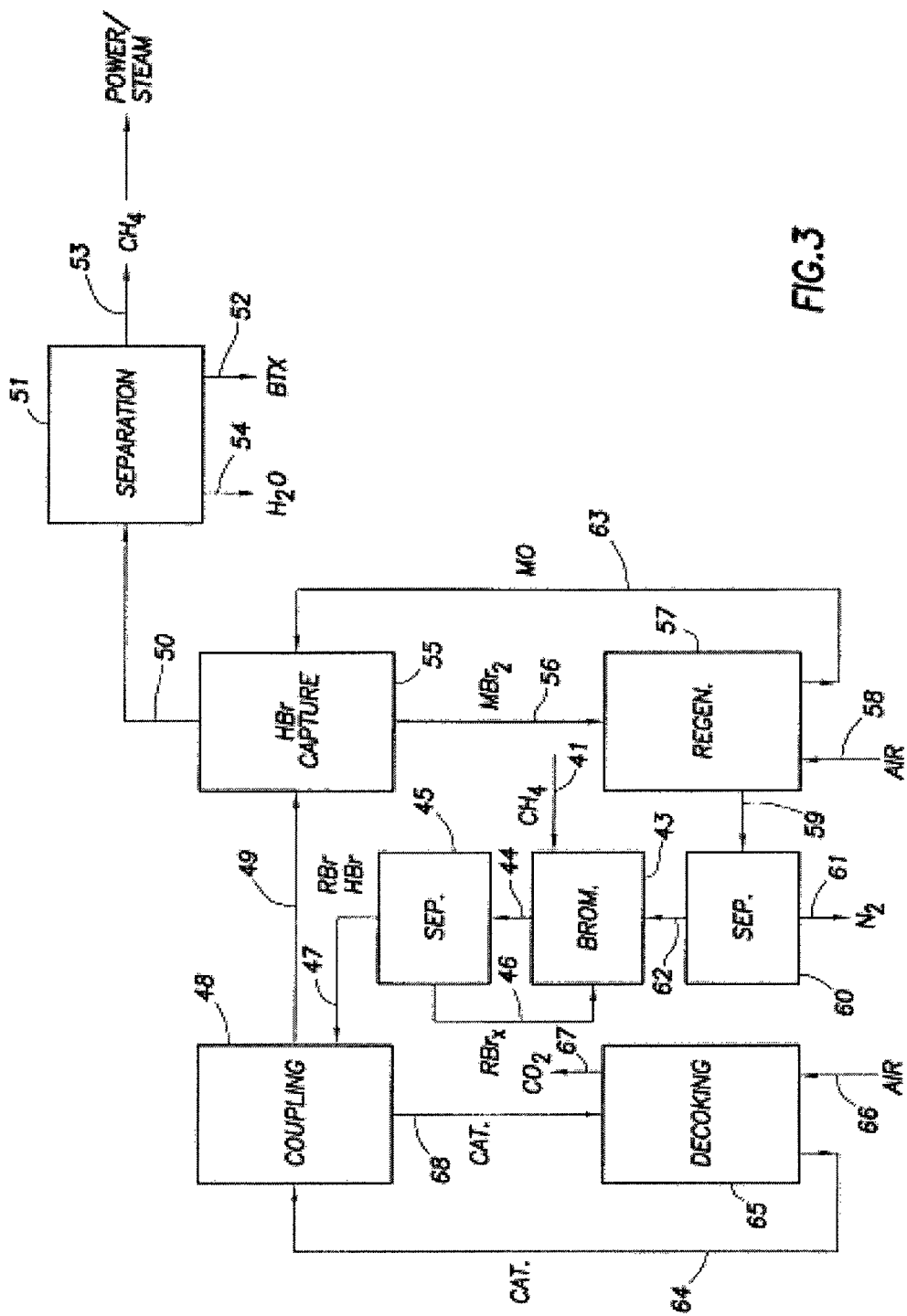
FIG. 3 is a schematic view of one embodiment of a continuous process for converting methane or natural gas into hydrocarbon fuels according to the invention.

In another embodiment, shown in FIG. 3, an HBr capture and oxidation scheme may be used to capture HBr from the products stream without using aqueous absorption and regenerate elemental bromine. In this embodiment, the products stream exiting the coupling reactor 49 may pass through a vessel 55 containing a solid reactant material. The solid reactant may react with the HBr to form a corresponding metal bromide and water, which may pass through the vessel along with the unaffected hydrocarbon products from the coupling reactor. The metal bromide 56 may then be contacted with air or oxygen 58 to regenerate the original solid reactant material 63 and an elemental bromine stream 59, which can be recycled for use in the bromination reactor 43.

Various embodiments and features of individual subprocesses and other improvements for carrying out the invention will now be described in more detail.

Bromination

Bromination of the hydrocarbon feedstock may be carried out in a fixed bed, fluidized bed, or other suitable reactor, at a temperature and pressure such that the bromination products and reactants are gases, for example, about 1 to about 50 atm, about 150° C. to about 600° C., more preferably about 400° C. to about 600° C., even more preferably, about 450° C. to about 515° C., with a residence time of about 1 to about 60 seconds, more preferably about 1 to about 15 seconds. Higher temperatures tend to favor coke formation, while low temperatures require larger reactors. Using a fluidized bed may offer the advantage of improved heat transfer.

Alkane bromination may be initiated using heat or light, with thermal means being preferred. In one embodiment, the reactor may also contain a halogenation catalyst, such as a zeolite, amorphous alumino-silicate, acidic zirconia, tungstates, solid phosphoric acids, metal oxides, mixed metal oxides, metal halides, mixed metal halides (the metal in such cases being, e.g., nickel, copper, cerium, cobalt, etc.), and/or or other catalysts as described, e.g., in U.S. Pat. Nos. 3,935,289 and 4,971,664, which are incorporated herein in their entirety. In an alternate embodiment, the reactor contains a porous or non-porous inert material that provides sufficient surface area to retain coke formed in the reactor and prevent it from escaping. The inert material may also promote the formation of polyhalogenated hydrocarbons, such as tribromopropane. In still another embodiment, both a catalyst and an inert material are provided in the reactor. Optionally, the reactor may contain different regions or zones to allow, in one or more zones, complete conversion of molecular bromine to produce alkyl bromides and hydrogen bromide.

The bromination reaction may also be carried out in the presence of an isomerization catalyst, such as a metal bromide (e.g., NaBr, KBr, CuBr, NiBr$_2$, MgBr$_2$, CaBr$_2$,), metal oxide (e.g., SiO$_2$, ZrO$_2$, Al$_2$O$_3$,), or metal (Pt, Pd, Ru, Ir, Rh) to help generate the desired brominated isomer(s). Since isomerization and bromination conditions are similar, the bromination and isomerization may be carried out in the same reactor vessel. Alternatively, a separate isomerization reactor may be utilized, located downstream of the bromination reactor and upstream of the coupling reactor.

In an embodiment, a separate bromination reactor may be used to brominate a light hydrocarbon stream. Light hydrocarbon bromination of C$_1$-C$_5$ alkanes with bromine may occur at temperatures ranging from about 150° C. to about 550° C., with the optimal temperature depending on the alkanes that are present and being brominated. In some embodiments, a polybrominated methane stream from an alkyl polybromide separator may be used to brominate the light hydrocarbon stream in the separate bromination reactor. Light hydrocarbon bromination may proceed more quickly at elevated pressures (e.g., about 2 bar to about 30 bar). Polybromides produced during lights bromination may be reproportionated to monobromides by allowing longer residence times. Polybromides of C$_2$-C$_5$ alkanes may react better and produce less coke in the coupling reactor than the C$_1$ polybromides.

Reproportionation

In some embodiments, a key feature of the invention is the "reproportionation" of polyhalogenated hydrocarbons (polyhalides), i.e., halogenated hydrocarbons containing two or more halogen atoms per molecule. Monohalogenated alkanes (monohalides) created during the halogenation reaction may be desirable as predominant reactant species for subsequent coupling reactions and formation of higher molecular weight hydrocarbons. For certain product selectivities, polyhalogenated alkanes may be desirable. Reproportionation allows a desired enrichment of monohalides to be achieved by reacting polyhalogenated alkyl halides with nonhalogenated alkanes, generally in the substantial absence of molecular halogens, to control the ratio of mono-to-polyhalogenated species. For example, dibromomethane may be reacted with methane to produce methyl bromide; dibromomethane may be reacted with propane to produce methyl bromide and propyl bromide and/or propylene; and so forth.

Reactive reproportionation may be accomplished by allowing the hydrocarbon feedstock and/or recycled alkanes to react with polyhalogenated species from the halogenation reactor, preferably in the substantial absence of molecular halogen. As a practical matter, substantially all of the molecular halogen entering the halogenation reactor is quickly consumed, forming mono- and polyhalides; therefore reproportionation of higher bromides may be accomplished simply by introducing polybromides into a mid- or downstream region or "zone" of the halogenation reactor, optionally heated to a temperature that differs from the temperature of the rest of the reactor.

Alternatively, reproportionation may be carried out in a separate "reproportionation reactor," where polyhalides and unhalogenated alkanes are allowed to react, preferably in the substantial absence of molecular halogen. FIG. 4 illustrates one such embodiment where, for clarity, only significant system elements are shown. As in FIG. 1, natural gas or another hydrocarbon feedstock and molecular bromine may be carried by separate lines 1, 2 to a heated bromination reactor 3 and allowed to react. Products (e.g., HBr, alkyl bromides) and possibly unreacted hydrocarbons, may exit the reactor and be carried by a line 4 into a first separation unit 5, where monobrominated hydrocarbons and HBr are separated from polybrominated hydrocarbons. The monobromides, HBr, and possibly unreacted hydrocarbons may be carried by a line 7, through a heat exchanger 8, to a coupling reactor 9, and allowed to react, as shown in FIG. 1. The polybromides may be carried by a line 6 to a reproportionation reactor 36. Additional natural gas or other alkane feedstock may also be introduced into the reproportionation reactor, via a line 37. Polybromides may react with unbrominated alkanes in the reproportionation reactor to form monobromides, which may be carried by a line 38 to the coupling reactor 9, after first passing through a heat exchanger.

In another embodiment of the invention (not shown), where the hydrocarbon feedstock comprises natural gas containing a considerable amount of C$_2$ and higher hydrocarbons, the "fresh" natural gas feed is introduced directly into the reproportionation reactor, and recycled methane (which passes through the reproportionation reactor unconverted) is carried back into the halogenation reactor.

Reproportionation may be thermally driven and/or facilitated by use of a catalyst. Nonlimiting examples of suitable catalysts include metal oxides, metal halides, and zeolites. U.S. Pat. No. 4,654,449, incorporated herein in its entirety, discloses the reproportionation of polyhalogenated alkanes with alkanes using an acidic zeolite catalyst. U.S. Pat. Nos. 2,979,541 and 3,026,361 disclose the use of carbon tetrachloride as a chlorinating agent for methane, ethane, propane and their chlorinated analogues. All three patents are incorporated by reference herein in their entirety.

Reproportionation of C$_1$-C$_5$ alkanes with dibromomethane and/or other polybromides may occur at temperatures ranging from about 350° C. to about 550° C., with the optimal temperature depending on the polybromide(s) that are present and the alkane(s) being brominated. In addition, reproportionation may proceed more quickly at elevated pressures (e.g., about 2 bar to about 30 bar). By achieving a high initial methane conversion in the halogenation reactor, substantial amounts of di- and tribromomethane may be created; those species may then be used as bromination reagents in the reproportionation step. Using di- and tribromomethane may allow for controlled bromination of C$_1$-C$_5$ alkanes to monobrominated C$_1$-C$_5$ bromoalkanes and C$_2$-C$_5$ olefins. Reproportionation of di- and tribromomethane may facilitate high initial methane conversion during bromination, which may reduce the methane recycle flow rate and enrich the reactant gas stream with C$_2$-C$_5$ monobromoalkanes and olefins that couple to liquid products over a variety of catalysts, including zeolites.

In another embodiment of the invention, reproportionation may be carried out without first separating the polyhalides in a separation unit. This may be facilitated by packing the "reproportionation zone" with a catalyst, such as a zeolite, that allows the reaction to occur at a reduced temperature. For example, although propane reacts with dibromomethane to form bromomethane and bromopropane (an example of "reproportionation"), the reaction does not occur at an appreciable rate at temperatures below about 500° C. The use of a zeolite may allow reproportionation to occur at a reduced temperature, enabling species such as methane and ethane to be brominated in one zone of the reactor, and di-, tri-, and other polybromides to be reproportionated in another zone of the reactor.

Bromine Recovery During Decoking

Inevitably, coke formation will occur in the halogenation and reproportionation processes. If catalysts are used in the reactor(s) or reactor zone(s), the catalysts may be deactivated by the coke; therefore, periodic removal of the carbonaceous deposits may be required. In addition, we have discovered that, within the coke that is formed, bromine may also be found, and it is highly desirable that this bromine be recovered in order to minimize loss of bromine in the overall process, which is important for both economic and environmental reasons.

Several forms of bromides may be present: HBr, organic bromides such as methyl bromide and dibromomethane, and molecular bromine. The invention provides means for recovering this bromine from the decoking process. In one embodiment, a given reactor may be switched off-line and air or oxygen may be introduced to combust the carbon deposits and produce HBr from the residual bromine residues. The effluent gas may be added to the air (or oxygen) reactant stream fed to the bromine generation reactor, thereby facilitating complete bromine recovery. This process may be repeated periodically. In another embodiment, a given reactor may remains operational and bromination and decoking occur simultaneously in the same reactor.

In an embodiment while a given reactor is off-line, the overall process can, nevertheless, be operated without interruption by using a reserve reactor, which may be arranged in parallel with its counterpart reactor. For example, twin bromination reactors and twin coupling reactors may be utilized, with process gasses being diverted away from one, but not both, bromination reactors (or coupling reactors) when a decoking operation is desired. The use of a fluidized bed may reduce coke formation and facilitate the removal of heat and catalyst regeneration.

Another embodiment of the decoking process may involve non-oxidative decoking using an alkane or mixture of alkanes, which may reduce both the loss of adsorbed products and the oxygen requirement of the process.

In still another embodiment of the decoking process, an oxidant such as oxygen, air, or enriched air may be co-fed into the bromination section to convert the coke into carbon dioxide and/or carbon monoxide during the bromination reaction, thus eliminating or reducing the off-line decoking requirement. The reactor configuration may comprise a catalytic bed for the bromination of hydrocarbons followed by a metal bromide bed to capture any unreacted oxygen.

In the embodiment shown in FIG. 5, a bromination reactor capable of being decoked during operation may comprise one or more catalytic zones useful for the bromination of a hydrocarbon with a metal halide catalyst zone located near the center of the reactor. As a hydrocarbon and an elemental halide are introduced into the reactor, the halide may react with the hydrocarbon to form an alkyl halide and some coke on the halogenation catalyst. The oxygen present in the feed to the reactor may react with any coke formed during the halogenation of the hydrocarbons to produce oxidation products (e.g., CO, $CO_2$, water, etc.). In addition, the oxygen may react with a portion of the hydrocarbons or halogenated hydrocarbons to form oxidation products. Any oxygen reaching the metal halide catalyst zone may react with the metal halide to form a metal oxide and elemental halogen. This halogen may then further react with any unreacted hydrocarbons to form alkyl halides. The reactor may be cyclically operated in a forward and reverse mode to remove coke buildup on any catalyst present in either side of the metal halide zone. The reactor may be a fixed bed reactor, including a vertical fixed bed reactor, a radial bed reactor, or any other suitable fixed bed type reactor.

Appropriate catalyst types for the metal bromide zone may include any active catalyst or solid reactant useful in capturing oxygen and forming an elemental halide, as described in more detail below. The active materials may be either redox active or non-redox active. Suitable materials may include, but are not limited to, oxides or halides of copper, magnesium, yttrium, nickel, cobalt, iron, calcium, vanadium, molybdenum, chromium, manganese, zinc, lanthanum, tungsten, tin, indium, bismuth, or combinations thereof. An oxide of these metals may form a metal halide in situ upon exposure to any hydrogen halide generated during the halogenation reaction. In an embodiment, a non-redox active catalyst such as $NiO/NiBr_2$ may be preferred due to its high bromine capacity and stability at high temperature in the reactor. In an embodiment, a $NiBr_2$ catalyst may be used in the center of the reactor. This bromination configuration can prevent oxygen break through where $Br_2$ is generated from a metal bromide (e.g., $CuBr_2$) for use in the bromination reaction, including use at high pressures. The oxygen flowrate through the reactor may be less than about 5% by volume, or alternatively, less than about 3% by volume during the decoking process. Further, the decoking process may occur periodically to oxidize any built-up coke deposits, or oxygen may be continuously fed to the reactor in a continuous decoking process.

Alkyl Halide Separation

The presence of large concentrations of polyhalogenated species in the feed to the coupling reactor may result in an increase in coke formation. In many applications, such as the production of aromatics and light olefins, it may be desirable to feed only monohalides to the coupling reactor to improve the conversion to products. In one embodiment of the invention, a specific separation step may be added between the halogenation/reproportionation reactor(s) and the coupling reactor.

For example, a distillation column and associated heat exchangers may be used to separate the monobromides from the polybrominated species by utilizing the large difference in boiling points of the compounds. The polybrominated species that are recovered as the bottoms stream may be reproportionated with alkanes to form monobromide species and olefins, either in the bromination reactor or in a separate reproportionation reactor. The distillation column may be operated at any pressure ranging from about 1 atm to about 50 atm. The higher pressures may allow higher condenser temperatures to be used, thereby reducing the refrigeration requirement.

Figure 6:
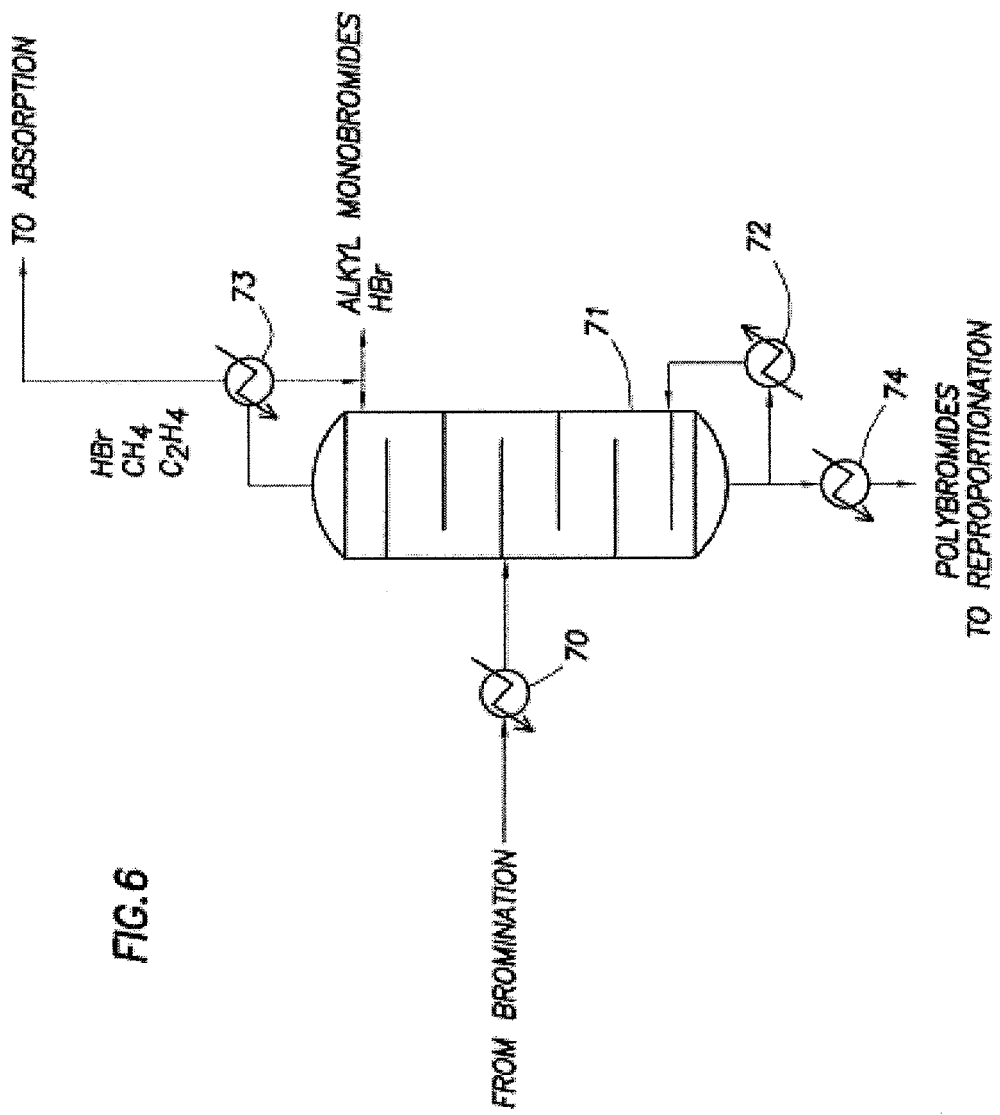
FIG. 6 is a schematic view of one embodiment of a monobromide separation column, for use in the practice of the invention.

FIG. 6 illustrates one embodiment of a separation unit for separating monobromides from polybrominated species. Alkyl bromides from the bromination reactor may be cooled by passing through a heat exchanger 70, and then provided to a distillation column 71 equipped with two heat exchangers 72 and 73. At the bottom of the column, heat exchanger 72 acts as a reboiler, while at the top of the column heat exchanger 73 acts as a partial condenser. This configuration allows a liquid "bottoms" enriched in polybromides (and containing no more than a minor amount of monobromides) to be withdrawn from the distillation column. The polybromides may be passed through another heat exchanger 74 to convert them back to a gas before they are returned to the bromination reactor (or sent to a separate reproportionation reactor) for reproportionation with unbrominated alkanes. At the top of the column, partial reflux of the liquid from the reflux drum is facilitated by the heat exchanger 73, yielding a vapor enriched in lighter components including methane and HBr, and a liquid stream comprised of monobromides and HBr (and containing no more than a minor amount of polybromides).

Alternate distillation configurations may include a side stream column with and without a side stream rectifier or stripper. If the feed from the bromination reactor contains water, the bottoms stream from the distillation column will also contain water, and a liquid-liquid phase split on the bottoms stream may be used to separate water from the polybrominated species. Due to the presence of HBr in the water stream, it may be sent to a HBr absorption column or to the bromine generation reactor.

Catalytic Coupling of Alkyl Halides to Higher Molecular Weight Products

The alkyl halides produced in the halogenation/reproportionation step may be reacted over a catalyst to produce higher hydrocarbons and hydrogen halide. The reactant feed may also contain hydrogen halide and unhalogenated alkanes from the bromination reactor. According to the invention, any of a number of catalysts may be used to facilitate the formation of higher hydrocarbon products from halogenated hydrocarbons. Nonlimiting examples include non-crystalline alumino silicates (amorphous solid acids), tungsten/zirconia super acids, sulfated zirconia, zeolites, such as SAPO-34 and its framework-substituted analogues (substituted with, e.g., Ni or Mn), ZSM-5 and its ion-exchanged analogs, and framework substituted ZSM-5 (substituted with Ti, Fe, Ti+Fe, B, or Ga). Preferred catalysts for producing liquid-at-room-temperature hydrocarbons include ion-exchanged ZSM-5 having a $SiO_2/Al_2O_3$ ratio below about 300, preferably below about 100, and most preferably about 30 or less. Nonlimiting examples of preferred exchanged ions include ions of Ag, Ba, Bi, Ca, Fe, Li, Mg, Sr, K, Na, Rb, Mn, Co, Ni, Cu, Ru, Pb, Pd, Pt, and Ce. These ions can be exchanged as pure salts or as mixtures of salts. The preparation of doped zeolites and their use as carbon-carbon coupling catalysts is described in Patent Publication No. US 2005/0171393 A1, which is incorporated by reference herein in its entirety. In another embodiment, a fluorinated alumina based solid reactant, as described in more detail below, may be used as the catalyst or as a support for a catalytic material useful in the formation of higher hydrocarbon products. Use of a fluorinated alumina may allow for the simultaneous formation of higher hydrocarbons and capture of hydrogen halide formed in the reaction.

In one embodiment of the invention a Mn-exchanged ZSM-5 zeolite having a $SiO_2/Al_2O_3$ ratio of 30 is used as the coupling catalyst. Under certain process conditions, it can produce a tailored selectivity of liquid hydrocarbon products.

In one embodiment of the invention, a reduced aluminum content ZSM-5 zeolite may be used as a coupling catalyst. Generally, a dealumination treatment of the coupling catalyst may provide benefits such as higher selectivity towards BTX products while maintaining high conversion (>about 99%). Additionally dealumination may extended the catalyst useful life, may improve short and long term thermal stability, and may also reduce coke generation. Dealumination of a zeolite catalyst may be done by selective treatment of the hydrogen-exchanged zeolite with a compound that specifically reacts with aluminum centers by forming either volatile compounds at high temperature or soluble complexes when treated in an aqueous solution. Examples of dealumination agents may include mineral acids, such as hydrochloric acid (HCl), hydrofluoric acid (HF), ethylenediaminetetraacetic acid (EDTA), oxalic acid, malonic acid; overheated water steam (steaming), and exchange reagents ($SiCl_4$, $NH_4[SiF_6]$, $NH_4HF_2$, $AlF_3$, trialkyl phosphates, organic phosphites).

Coupling of haloalkanes may be carried out in a fixed bed, fluidized bed, or other suitable reactor, at a suitable temperature (e.g., about 150° C. to about 600° C., preferably about 275° C. to about 425° C.) and pressure (e.g., about 0.1 atm to about 35 atm) and a residence time ($\tau$) of from about 1 second to about 45 seconds. In general, a relatively long residence time favors conversion of reactants to products, as well as product selectivity, while a short residence time means higher throughput and (possibly) improved economics. It is possible to direct product selectivity by changing the catalyst, altering the reaction temperature, and/or altering the residence time in the reactor. For example, at a moderate residence time of 10 seconds and a moderate temperature of about 350° C., xylene and mesitylenes may be the predominant components of the aromatic fraction (benzene+toluene+xylenes+mesitylenes; "BTXM") produced when the product of a methane bromination reaction is fed into a coupling reactor packed with a metal-ion-impregnated ZSM-5 catalyst, where the impregnation metal is Ag, Ba, Bi, Ca, Co, Cu, Fe, La, Li, Mg, Mn, Ni, Pb, Pd, or Sr, and the ZSM-5 catalyst is Zeolyst CBV 58, 2314, 3024, 5524, or 8014, (available from Zeolyst International, Valley Forge, Pa.). At a reaction temperature of about 425° C. and a residence time of about 40 seconds, toluene and benzene may be the predominant products of the BTXM fraction. Product selectivity may also be varied by controlling the concentration of dibromomethane produced or fed into the coupling reactor. Removal of reaction heat and continuous decoking and catalyst regeneration using a fluidized bed reactor configuration for the coupling reactor may be anticipated in some facilities.

In an embodiment, the coupling reaction may be carried out in a pair of coupling reactors, arranged in parallel. This allows the overall process to be run continuously, without interruption, even if one of the coupling reactors is taken off line for decoking or for some other reason. Similar redundancies can be utilized in the bromination, product separation, halogen generation, and other units used in the overall process.

Figure 8:
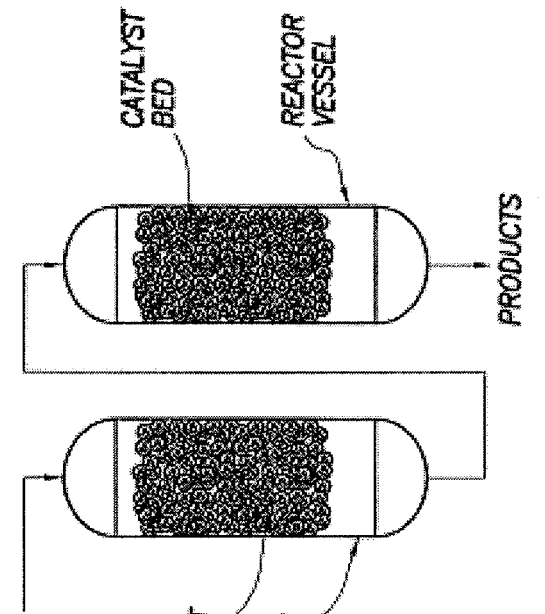
FIG. 8 is another schematic view of one embodiment of a catalytic coupling reactor with multiple catalytic beds.
Figure 7:
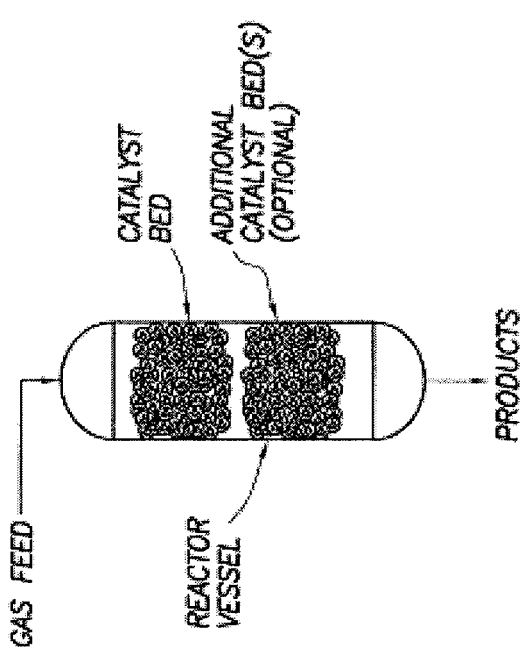
FIG. 7 is a schematic view of one embodiment of a catalytic coupling reactor with multiple catalytic beds.

In some embodiments, the catalytic coupling of alkyl halides to higher molecular weight products may result in the formation of olefins. In these embodiments, the alkyl halides produced in the halogenation/reproportionation step may be reacted over a catalyst to produce higher hydrocarbons and hydrogen halide. The reactant feed may also contain hydrogen halide and unhalogenated alkanes from the bromination reactor. In one embodiment, the coupling reactions take place in a single coupling vessel with a single catalyst system as shown in FIG. 7. In another embodiment two or more catalyst systems are used, each in its own reactor. FIG. 8 illustrates this for two catalyst systems, although more may be used. In another embodiment of the invention (not illustrated), two or more catalysts may be mixed together using a single reaction vessel. For convenience, the drawings illustrate fixed bed reactors. In other embodiments of the invention, the reactor systems may use fixed bed, moving bed, fluidized bed, or any other suitable reactors or combinations of these reactors types.

According to the invention, any of a number of catalysts or a combination of two or three of these catalysts may be used to facilitate the formation of light olefins from halogenated hydrocarbons. Nonlimiting examples include various crystalline silico-alumino-phosphates and alumino silicates, such as SAPO-34 and its framework-substituted analogues (substituted with, e.g., Co, Ni, Mn, Ga or Fe), ZSM-5 and its metal doped analogs (doped with Mg, Ca, Sr, Ba, K, Ag, P, La, or Zn), erionite, ferrierite, ALPO-5, MAPO-36, ZSM-12, ZSM-57, ZSM-23, ZSM-22 and MCM-22. Catalysts for producing light olefins may include SAPO-34, CoSAPO-34 (Co substituted SAPO-34), alkaline earth metal doped ZSM-5 having a loading amount below about 20% in weight, preferably in the range of about 0.5% to about 10%. The synthesis and preparation procedures for these materials are described in the Examples herein.

Coupling of alkyl halides to olefins may be carried out in a fixed bed, moving bed, fluidized bed, or any other suitable reactor, at a suitable temperature (e.g., about 300° C. to about 600° C., preferably about 400° C. to about 500° C.) and pressure (e.g., about 0.1 atm to about 10 atm.) and a residence time ($\tau$) of from about 0.1 seconds to about 10 seconds. In general, a relatively short residence time may favor conversion of reactants to desired products, as well as improving product selectivity. It may be possible to direct product selectivity by changing the catalyst, altering the reaction temperature, and/or altering the residence time in the reactor. For example, with a ZSM-5 based catalyst (e.g. 5% Mg/8014), at a short residence time (<1 s) and moderate temperature (about 400° C.), propylene is the predominant component of light olefins. With a SAPO-34, at a reaction temperature higher than 450° C., ethylene is the predominant component of the light olefins. Removal of reaction heat and continuous decoking and catalyst regeneration using a fluidized bed reactor configuration for the coupling reactor may be anticipated in some embodiments of the invention.

In other embodiments, the catalytic coupling of alkyl halides to higher molecular weight products may result in the formation of alcohols or oxygenates. In an embodiment, the resulting MeBr may be reacted over a suitable catalyst (e.g., Ca silicate as described in more detail herein) to form alcohols or other oxygenates, generating HBr and $H_2O$ in the process.

In another embodiment, the formation of oxygenates may take place in a single reaction vessel. In this embodiment an aqueous solution of $SeO_2$ may be used to form alcohols and/ or other oxygenates. The use of an aqueous $SeO_2$ solution is described in more detail below.

In some embodiments, the catalytic coupling of alkyl halides to higher molecular weight products may result in the formation of aromatic compounds such as mesitylene. In one embodiment, a suitable catalyst to form mesitylene may be a modified ZSM-5 catalyst. One example of a suitable modified ZSM-5 catalyst may be a copper oxide (CuO)/zinc oxide (ZnO) modified ZSM-5 catalyst synthesized using a wet-impregnation technique.

One example of a suitable wet-impregnation technique may include using a metal nitrate solution to coat a catalyst support followed by calcining. For example, copper nitrate and zinc nitrate may be dissolved in de-ionized water to form a solution. If necessary, the pH value of the solution may be adjusted by adding a base, such as ammonium hydroxide. A ZSM-5 zeolite catalyst may then be added to the solution and allowed to soak. In some embodiments, the catalyst may soak in the solution for about 24 hours. After the catalyst has been soaked in solution, the excess water may be removed under vacuum and the catalyst may be dried and calcined. The material may be heated to between about 100° C. and about 150° C. for about 12 hours to remove at least some water. The dried material may then be calcinated at about 450° C. to about 850° C. for about 6 hours using a heating rate of about 1° C./min. One example of a suitable modified ZSM-5 catalyst is an about 7% CuO/0.5% ZnO impregnated ZSM-5 catalyst with a silica to aluminum ratio of about 55.

Reduction of Coke in the Catalytic Coupling Reaction

As previously noted, the process of producing higher hydrocarbons using alkyl halides may generates coke (a carbon rich solid residue) as an undesired byproduct on the catalyst and reactor walls. Furthermore, it may reduce productivity due to the need for de-coking on a regular basis. In some embodiments, a Lewis base molecule, such as water, carbon dioxide and carbon monoxide, may be added to the catalyst to reduce the amount of coke that is generated. It is believed that the Lewis base molecule, such as water, reacts with the most reactive carbocations on the surface of the catalyst preventing the elimination of hydrogen rich fragments and consecutive conversion to coke. In addition, the Lewis base molecule may react with the Lewis acidic sites on the catalyst, thereby preventing them from generating coke. In some embodiments, it may be desirable to continuously supply Lewis base molecules as the adsorption of the Lewis base on the catalytic acidic centers is reversible at the conditions of the reaction. In an embodiment, less than about 15%, or alternatively less than about 10% by weight of the Lewis base may be added to control the formation of coke.

Hydrocarbon Product Separation and Halogen Recovery

The coupling products may include higher hydrocarbons and HBr. In the embodiments shown in FIGS. 1 and 2, products that exit the coupling reactor may first be cooled in a heat exchanger and then sent to an absorption column. HBr may be absorbed in water using a packed column or other contacting device. Input water and the product stream may be contacted either in a co-current or counter-current flow, with the counter-current flow preferred for its improved efficiency. HBr absorption may be carried out either substantially adiabatically or substantially isothermally. In one embodiment, the concentration of hydrobromic acid after absorption ranges from 5 to 70 wt %, with a preferred range of 20 to 50 wt %. The operating pressure may range from about 1 atm to about 50 atm, more preferably from about 1 atm to about 30 atm. In the laboratory, a glass column or glass-lined column with ceramic or glass packing may be used. In a pilot or commercial plant, one or more durable, corrosion-resistant materials, as described in more detail below, may be utilized.

In one embodiment of the invention, the hydrocarbon products may be recovered as a liquid from the HBr absorption column. This liquid hydrocarbon stream may be phase-separated from the aqueous HBr stream using a liquid-liquid splitter and sent to the product cleanup unit. In another embodiment, the hydrocarbon products are recovered from the HBr column as a gas stream, together with the unconverted methane and other light gases. The products may then be separated and recovered from the methane and light gases using any of a number of techniques. Nonlimiting examples include distillation, pressure swing adsorption, and membrane separation technologies.

In some embodiments, the product clean-up unit may comprises or include a reactor for converting halogenated hydrocarbons present in the product stream into unhalogenated hydrocarbons. For example, under certain conditions, small amounts of $C_1$-$C_4$ bromoalkanes, bromobenzene, and/or other brominated species may be formed and pass from the coupling reactor to the liquid-liquid splitter 15 and then to the product clean-up unit 17 as shown in FIG. 1. These brominated species may be "hydrodehalogenated" in a suitable reactor. In one embodiment, such a reactor comprises a continuous fixed bed, catalytic converter packed with a supported metal or metal oxide catalyst. Nonlimiting examples of the active component may include copper, copper oxide, palladium, and platinum, with palladium being preferred. Nonlimiting examples of support materials include active carbon, alumina, silica, and zeolites, with alumina being preferred. The reactor may be operated at a pressure of about 0 psi to about 150 psi, preferably from about 0 psi to about 5 psi, and a temperature of about 250° C. to about 400° C., preferably about 300° C. to about 350° C., with a GHSV of about 1200 hr$^{-1}$ to about 60 hr$^{-1}$, preferably about 240 hr$^{-1}$. When bromobenzene (e.g.) is passed over such a reactor, it is readily converted to benzene and HBr, with some light hydrocarbons (e.g., $C_3$-$C_7$) produced as byproducts. Although carbon deposition (coking) may deactivate the catalyst, the catalyst may be regenerated by exposure to oxygen and then hydrogen at, e.g., 500° C. and 400° C., respectively.

After HBr is separated from the hydrocarbon products, the unconverted methane may leave with the light gases in the vapor outlet of the HBr absorption unit. In one embodiment of the invention, unconverted methane may be separated from the light gases in a separation unit ("SEP II" in the FIGS.), which operates using pressure or temperature swing adsorption, membrane-based separation, cryogenic distillation (preferable for large-scale production), or some other suitable separation process. Low methane conversions in the bromination reactor may result in the coupling products being carried with the light gases, which in turn may necessitate the recovery of these species from the lights gases. Separation technologies that may be employed for this purpose include, but are not limited to, distillation, pressure or temperature swing adsorption, and membrane-based technologies.

Figure 9:
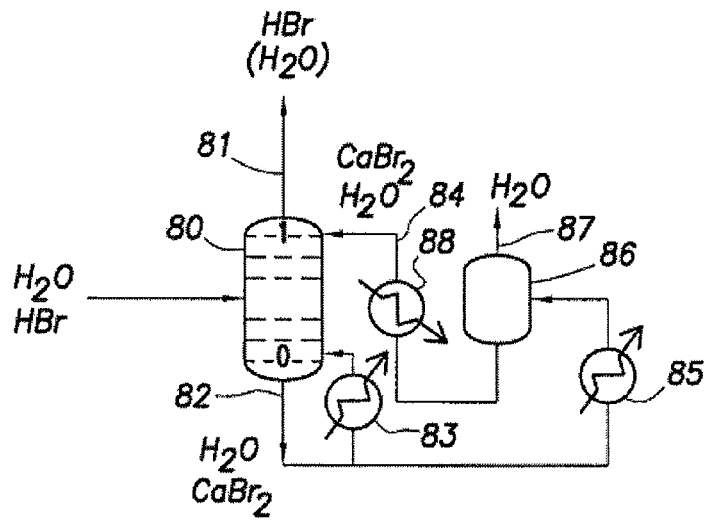
FIG. 9 is a schematic view of one embodiment of an extractive distillation system, for use in the practice of the invention.

In another aspect of the invention, a process for separating anhydrous HBr from an aqueous solution of HBr is provided. HBr forms a high-boiling azeotrope with water; therefore, separation of HBr from the aqueous solution requires either breaking the azeotrope using an extractive agent or bypassing the azeotrope using pressure swing distillation. FIG. 9 illustrates one embodiment of an extractive distillation unit for separating HBr from water. Water may be extracted in a distillation column 80 and HBr may be obtained as the distillate stream 81. The distillate stream may also contain small amounts of water. In one embodiment, the distillation column 80 is a tray-tower or a packed column. Conventional ceramic packing may be preferred over structured packing. Aqueous bromide salt, such as $CaBr_2$, may be added at the top of the distillation column, resulting in the extraction of water from aqueous HBr. A condenser may not be required for the column. A reboiler 83 may be used to maintain the vapor flow in the distillation column. The diluted stream of aqueous $CaBr_2$ 82 may be sent to the evaporation section 86, which, optionally has a trayed or packed section. The bottoms stream from the column may be heated before entering the evaporation section. Stream 87 may comprise mostly water (and no more than traces of HBr) and may leave the evaporation section.

In one embodiment, HBr may be displaced as a gas from its aqueous solution in the presence of an electrolyte that shares a common ion (Br$^-$ or H$^+$) or an ion (e.g. $Ca^{2+}$ or $SO_4^{2-}$) that has a higher hydration energy than HBr. The presence of the electrolyte pushes the equilibrium $HBr_{aq} \leftrightarrow HBr_{gas}$ towards gas evolution, which may be further facilitated by heating the solution.

Aqueous solutions of metal bromides such as $CaBr_2$, $MgBr_2$ also KBr, NaBr, LiBr, RbBr, CsBr, $SrBr_2$, $BaBr_2$, $MnBr_2$, $FeBr_2$, $FeBr_3$, $CoBr_2$, $NiBr_2$, $CuBr_2$, $ZnBr_2$, $CdBr_2$, $AlBr_3$, $LaBr_3$, $YBr_3$, and $BiBr_3$ may be used as extractive agents, with aqueous solutions of $CaBr_2$, $MgBr_2$, KBr, NaBr, LiBr or mixtures thereof being preferred. The bottoms stream of the distillation column may contain a diluted solution of the extracting agent. This stream may be sent to another distillation column or a vaporizer where water may be evaporated and the extracting agent may be concentrated before sending it back to the extractive distillation column. Sulfuric acid may be used as an extracting agent if its reaction with HBr to form bromine and sulfur dioxide may be minimized. Experiments carried out to demonstrate the separation of anhydrous HBr from an aqueous solution of HBr are described in Examples 2 and 3.

Figure 10:
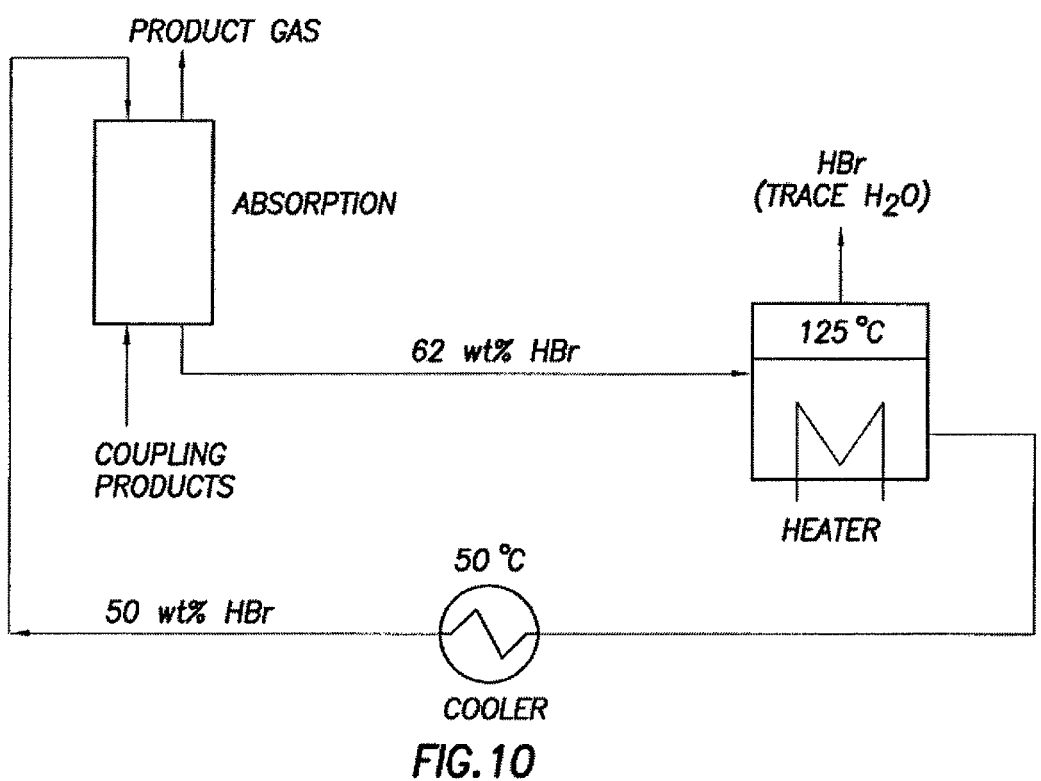
FIG. 10 is a schematic view of one embodiment of a temperature swing absorption system, for use in the practice of the invention.
Figure 11:
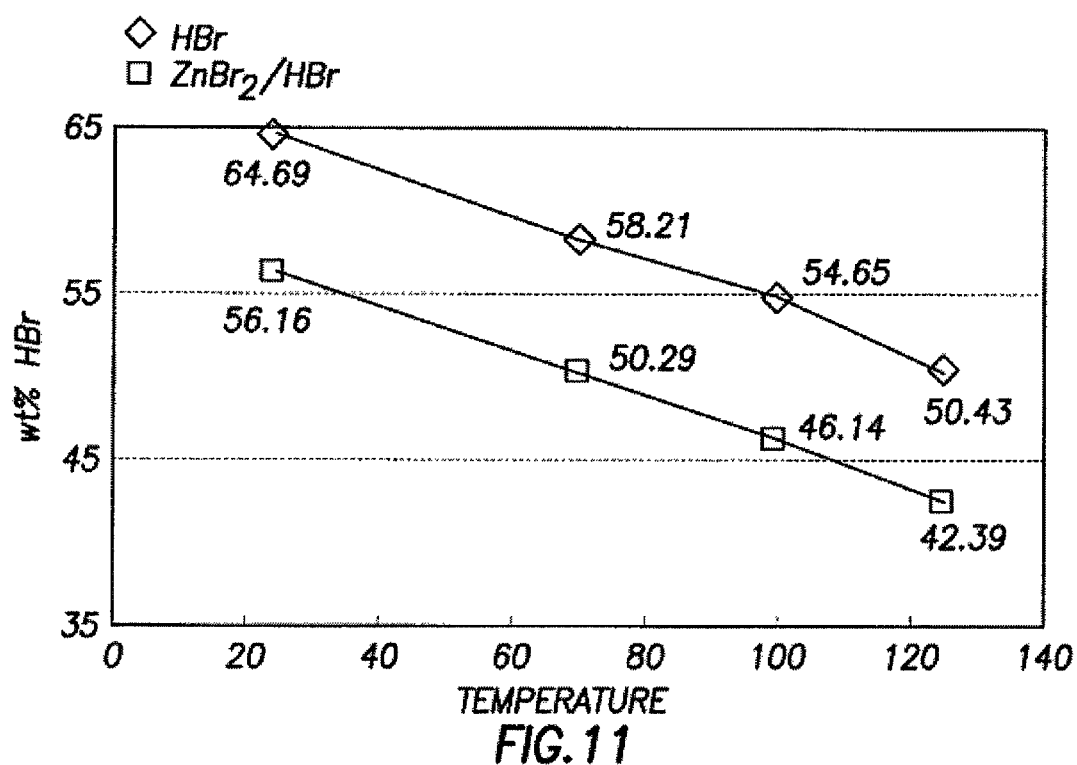
FIG. 11 is a chart showing the solubility of HBr in water for one embodiment of an absorption system, for use in the practice of the invention.

In another aspect of the invention shown in FIG. 10, a process for separating anhydrous HBr from an aqueous solution of HBr is provided using temperature swing absorption. As described above, HBr may be absorbed from the products stream using an aqueous solution. The effect of temperature on the solubility of HBr in water is shown in FIG. 11. The HBr absorption column may use aqueous HBr as the feed such that the overall feed concentration is at least about 48% by weight HBr, and after absorbing HBr, the outlet concentration may be between about 50% and about 80% HBr by weight. In an embodiment, the outlet of the absorption system may be a concentrated aqueous HBr stream with a concentration of at least about 48% HBr by weight, with a preferred concentration between about 55% and about 75% HBr by weight. The concentrated aqueous HBr stream may be sent to the evaporation state for HBr recovery. In an embodiment, the absorption column may be glass lined carbon steel or polymer lined carbon steel. Graphite heat exchangers may be used in the process.

In an embodiment, the absorption column may be a packed column. In another embodiment, a tray column may be used. The absorption column may operate at a temperature of about 150° C. or lower. As a large amount of heat may be generated during HBr absorption, the heat may be removed using an external circulation heat exchanger. The hydrocarbon products may leave in the gas outlet.

Higher boiling hydrocarbons may condense and leave with the outlet, where they may be separated using a liquid-liquid phase separator (not depicted in the drawing), since aqueous HBr and hydrocarbons phase separate. At pressures above about 5 atm, the liquid hydrocarbons may be easily separated from light gases and HBr by cooling the stream and using flash separation before introducing the gas into the absorption column. As a general trend, the temperature required for an HBr stripper may increase with pressure. After phase separation, aqueous HBr is sent to a heater where the temperature is increased. The decrease in HBr solubility at this temperature results in HBr removal in the gas phase. In some embodiments, trace amount of water may be removed with the HBr. However, in most cases, measurements in the laboratory did not detect any water present in the HBr vapor. The aqueous HBr may exit the heater/evaporator and may be cooled before recirculation to the absorption column.

In another aspect of the invention, various approaches to product clean-up (separation and/or purification) are provided. A number of bromide species may be present in the unpurified product stream: HBr, organic bromides such as methyl bromide and dibromomethane, and bromo-aromatics. In one embodiment of the invention, hydrocarbon products may be separated from brominated species by passing the product stream over copper metal, NiO, CaO, ZnO, MgO, BaO, or combinations thereof. Preferably, the products may be run over one or more of the above-listed materials at a temperature of from about 25° C. to about 600° C., more preferably, about 400° C. to about 500° C. This process may be tolerant of any $CO_2$ that may be present.

Figure 12:
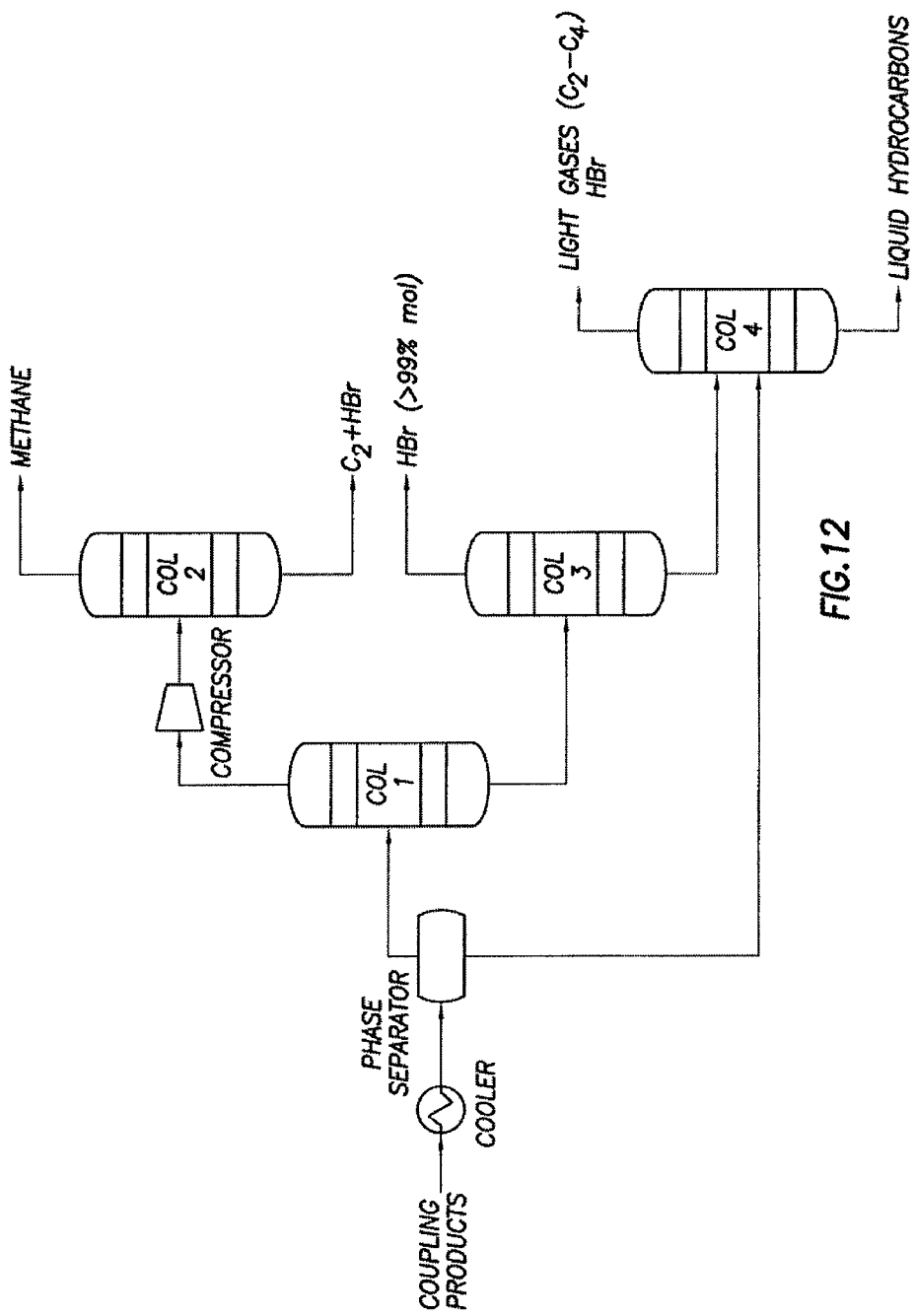
FIG. 12 is a schematic view of one embodiment of a product separation sub-system, for use in the practice of the invention.

In still another embodiment, HBr may be separated from the hydrocarbon products stream using distillation. Since HBr is the largest component in the C—C coupling product stream and has the lowest boiling point (about −67° C. at 1 atm), the distillation process must be performed at a higher pressure. A schematic for the separation system is shown in FIG. 12. If the products from coupling are at a lower pressure, they may be compressed to a pressure of about 10 atm or higher and the first column (Col 1) may separate methane and light gases from HBr and higher boiling components. The distillate may consist of a small amount of HBr. The distillate stream is compressed to a pressure of about 15 atm or higher to increase the condenser temperature for the demethanizer (Col 2). The bottoms stream of the demethanizer consists of ethane with a small amount of HBr. The bottom stream from the first column (Col 1) may be sent to a series of distillation columns (Cols. 3 and 4) where HBr may be separated and sent to the bromine generation section (not shown), and the light gases and liquid hydrocarbon products are obtained as the distillate and bottoms, respectively. Compression needs may be reduced if the coupling reactor is operated at a higher pressure. In certain embodiments, the coupling product inlet to the separation system may be at a high pressure of about 15 atm to about 40 atm and hence compression may not be needed downstream.

In another embodiment, particularly for large-scale production of hydrocarbons, unconverted methane may be separated from other light hydrocarbons as well as heavier products (e.g., benzene, toluene, etc.) using distillation. For example, in FIGS. 1 and 2, methane and other light hydrocarbons exit the absorption column through a gas outlet and are directed to a separation unit (SEP. II). Any unconverted methyl bromide may be removed with the light gases and may be recycled back to the bromination/reproportionation reactor. Heavier hydrocarbons may be removed as a liquid distillate.

Molecular Halogen Generation

In one embodiment of the invention, catalytic halogen generation may be carried out by reacting hydrohalic acid and molecular oxygen over a suitable catalyst. The general reaction may be represented by equation (1):

$$2HX + \tfrac{1}{2}O_2 \xrightarrow{catalyst} X_2 + H_2O \tag{1}$$

The process may occur at a range of temperatures and mole ratios of hydrohalic acid (HX) and molecular oxygen ($O_2$), e.g., about 4:1 to about 0.001:1 HX/$O_2$, preferably about 4:1 (to fit the reaction stoichiometry), more preferably about 3.5:1 (to prevent eventual HBr breakthrough).

Halogen may be generated using pure oxygen, air, or oxygen-enriched gas, and the reaction may be run with a variety of inert nonreacting gases such as nitrogen, carbon dioxide, argon, helium, and water steam being present. Any proportion of these gases may be combined as pure gases or selected mixtures thereof, to accommodate process requirements.

A number of materials have been identified as halogen generation catalysts. It is possible to use one type of catalyst or a combination of any number, configuration, or proportion of catalysts. Oxides, halides, and/or oxy-halides of one or more metals, such as Cu, Ag, Au, Fe, Co, Ni, Mn, Ce, V, Nb, Mo, Pd, Ta, or W are representative, more preferably Mg, Ca, Sr, Ba, V, Cr, Mn, Fe, Co, Ni, Cu, Zn, or Ce. The most preferable catalysts are oxides, halides, and/or oxy-halides of Cu. These materials may be considered cataloreactants as discussed in more detail below.

Although not bound by theory, the following equations are considered representative of the chemistry believed to take place when such materials are used to catalyze halogen formation:

$$CaO + 2HBr \rightarrow CaBr_2 + H_2O \tag{2}$$

$$CaBr_2 + \tfrac{1}{2}O_2 \rightarrow CaO + Br_2 \tag{3}$$

for metal oxides in which the metal does not change oxidation states, and $$Co_3O_4 + 8HBr \rightarrow 3CoBr_2 + 4H_2O + Br_2 \tag{4}$$

$$3CoBr_2 + 2O_2 \rightarrow Co_3O_4 + 3Br_2 \tag{5}$$

for metal oxides in which the metal does change oxidation states. The net reaction for equations (2)+(3) and equations (4)+(5) is equation (7):

$$2HX \xrightarrow{catalyst} X_2 + H_2O \tag{7}$$

which is equivalent to equation (1).

In one embodiment of the invention, chlorine is used as the halogenating agent, and ceria ($CeO_2$) is used to catalyze the generation of chlorine from hydrochloric acid. The following equations are considered representative:

$$2CeO_2 + 8HCl \rightarrow 2CeCl_3 + 4H_2O + Cl_2 \tag{8}$$

$$2CeCl_3 + 2O_2 \rightarrow 2CeO_2 + 3Cl_2 \tag{9}$$

for an overall reaction: $2HCl + \tfrac{1}{2}O_2 \rightarrow H_2O + Cl_2$ (10)

which is also equivalent to equation (1).

This use of ceria is quite novel, as it allows essentially complete consumption of HCl. In contrast, previous reactions of metal oxides, HCl, and oxygen have typically yielded HCl/$Cl_2$ mixtures. Thus, ceria can advantageously be employed as a halogen regeneration catalyst, particularly where chlorine is used for alkane halogenation, with chlorine's attendant lower cost and familiarity to industry.

In one embodiment of the invention, the halogen generation catalyst(s) may be supported on porous or nonporous alumina, silica, zirconia, titania or mixtures thereof, or another suitable support. A range of temperatures may be employed to maximize process efficiency, e.g., about 200° C. to about 600° C., more preferably about 350° C. to about 450° C.

Solid Reactant Removal of Hydrogen Halide and Halide Regeneration

In another embodiment, the hydrogen halide generated during catalytic coupling may be separated from the product stream and regenerated using a cataloreactant. A cataloreactant may facilitate carbon-carbon coupling, e.g., hydrocarbon oligomerization or metathesis. The term "cataloreactant" may refer to an inorganic compound that (a) contains at least one metal atom and at least one oxygen atom, and (b) facilitate the production of a higher hydrocarbon. Nonlimiting examples of cataloreactants include zeolites, doped zeolites, metal oxides, mixed metal oxides, metal oxide-impregnated zeolites, and similar materials, mixtures of such materials, as well as any other material described herein for capturing and converting hydrogen halides. Nonlimiting examples of dopants include alkaline-earth metals, such as calcium and magnesium, and their oxides and/or hydroxides. A nonlimiting list of metal oxides may include oxides of copper, magnesium, yttrium, nickel, cobalt, iron, calcium, vanadium, molybdenum, chromium, manganese, zinc, lanthanum, tungsten, tin, indium, bismuth, and mixtures thereof.

Without wishing to be limited by theory, it is believed that a cataloreactant may differ from a true catalyst as it may be converted to a metal halide when exposed to a hydrogen halide. The metal oxide may then be regenerated by treating the metal halide with oxygen or air (preferably at an elevated temperature) to allow at least some of the cataloreactant to be recycled within the process. The cataloreactant may also act as a halogen release and sequestering agent, offering the possibility of obtaining a tunable coupling product distribution. The choice of cataloreactant may allow the product distribution to include the ability to produce oxygenates if desired. The overall chemical cycle may result in water being created as the only byproduct of the reaction. When used solely for hydrogen halide capture, a cataloreactant may be referred to as a solid reactant. Further, the use of a solid reactant for hydrogen halide capture and elemental halide recovery reduces halogen inventory, simplifies the process operations and may reduce the overall capital cost.

In an embodiment, a cataloreactant may be redox or non-redox active. As used herein, the term "non-redox active" may refer to a metal or a metal oxide that has a single, stable oxidation state. For example, a non-redox active metal or metal oxide may include, but is not limited to, Ni, Ca, Mg, or Ba. Non-redox active metals or metal oxides may capture and sequester a hydrogen halide without releasing an elemental halide in the process. For example, equations (2) and (3) presented above demonstrate a non-redox active cataloreactant that may effectively capture a hydrogen halide. As used herein, the term "redox active" may refer to a metal or metal oxide that has more than one stable oxidation state. For example, a redox active metal or metal oxide may include, but is not limited to, Cu, Co, Ce, or Fe. An advantage of using redox active metal oxides is that they may be regenerated at a lower temperature, enabling a substantial decrease in the energy needed in the overall process. Redox active metals or metal oxides may generate elemental halide when used in the hydrogen halide capture and regeneration cycle. For example, equations (4) and (5) presented above demonstrate a redox-active cataloreactant in the context of a bromine based system that may release elemental bromine during the hydrogen bromide capture reaction. The amount of element halogen released, if any, by a redox-active system may depend on the halide used, the conditions of the reactor, and the choice of cataloreactant material.

In an embodiment, a solid reactant may be used to capture and oxidize hydrogen halide. In this embodiment, a stream containing a hydrogen halide may be passed over the solid reactant to generate the corresponding metal halide. The solid reactant may be a redox or non-redox active material. The hydrogen halide capture reaction may be generalized as:

$$MO(\text{metal oxide}) + 2HX \leftrightarrow MX_2(\text{metal halide}) + H_2O$$

for a non-redox active solid reactant.

In an embodiment, the stream containing the hydrogen halide may come from a variety of sources. For example, the hydrogen halide may be generated as a result of an aqueous absorption of the hydrogen halide from the products stream exiting the coupling reactor. Alternatively, the stream containing the hydrogen halide may be the products stream leaving the bromination reactor or the coupling reactor. In still another embodiment, the stream containing the hydrogen halide may have been partially separated from the products stream exiting the coupling reactor. For example, any hydrogen halide may be separated from the products stream along with a methane stream or a light hydrocarbon stream before being passed to a vessel containing a solid reactant. In these embodiments, the solid reactant may be used to capture any hydrogen halide contained within the stream, resulting in a stream that may be essentially free of hydrogen halide.

A solid reactant material that has been converted into a metal halide may be regenerated by treatment with air or oxygen to release an elemental halogen and convert the solid reactant back into the original oxide material. As used herein, the term "air or oxygen" may include any number of oxygen-based or oxygen-containing gas streams. Examples include, without limitation, ordinary air, pure oxygen gas ($O_2$), oxygen gas containing minor amounts of other gaseous components, dilute streams of oxygen gas in a carrier gas (e.g., helium), oxygen-enriched air, etc. Exposure to air or oxygen may regenerate the metal halide species back into the corresponding metal-oxygen species. Upon regeneration, the elemental halide that is release may be recycled for use in the bromination reactor or elsewhere in the process. The reaction in the regeneration section may generally be represented as:

$$MX_2(\text{metal halide}) + \tfrac{1}{2}O_2 \leftrightarrow MO(\text{metal oxide}) + X_2$$

In an embodiment, the performance characteristics of the solid reactant may be important as well as determine the reactor configuration best suited for a specific application. Important characteristics may include, but are not limited to, a high capacity for holding regenerable bromine, the stability of the bromine capacity over thousands of cycles, and the ability to rapidly neutralize HBr and regenerate the original solid reactant upon contact with air or oxygen.

In an embodiment, the solid reactant materials may be formed by using sol gel formulations, co-precipitation formulations, and wet impregnation, as disclosed herein. In addition, a solid reactant may comprise small amounts of enabling chemicals to enhance the stability of the solid and the rate of bromine regeneration. For example, potassium oxide and yttrium-stabilized zirconium may enhance the stability and reaction rates of the solid reactants during the HBr capture and bromine generation reactions.

The various steps of hydrogen halide capture and release may be carried out in a vessel, container, or reactor at appropriate pressures and temperatures. Factors that may affect the reactor conditions include, but are not limited to, the feedstock or composition of the hydrogen halide stream, the solid reactant composition, the flow rates, and the reactor type. In an embodiment, the reactor may be operated at, or slightly above, atmospheric pressure. In another embodiment, the reactor may be operated at a pressure ranging from about 1 atmosphere to about 200 atmospheres. In an embodiment, the reactor may be operated between about 0° C. to about 600° C., alternatively between about 200° C. to about 500° C. to facilitate hydrogen halide capture depending on the solid reactant material selected. For example, NiO or CaO may be used to capture HBr at a temperature between about 425° C. and about 500° C. for a non-redox active material based processes, while cobalt oxide or cerium oxide may be used for HBr capture at a temperature between about 300° C. and about 450° C. for a redox active material based process. In an embodiment, the reactor may be operated between about 0° C. to about 650° C., alternatively between about 200° C. to about 600° C. during halogen oxidation and release. This may regenerate the metal halide species back into the corresponding metal-oxygen species. Upon regeneration, elemental halide will be released, which may be recycled for use in the bromination reactor or elsewhere in the process. For example, $NiBr_2$ or $CaBr_2$ may be reacted with air or oxygen at a temperature between about 400° C. and about 600° C. to regenerate bromine in a non-redox active material based process, while cobalt bromide or cerium bromide may be reacted with air or oxygen at a temperature between about 200° C. and about 550° C. to regenerate bromine in a redox active material based process.

Materials for Hydrogen Halide Removal and Regeneration

In an embodiment of the processes described herein, various materials may act as a catalyst or cataloreactant active material, or a support. In some embodiments, gaseous HBr may be selectively removed from the product stream through the use of a calcium silicate based solid reactant. In this embodiment, as the gaseous HBr is removed from the product stream it may be directly converted to $Br_2$ in a second step using a suitable oxidant, for example oxygen. Generally, it is desirable that the calcium silicate based solid reactant have a high bromine capacity, e.g. greater than 4 mmol $Br_2/cm^3$, cyclically stable over many cycles, be in a form such that it may be used in either fixed, moving, or fluidized bed reactors, and have a minimal environmental, health and safety risk. In one embodiment, a suitable calcium silicate based solid reactant may be synthesized using a wet-impregnation technique. Using the wet-impregnation technique, a metal nitrate may be used to prepare the solid reactant, however any soluble compound would be suitable. In one embodiment, calcium nitrate and ethanol may be mixed in an amount sufficient such that the calcium nitrate dissolves. Additional metal nitrates, such as potassium nitrate, may also be added. The solute may then be combined with a suitable silica material of appropriate particle size. The mixture may then be refluxed at a temperature of approximately 100° C. for approximately three to five hours and then allowed to dry. The dried material may then be heated to 200° C. to remove the NOx component and then the materials may be calcined at approximately 550° C. for six hours at a heating rate of about one to five ° C./min.

While calcium silicate based solid reactants suitable for use in the present invention may be prepared in a variety of ways, calcium silicate based solid reactants prepared using the wet-impregnation technique described herein have been tested at neutralization temperatures of 400° C. and regeneration temperatures of 500° C. for 100 cycles with no apparent loss of capacity, other than an initial break in period of 5-20 cycles. Additionally, calcium silicate based solid reactants prepared by this method may be in a useable form as synthesized (up to ~2 mm pellets) and may require no additional binding agent for fixed bed applications. Calcium silicate based solid reactants may provide stable bromine capacities of about 1.5 mmol $Br_2$/g-solid to about 3 mmol $Br_2$/g-solid or greater. In some embodiments, the basicity of the calcium silicate based solid reactants may be increased via the addition of alkali metals, which may increase regeneration rates. For example, the addition of potassium in a molar ratio of about 5:20:75 (K:Ca:$SiO_2$) may increase reaction rates about 5 times when compared with materials with only calcium.

In an embodiment, a nickel oxide (NiO)-based nano-composite may be used as a solid reactant for selective capture of HBr and its subsequent conversion to $Br_2$. The materials used for the NiO based-nano composite may exhibit high capacity (about 4 mmol $Br_2$/g or higher), fast $Br_2$ generation rates, and long term cycle stability. As used herein, the term "cycle stability" is defined to mean that key properties of the solid reactant, such as, but not limited to, capacity, capture and regeneration rates, etc., do not change appreciably as the solid is repeatedly cycled between the oxide and bromide states, as well as between low and high temperature. Various wet-chemical embodiments may be used to synthesize nano-composite solid reactants, including sol-gel, sol-gel coupled with oil-drop, and co-precipitation based methods, as described in more detail below. While these embodiments may be described in terms of NiO-based solid reactants for HBr capture/$Br_2$ regeneration, the synthesis techniques may also be applicable for other metal oxide based solid reactants. Non-limiting examples include cobalt, copper, calcium, and iron oxides for capture/$Br_2$ regeneration. In addition, these techniques may also be applicable for regenerable solid reactants for $CO_2$ removal ($ZnO \leftrightarrow ZnCO_3$) and chemical looping combustion ($NiO \leftrightarrow Ni$).

In another embodiment, gaseous HBr may be selectively removed from the product stream through the use of a fluorinated alumina based materials. A metal oxide doped fluorinated alumina (e.g., $FAl_2O_3$) may be a stable solid reactant for hydrogen halide capture and elemental halogen regeneration. In some embodiments, a fluorinated alumina material, such as a calcium oxide doped fluorinated alumina, may be used as a cataloreactant for methanol synthesis. As a catalyst $FAl_2O_3$ may be effective in converting some olefins (e.g., isobutylene) to higher hydrocarbons, and may be used as a catalyst or component of a catalyst for alkyl halide coupling into higher hydrocarbons. Fluorinated alumina materials may exhibit a stable bromine capacity of about 2.0 to about 2.5 mmol $Br_2$/g for many cycles, for example up to about 500 cycles. The fluorinated alumina materials may exhibit high catalytic activity due to strong interactions between the fluorinated support crystal structure and any additional metals or metal oxides doped or ion exchanged with the material. The presence of fluorine in the material may result in enhanced Lewis acidity which may also account for a high level of catalytic activity. Catalysts or cataloreactants prepared using a fluorinated alumina material may be suitable for use in fixed, moving, and fluidized bed applications.

Additional materials may be used with a fluorinated alumina material to form a catalyst or cataloreactant for use in the production of higher hydrocarbons. For example, NiO and CaO may be supported on a high surface area fluorinated alumina. These materials may be doped with one or more alkali or alkali earth metals, which may increase the elemental halide regeneration rates when these materials are used. While not intending to be limited by theory, it is believed that unlike an inert support, a fluorinated alumina material may react with an active material (e.g., a metal oxide such as NiO, CaO, etc.) as a consequence of the material's Lewis acidity, which may result in surface immobilization of the active material. The immobilization of the active material may reduce or eliminate sintering, which may lead to catalyst or cataloreactant degradation.

High surface area fluorinated alumina ($FAl_2O_3$) may be synthesized by impregnating a high surface area alumina with an aqueous solution of ammonium fluoride, which is used as a fluorinating agent. After stirring the mixture for a sufficient amount of time at room temperature, the excess solution may be evaporated. The resulting material may be dried in an oven, followed by calcination under $N_2$. Additional materials may then be further added to the fluorinated alumina. For example, nickel nitrate or calcium nitrate may be used to wet impregnate the fluorinate alumina followed by calcining to produce a NiO or CaO doped fluorinated alumina, respectively.

In an embodiment, an active material may comprise less than about 30%, or alternatively, less than about 15% by weight fluorine in an alumina structure. The base alumina may be any suitable alumina and may include, for example, spheres, ellipsoids, toroids, etc. In an embodiment, an alumina sphere about 2 to about 3 millimeters (commercially available as Davicat Al-2750 from W.R. Grace & Co. of Columbia, Md.) may be used as the starting material for the synthesis of a fluorinated alumina.

In another embodiment, hydrogen halide generated in the process described herein may be removed using a metal halide salt with a plurality of oxidation states. In an embodiment, the metal may be copper, which may form two stable oxidation states with a halide such as bromine. In an embodiment in which the halogen is bromine, copper may form both $CuBr$ and $CuBr_2$. By cycling between the two oxidation states of Cu, a closed recycle loop of bromine may be created wherein bromine is mostly retained as a bromide salt.

In an embodiment, brominated alkyls from the bromination reactor may be coupled by contact with an appropriate catalyst to yield products and HBr. Gases from the coupling reactor may be cooled and contacted with water to absorb HBr and allow the mostly HBr-free coupling products to be sent to product separation and recovery. The aqueous solution of HBr may be contacted with CuBr, which may be recycled from a bromine generation step described below. Air or oxygen may be utilized to facilitate a reaction between HBr and CuBr resulting in the conversion of the CuBr to $CuBr_2$ and water. In another embodiment, an aqueous solution of $CuBr/CuBr_2$ may be used as the absorbent in the contact separation of the coupling reactor products from the HBr.

The $CuBr_2$, unreacted CuBr solids, and water may be separated using any technique capable of removing solids from an aqueous solution. For example, suitable separation techniques may include, but are not limited to, crystallization or evaporative crystallization followed by filtration or centrifugation. The $CuBr_2$ crystals, which may still contain water, may be dried at a temperature low enough to avoid bromine release. In an embodiment, the drying temperature may be below about 200° C. The dried $CuBr_2$ crystals may then be sent to a bromine generation unit.

In an embodiment, the bromine generation unit may comprise a heating chamber for heating the $CuBr_2$ to about 275° C., resulting in the conversion of the $CuBr_2$ to CuBr and the release of bromine as a vapor. In this embodiment, a carrier gas may be used to remove the bromine generated by the $CuBr_2$ in the bromine generation unit. In an embodiment, the carrier gas may be methane or any other light hydrocarbon stream. The bromine generation unit products, including bromine and any light hydrocarbons making up the carrier gas, may be separated from the solid CuBr and sent to a bromination reactor where the bromination reaction may be carried out. The bromine generation unit products may be heated in order to raise the temperature of the mixture to the temperature desired in a bromination reactor. The solid CuBr that is generated may be recycled to the HBr capture reactor. In some embodiments, the bromine generation reactor and the bromination reactor may take place in the same vessel.

In another embodiment, the copper bromide based process described above may be used as a scavenging material to capture any hydrogen halide passing to a process stream exiting the process. For example, an aqueous solution or a dry bed of CuBr may be used as a final HBr trap prior to any vent streams leaving the process. Such traps may prevent any HBr from escaping the process and allow the HBr to be subsequently captured and converted to elemental bromine for reuse in the process.

Methods of Preparing Catalysts and Cataloreactants

Figures 13, 14:
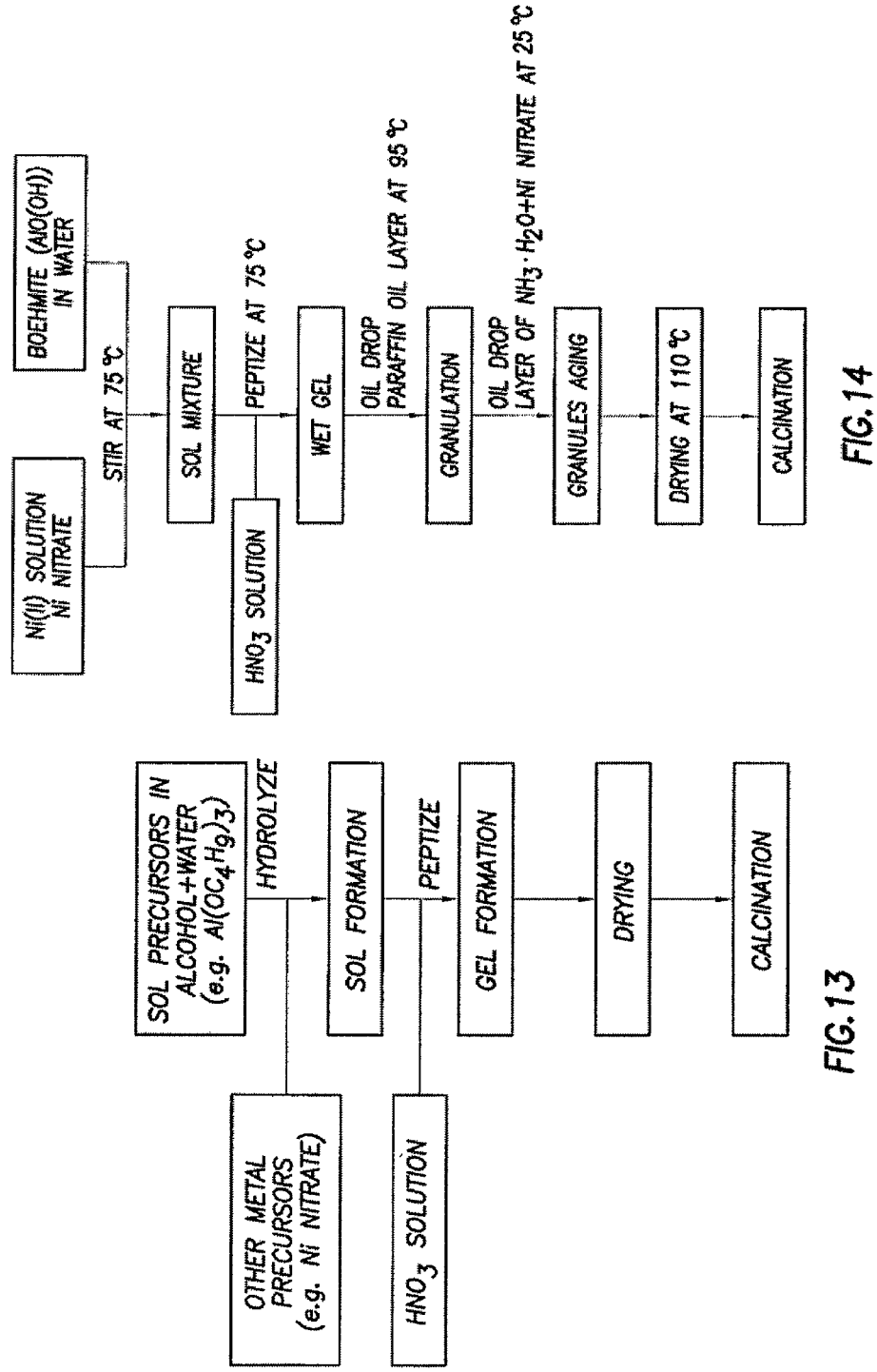
FIG. 13 is a chart showing the absorptive capacity of a NiO catalyst for one embodiment of an adsorption system, for use in the practice of the invention.
FIG. 14 is a flow-chart showing one embodiment of a process for creating sol-gel granules.

Any of the materials useful as coupling catalysts, or even bromination or oxidation catalysts, may be synthesized using a variety of methods. As mentioned above, a NiO based nano-composite (e.g., powder form) solid reactant may be synthesized using a sol-gel based procedure. One example of a typical sol-gel based procedure for the synthesis of nano-composite solid reactant (powder form) is described in FIG. 13. For example, to synthesize a $NiO$—$K_2O$—$Y_2O_3$—$ZrO_2$—$Al_2O_3$ nano-composite, an aluminum precursor (e.g., aluminum isopropoxide or aluminum tri-sec-butoxide) and zirconium propoxide may be dissolved in isopropanol. The overall concentration of Al(III) may be about 0.6 M (generally controlled in the range of about 0.1 to about 1.0 M). Deionized water may then be added drop-wise. Hydrolysis may occur upon adding the water and may be promoted by stirring at about 60° C. (generally at about 40 to about 90° C.) to produce a sol solution. A nickel precursor (e.g., nickel nitrate or chloride), potassium nitrate and yttrium nitrate, all of which are at least partially water soluble, may be dissolved in deionized water with a concentration of about 3.0 M (generally about 1 to about 6 M). The Ni/K/Y solution may be added and the resulting sol solution may then be stirred for approximately 30 minutes with heating when the total volume of the sol solution is reduced by about 30 to about 50% by evaporation. The sol gel may be peptized at 60° C. by adding 1 M nitric acid (the amount of the acid may be determined by the molar ratio of protons to Al(III) of about 0.05 to about 0.4), which may result in the formation of a gel. To ensure good mixing of all the cations, the gel mixture may then be further stirred for several hours. The gel may be dried in an oven at about 110° C. to about 150° C., where the exact temperature may depend on the amount of nickel precursor used. The dried material may be calcined at about 450° C. to about 850° C. for about 6 hours using a heating rate of about 1° C./min. The resulting material may have a nominal composition of about 51% $NiO$-2% $K_2O$-0.6% $Y_2O_3$-4.4% $ZrO_2$-42% $AlO_3$.

Another method for synthesizing nano-composite solid reactants may utilize sol-gel techniques coupled with oil-drop (e.g., pellet form). One example of this method is described in FIG. 14. For example, in order to synthesize a $NiO$—$AlO_3$ nano-composite pellet, nickel nitrate of an appropriate amount may be added and mixed with an aqueous sol of boehmite at 75° C. for about 2 hours. Nitric acid may then be added to peptize the sol solution, with pH controlled in the range of about 0 to about 5. A wet gel may be obtained after heating and stirring at about 50° C. for another hour. An organic acid such as acrylic acid may also be added to the gel as a polymerization initiator. The wet gel may be dropped into an immiscible paraffin oil layer and spherical shaped granules may form. The granules may pass through the oil layer and fall into an ammonia solution containing a predetermined concentration of nickel nitrate, where they may be aged from about 1 hour to about 5 days. During the aging process, the wet gel granules may become rigid gel particles (e.g., pellets). The solid granules may then be removed and washed with water and ethanol, which may be followed by drying at about 100° C. to about 150° C. Calcination may be conducted at about 450° C. to about 850° C. for about 6 hours with a heating rate of about 1° C./min.

Figure 15:
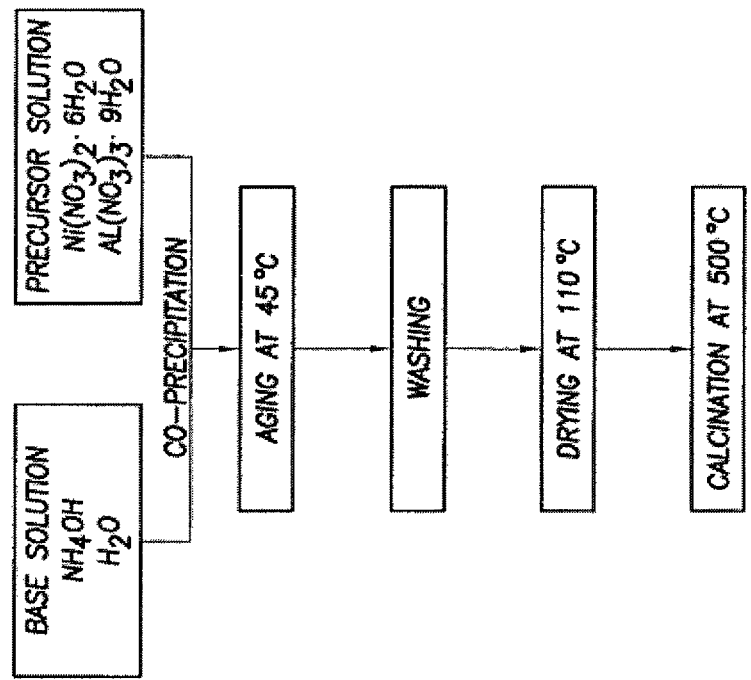
FIG. 15 is a flow-chart showing one embodiment of a process for creating co-precipitation granules.

FIG. 15 illustrates a co-precipitation method, which is yet another example of a method for synthesizing nano-composite solid reactants. For example, in order to synthesize a $NiO$—$AlO_3$ nano-composite solid reactant, an aqueous solution of nickel nitrate and aluminum nitrate may be stirred at about 45° C. while an about 5.8% $NH_3.H_2O$ solution may be added drop-wise. The hydroxides of nickel and aluminum may start to precipitate and the final pH may be controlled in the range of about 8 to about 11. The whole solution may then be aged at about 45° C. for about one day before it is filtered. The precipitates may be washed with deionized water and dried at about 100° C. to about 150° C. The dried powder may then be calcined at about 450° C. to about 750° C. for about 6 hours with a heating rate of about 1° C./min.

Examples of other suitable nano-composite solid reactants may include about 30% $NiO-Al_2O_3$ by sol-gel; about 30% $NiO-Al_2O_3$ with K doping by sol-gel; about 50% $NiO-Al_2O_3$ with K and YSZ doping by sol-gel; and about 42% $NiO-La_2O_3-Al_2O_3$ by co-precipitation.

All the above synthesis methods may yield a nano-composite material comprising a metal oxide (e.g., NiO) and one or more additional components (e.g., $AlO_3$, K, YSZ, or $La_2O_3$). The main variables in the synthesis procedure may be the different components in the composite and their respective compositions, pH, aging time/temperature, concentration of the metal oxide in the ammonia aging solution, and calcination temperature.

The composition of the metal oxide in the nano-composite has been found to have an important impact on both the capacity of the material as well as its stability. If the composition of the metal oxide is too low, then the material will have a small, but stable capacity (e.g., NiO composition at about 30% results in a stable capacity of about 1 mmol $Br_2/g$, which may be too small for commercial applications). However, if the composition of the metal oxide is too high, the material may exhibit a high initial capacity, which may start to decrease rapidly with repeated oxide/bromide cycles. (e.g., an about 70% $NiO-AlO_3$ nano-composite material prepared using a sol-gel synthesis procedure may show an initial capacity of about 7.0 mmol $Br_2/g$, which may then decrease to about 2 mmol $Br_2/g$ after less than about 250 cycles).

While the exact mechanism by which these nano-composite materials exhibit their desired properties (e.g., cycle stability, fast reaction rates, etc.) as a solid reactant is not known, it is believed that they are due to a combination of the structure of the nano-composite material itself as well as the nature and compositions of the other components within the nano-composite. The near molecular level dispersion of the active metal oxide within the nano-composite material may result in thermodynamic properties that do not favor particle sintering as the material cycles between the oxide and bromide states. In addition, it is also believed that surface reactions between the metal oxide and at least some of the other components may immobilize the metal oxide, thereby preventing, or significantly reducing, loss of surface area due to sintering. For example, $NiO-La_2O_3-AlO_3$ and $NiO-AlO_3$ nano-composites exhibit stable capacities of about 4.0 mmol $Br_2/g$ and about 3.0 mmol $Br_2/g$, respectively, while a $NiO-SiO_2$ nano-composite may lose capacity quickly as it cycles (e.g., the material has an initial capacity of about 3.0 mmol $Br_2/g$, but drops to about 1.5 mmol $Br_2/g$ after about 180 cycles it). These trends may hold true even if all three materials are synthesized using a similar techniques and conditions.

In addition to impacting the cycle stability of the materials, the other components in the composite may also affect the rate of $Br_2$ generation. For example, adding alkaline metals (e.g., Li, Na, K and Cs) may significantly increase the $Br_2$ regeneration rates of NiO nano-composites. Also oxygen-ion conducting compounds have also been found to be effective in enhancing the $Br_2$ generation rates of these materials. For example, it is believed that $Y_2O_3-ZrO_2$ in the composite may react in part to form yttria-stabilized-zirconia, YSZ, which may be an oxygen conducting compound.

In some embodiments, the nano-composite solid reactants may be encapsulated. It may be desirable to encapsulate a nano-composite to stabilize the particle size and surface area. In one embodiment, encapsulation may be achieved by water-in-oil microemulsion, organic template directing solution evaporation, or Stober-like methods. Factors to be considered when encapsulating a solid reactant include porosity/pore size and void space inside the shell.

Aqueous Process for Hydrogen Halide Removal and Halide Regeneration

In an embodiment, hydrogen halide may be oxidized to generate a corresponding elemental halide using an aqueous solution with an appropriate catalyst. The catalyst may take advantage of the change in the oxidation state of a material with multiple oxidation states. In various embodiments, the aqueous based process may be described in connection with HBr and $Br_2$ and the semi-metals Se and Te, but it should be apparent to one skilled in the art that the process is not limited to the described embodiments. Both selenium and tellurium are semi-metals that have several oxidation states including −2, 2, 4 and 6. Additional elements with multiple oxidation states include, without limitation, Cu(II)/Cu(I), Fe(III)/Fe(II), Sb(V)/Sb(III), Mn(IV)/Mn(II), V(V)/V(IV), As(V)/As(III), and Ru(IV)/Ru(III). The following description uses selenium as example although the same description applies to tellurium and the other elements with multiple oxidation states unless noted otherwise.

The aqueous based oxidation process takes advantage of the reduction capability of Se (I) and Se(II) compounds towards oxygen from the air, which may be oxidized to Se(IV). The Se(IV) state is a sufficiently strong oxidizer and may be capable of oxidizing $HBr/Br^-$ to elemental bromine. In such a cycle the selenium may shuttle between the two oxidation states and converts the HBr to $Br_2$ using air or oxygen at relatively mild conditions.

The cycle starts with Se(IV) compound such as $SeO_2$, which may be in an acidic environment (an acidic environment may enhance the oxidation power of Se(IV)). A first series of reactions (Eq. 11 to Eq. 17) has the net effect of converting HBr into $Br_2$ and $H_2O$ and converting Se(IV) to Se(II).

$$SeO_2 + 4HBr \rightarrow SeBr_4 + 2H_2O \quad \text{(Eq. 11)}$$

$$SeBr_4 \rightarrow SeBr_2 + Br_2 \quad \text{(Eq. 12)}$$

$$2SeBr_4 \rightarrow Se_2Br_2 + Br_2 \quad \text{(Eq. 13)}$$

$$Se_2Br_2 \rightarrow SeBr_2 + Se \quad \text{(Eq. 14)}$$

$$2Se_2Br_2 + 2H_2O \rightarrow SeO_2 + 4HBr + 3Se \quad \text{(Eq. 15)}$$

$$Se + O_2 \rightarrow SeO_2 \quad \text{(Eq. 16)}$$

$$3SeBr_2 \rightarrow Se_2Br_2 + SeBr_4 \quad \text{(Eq. 17)}$$

$SeBr_4$ is an orange red crystalline solid that may dissociate at temperatures exceeding 70° C. yielding Se, $Se_2Br_2$, $SeBr_2$, and $Br_2$. Heating HBr and $SeO_2$ in a closed vessel above 45° C. may lead to sublimation of $SeBr_4$ crystals. Similarly, heating in an open container or in the presence of inert pass through gas may result in free $Br_2$ being liberated along with the other products-metallic selenium, which may appear as a solid powder precipitate upon cooling, and the lower bromides $Se_2Br_2$ and $SeBr_2$ observed as refluxing red oily liquid ($Se_2Br_2$ is dark red, pungent oily liquid which boils at about 225° C. to about 230° C.).

The reaction according to Eq. 11 may take place at approximately room temperature or lower while the remainder of the equations may take place at a temperature ranging from about 65° C. to about 300° C. and a pressure ranging from about 0.1 atm to about 40 atm. At the temperature of the reaction the bromine may be evaporated from the reactor along with water vapor due to the reactions shown in Eq. 12 through Eq. 14. Despite the existence of an HBr-water azeotrope, HBr may not escape the system because practically all of the bromine may be bound as selenium species and the solution may contain relatively low HBr concentrations at or below the azeotropic composition. However, the process may be tolerant to the presence of small amounts of HBr in the vapor phase.

A second series of reactions (eq. 18 eq. 20) may result in the regeneration of the active Se(IV). This may be done either simultaneously or sequentially with the first set of reactions:

$$2Se(II) + O_2 + 4H^+ \rightarrow 2Se(IV) + 2H_2O \qquad (Eq.\ 18)$$

Se(IV) may not oxidize $Br_2$ to $BrO_3^-$. The electrode potential for the $Br_2$ to $BrO_3^-$ reaction is about 1.482 V which is above the oxidation potential of Se(IV)/Se(II). The electrode potential for $Br_2/BrO^-$ is about 1.574 V, which may be high enough so that the reaction to hypobromite does not occur. The selenium redox potentials are not as high, making any such oxidation unlikely to occur. Even if generated in small amounts $BrO^-$ and $BrO_3^-$ may not leave the system due to the following reactions in the acidic environment in the reactor:

$$5Br^- + 6H^+ BrO_3^- \rightarrow 3Br_2 + 3H_2O \qquad (Eq.\ 19)$$

$$Br^- + BrO^- + 2H^+ \rightarrow Br_2 + H_2O \qquad (Eq.\ 20)$$

These reactions may maintain a low concentration of any selenium oxybromides as they may react as soon as they are formed. The two main products leaving the system may include bromine and water. Under normal operating conditions, these components may leave as vapor. The other components of the reaction mixture may generally be nonvolatile. However, trace components other than bromine and water may appear in the products stream depending on the conditions and type of the reactor.

A benefit of this process is the safety of operation. Although some of the reactants may be volatile and toxic compounds (e.g., $SeBr_4$ and $Se_2Br_2$), the hazard may be reduced or eliminated by using a large amount of water in the event of a spill. Water may rapidly change the toxic, volatile bromides to inert solids (Se) and non-volatile aqueous species (e.g., $SeO_2$). For example, equations 11 and 12 demonstrate the reactions of $SeBr_4$ and $Se_2Br_2$ with water.

$$SeBr_4 + 2H_2O \rightarrow SeO_2 + 4HBr \qquad (Eq.\ 21)$$

$$2Se_2Br_2 + 2H_2O \rightarrow Se + SeO_2 + 4HBr \qquad (Eq.\ 22)$$

In an embodiment using iodine and selenium, or iodine and tellurium, the same set of equations may apply (e.g., Eq. 11-Eq. 22), and thus, selenium or tellurium may be used as a catalyst for the oxidation of hydrogen iodide to iodine. In this embodiment, the pressure may range from about 0.1 atm to about 40 atm, while the operating temperature may be lower as HI is a stronger reducing agent. For example, the temperature of the system may range from about 0° C. to about 120° C. In some embodiments, tellurium and selenium may be used to convert hydrochloric acid to chlorine, though higher temperatures may be required. For example, the temperature may range from about 150° C. to about 500° C., which may result in the reactions occurring in the gas phase. Such reactions may generally be described by equations 11 through 14. Tellurium may be used as a catalyst for the bromine generation from hydrogen bromide with chemical processes identical to those described for the selenium system above; however the temperatures may be higher than for selenium. In an embodiment that utilizes tellurium to generate bromine from hydrogen bromide, the reaction temperature may range from about 100° C. to about 350° C.

Figure 16:
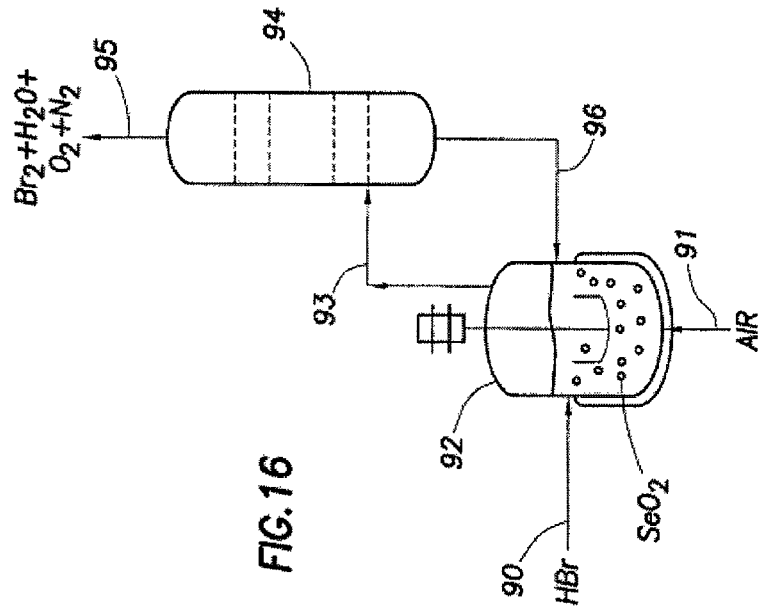
FIG. 16 is a schematic view of one embodiment of a liquid phase HBr oxidation system, for use in the practice of the invention.

FIG. 16 illustrates a schematic embodiment of a reactor system for the conversion of HBr to $Br_2$. In this embodiment, a stream containing HBr 90 and a stream containing air or oxygen 91 may be fed to a reactor 92 containing an aqueous solution of selenium bromide, various oxybromides (e.g., $SeOBr_2$, $Se_2Br_2$ etc.), or any combination thereof. Selenium oxide, if present during the reaction, may be in a slurry phase. Products may be removed from the reactor as a vapor stream. The reactor outlet stream 93 may contain selenium bromide and HBr. Due to the presence of the HBr-water azeotrope and the fact that the boiling point of selenium bromide is higher than either bromine or water, it may be possible to use a reactive distillation system 94 to fractionate the reactor outlet 93 whereby only bromine, water, unconverted oxygen, and nitrogen leave the system in the product mixture 95. The bottoms stream 96 may return any selenium compounds to the reactor 92. In an embodiment, the performance of the system may be improved by changing the feed stage and number of stages of the fractionator 94. In another embodiment, the performance of the system may be improved by adding an additional reboiler, by varying the reflux and reboil ratios, or a combination thereof. The product mixture 95 containing bromine, water, oxygen and nitrogen may be processed using any of the methods disclosed herein.

In another embodiment, any hydrogen halide generated in the coupling reactor may be separated from the coupling products, any unreacted feedstock, and any other inert gases by passing the entire coupling reactor product stream through the aqueous Se catalyst system. In this embodiment, the coupling reactor products stream may be cooled prior to entering the aqueous Se catalyst system to prevent overheating and boiling of the aqueous reaction medium. The HBr may be adsorbed by the aqueous phase and phase separate from any hydrocarbons, including any products and unreacted feedstock. The aqueous Se system enriched in HBr may then be re-circulated back to the bromine generation reactor where it may be converted to bromine. This approach may eliminate the need for a separate HBr/coupling products reactor, thus reducing the overall capital costs. In this embodiment, the aqueous Se system may be oxidized to convert the Se species to highly water soluble $H_2SeBr_6$ and $H_2SeO_3$ before being contacted with the coupling reactor product stream. Such oxidation may help prevent transferring any of the Se compounds into the organic phase and contaminating the final product stream.

The reactor depicted in FIG. 16 may a CSTR (continuous stirred tank reactor), however other conventional reactors such as CSTRs in series, PFR (plug flow reactor), packed columns, reactors with multiple inlets and vapor outlets, multiple reactors in series, and other reactor types known to those skilled in the art may also be used.

In another embodiment, the MeBr created in the bromination reaction may be reacted directly in the aqueous oxidation process to $Br_2$. This would require operation at mildly acidic conditions. An advantage would be the simplicity of the process.

The process may require three reaction stages characterized by the following equations:

$$CH_4(g) + Br_2(g) \Rightarrow CH_3Br(g) + HBr(g) \qquad (eq.\ 23)$$

$$CH_3Br(aq) + H_2O(aq) \Rightarrow CH_3OH(aq) + HBr(aq) \qquad (eq.\ 24)$$

$$2HBr(aq) + \tfrac{1}{2}O_2(aq) \Rightarrow H_2O(aq) + Br_2(aq)(\text{Using SeO}_2 \text{ catalyst}) \qquad (eq.\ 25)$$

First, methane may be brominated (eq. 23). The resulting bromomethane may be fed to a reactor containing water, and hydrolysis to produce methanol may take place (eq. 24). Hydrogen bromide may be produced in both Eq. 23 and Eq. 24. Hydrogen bromide may be oxidized in an aqueous solution by the action of oxygen in the presence of catalytic selenium dioxide (eq. 15)

Thermal bromination of methane proceeds according to (eq. 13). Conversion of methyl bromide to methanol and aqueous HBr (eq. 14) is based on the well known reactivity of alkyl halides towards hydrolysis. In general this reaction may be fast for alkyl bromides at temperatures at about 100° C. and pressures at about 1 to about 10 atm. Eq. 15 may be achieved at about 100° C. through the use of $SeO_2$ as a catalyst.

Recovery and Recycle of Molecular Halogen

Halogen generation produces both water and molecular halogen. Water may be separated from halogen and removed before the halogen is reacted with the hydrocarbon feedstock. Where the halogen is bromine, a bromine-water, liquid-liquid phase split may be achieved upon condensation of a mixture of these species. For example, in an embodiment, a liquid-liquid flash unit may be used to separate most of the bromine from water, simply and inexpensively. The bromine phase typically contains a very small amount of water, and may be sent directly to the bromination reactor. The water phase, however, may contain 1-3 wt % bromine. However, if air is used in the bromine generation step, nitrogen and unconverted oxygen may be present with the bromine and water stream that enters the flash.

The gas leaving the flash unit primarily consists of nitrogen and unconverted oxygen, but carries with it some bromine and water. The amount of bromine leaving with the vapor phase may depend on the temperature and pressure of the separation unit. The flash may be operated at temperatures ranging from about 0° C. to about 50° C.; however, a lower temperature (e.g., about 2° C. to about 10° C.) is preferred to reduce bromine leaving in the vapor stream. In an embodiment, the operating pressure is about 1 bar to about 50 bar, more preferably about 1 bar to about 30 bar. In an embodiment, the vapor stream may be sent to the bromine scavenging section for bromine recovery, as described below.

Bromine contained in the water-rich phase leaving the liquid-liquid flash may be effectively recovered by distillation. The presently described distillation subprocess may produce bromine or bromine-water azeotrope as a distillate, which may be recycled back to the flash unit or to a hydrogen halide oxidation process, as disclosed herein. The bottoms stream may consist mainly of water. Bromine may react reversibly with water to form small amounts of HBr and HOBr. In the distillation scheme, therefore, ppm levels of HBr (and/or HOBr) may be present in the bottoms stream. A side-stream rectifier or stripper may be utilized to reduce the bromine content of the bottoms stream to produce a pure water stream. Other alternatives that may reduce the bromine content of the water to below 10 ppm range include, but are not limited to, the addition of acids such as sulfuric acid, hydrochloric acid, and phosphoric acid, in very small quantities to reduce the pH of the water stream. Lowering the pH may drive the HBr and HOBr stream back to bromine and water, thereby substantially reducing the loss of bromine in the water stream. HBr present in the water stream may also be recovered using ion-exchange resins or electrochemical means.

Recovery of all Halogen for Reuse

Various streams in the process may contain some halogen that may be recovered prior to venting or otherwise allowing the stream to exit the process. Such streams may result from separation of the bromine from lighter components such as nitrogen or oxygen. For example, condensation, vapor-liquid separation, gas-solid adsorption/reaction, or any combination thereof may be used to separate residual bromine in a vapor stream from the other components of the stream. The vent streams may be treated in order to recover the halogen prior to venting the other components of the stream. In an embodiment, any scavenging method may be used that is capable of recovering at least some elemental halogen or hydrogen halide from a process stream. For example, a chilled liquid process or a solid scavenging process may be used to recover any halogen.

In an embodiment, the scavenging process may consist of a single pass technique, or a variety of techniques may be used in series. In some embodiments, a general scavenging technique such as a chilled brine process may be used to remove the majority of the halogen in a stream prior to treating the stream with a high capture efficiency scavenging technique such as solid adsorption/reaction. Such an embodiment may allow a high capture efficiency while avoiding an excessive burden on the final bromine adsorption/reaction, which may be the most expensive portion of the scavenging process. To achieve low levels of residual bromine the temperature of the stream being treated may need to be reduced to about 10° C. to about −30° C. The process stream being cooled may contain a variety of components such as water and bromine, which may freeze under these conditions. Therefore, simple cooling by indirect heat transfer may not suffice due to icing of the heat transfer surface. Such a problem may be overcome by introducing a brine coolant which may directly contact the process stream containing the halogen. Due the low freezing point associated with brines, the use of a brine may enable cooling to the desired temperature. Vaporizing the bromine by heating the brine can then occur, with further heating employed to facilitate concentration (e.g., evaporative concentration) of the brine for re-use. This approach to bromine recovery may be carried out either continuously or in batch mode.

In an embodiment, the brine solution may be composed of any salt or combination of salts that is at least partially soluble in an aqueous solution. In an embodiment, suitable salts may include commonly available salts such as NaCl or $CaCl_2$, or any salt of a halide corresponding to the halogen being recovered from the process stream. For example, if bromine is being recovered from a process stream, NaBr or $CaBr_2$ may be used to form the brine solution. As used herein, the term brine refers to an aqueous salt solution at, below, or above saturation. This may include salts that are undersaturated or super-saturated, depending on the process conditions. In an embodiment, the brine may have from about 0.1% to about 60% by weight salt in an aqueous solution. In another embodiment, the brine may have from about 10% to about 30% by weight salt in an aqueous solution. The aqueous solution may include any fluid containing water and may be derived from any source. For example, a water stream generated in the process may be used to form at least a portion of the brine solution.

In an embodiment, the brine solution may be directly contacted with the stream containing the halogen to be recovered. The brine coolant and liquid halogen formed by direct contact cooling may be separated from any other light gases present in the process stream in a vapor-liquid-liquid separator. Liquid from the separator may consist of two phases, a brine phase and the a liquid halogen phase. The liquid halogen phase may join a previously condensed halogen in the process or may be recycled in the process for further purification. The brine phase may be cooled and returned to the direct contact cooling operation.

In another embodiment, if the halogen captured in the direct contact cooler is dissolved in the brine and does not phase separate, then recovery of this halogen may be effected by heating the brine to vaporized the halogen in the brine. The vaporized halogen may be combined with vapor from a halogen generation operation, re-circulated to an upstream process, or any combination thereof.

In an embodiment, the chilled brine process may be operated using a brine with a temperature between about 0° C. and about −30° C. during the direct contact operation. In another embodiment, the chilled brine process may be operated using a brine with a temperature between about −5° C. and about −15° C. during the direct contact operation. Any pressure between about 1 atm to about 50 atm may be used, with a pressure between about 2 atm and about 30 atm being used in some embodiments.

In another embodiment, a solid halogen scavenging process may be used, either alone or in combination with a chilled liquid process. Bromine scavenging may be carried out in a bed containing solid CuBr or $MnBr_2$, either loaded on a support or used in powder form, to capture $Br_2$ from a gas stream that may also contain $H_2O$, $CO_2$, $O_2$, methane &/or $N_2$. In one embodiment of the invention, bromine scavenging is performed within a range of temperatures, e.g., from about −10° C. to about 200° C. When bromine scavenging is complete, molecular bromine may be released from the bed by raising the temperature of the bed to about 220° C. or higher, preferably above about 275° C. It is important that there be little if any $O_2$ in the bed during bromine release, as $O_2$ will oxidize the metal and, over time, reduce the bromine-scavenging capacity of the bed.

Hydrocarbon Product Separation

The processes of the present invention may produce a hydrocarbon product stream that may comprise water. For example, if a cataloreactant process is used to capture and regenerate HBr with the entire product stream passing through the cataloreactant, then water may be produced and pass along with the product stream. Alternatively, in a aqueous based hydrogen halide capture process, the product stream leaving the contact tower may contain water vapor that may be removed prior to passing the product hydrocarbons out of the process for sale. Once any water present in the product stream is removed, a product recovery system may be used to further separate and recycle the hydrocarbon product stream prior to the hydrocarbons leaving the system.

Figure 17:
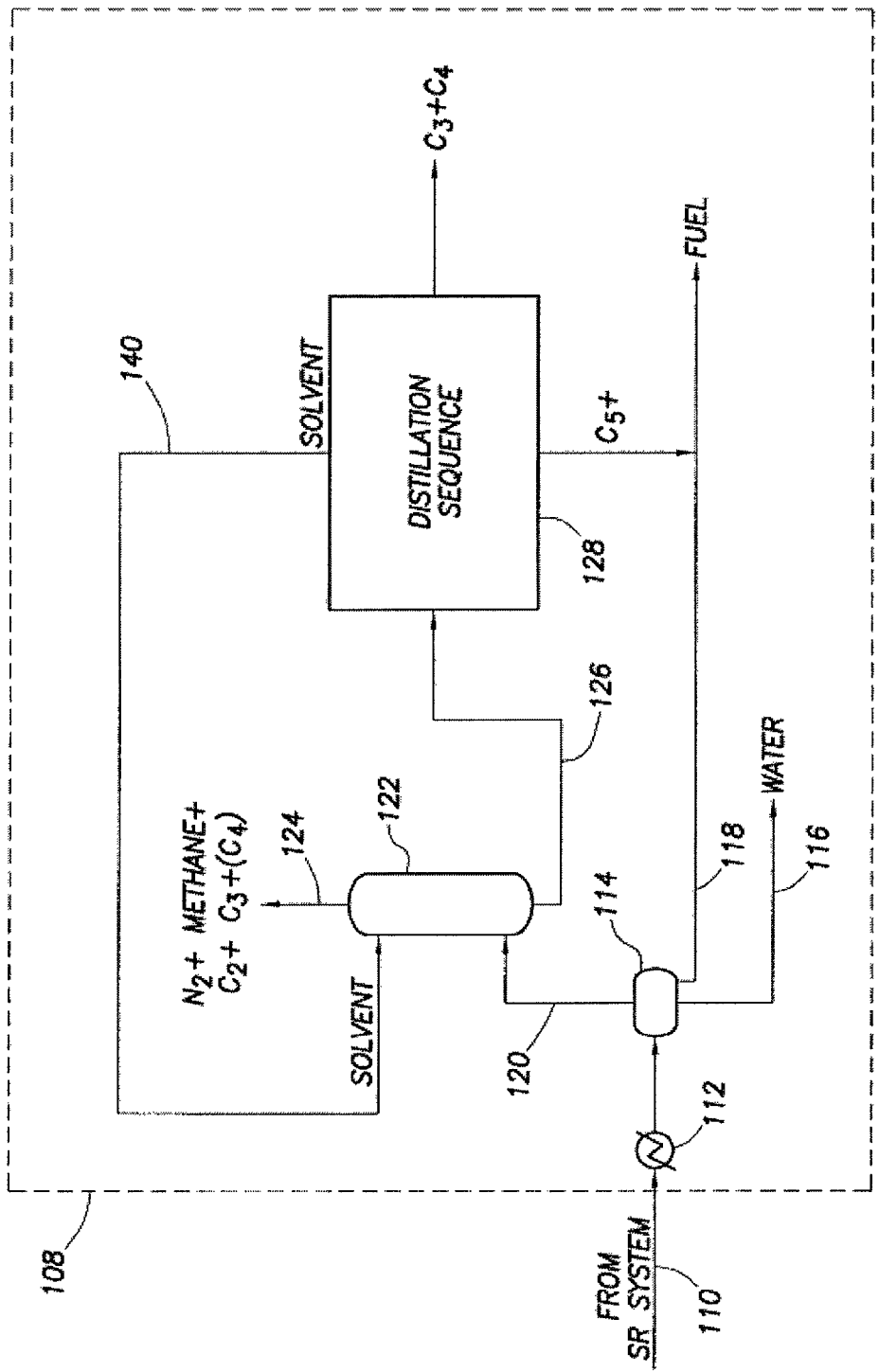
FIG. 17 is a schematic view of one embodiment of a product separation sub-system, for use in the practice of the invention.

In the product recovery system shown in FIG. 17, a product stream 110 leaving a hydrogen halide removal process (e.g., an aqueous absorption process, a solid reactant based capture process, etc.) may be substantially hydrogen halide free. The product stream 110 may be cooled using a heat exchanger 112 and partially condensed in a vessel 114 to yield a vapor phase and two immiscible liquid phases. The two liquid phases may be further separated to yield an aqueous phase stream 116, which may be primarily water with a small amount of dissolved hydrocarbons, and an organic phase stream 118 consisting of higher hydrocarbons.

Figure 18:
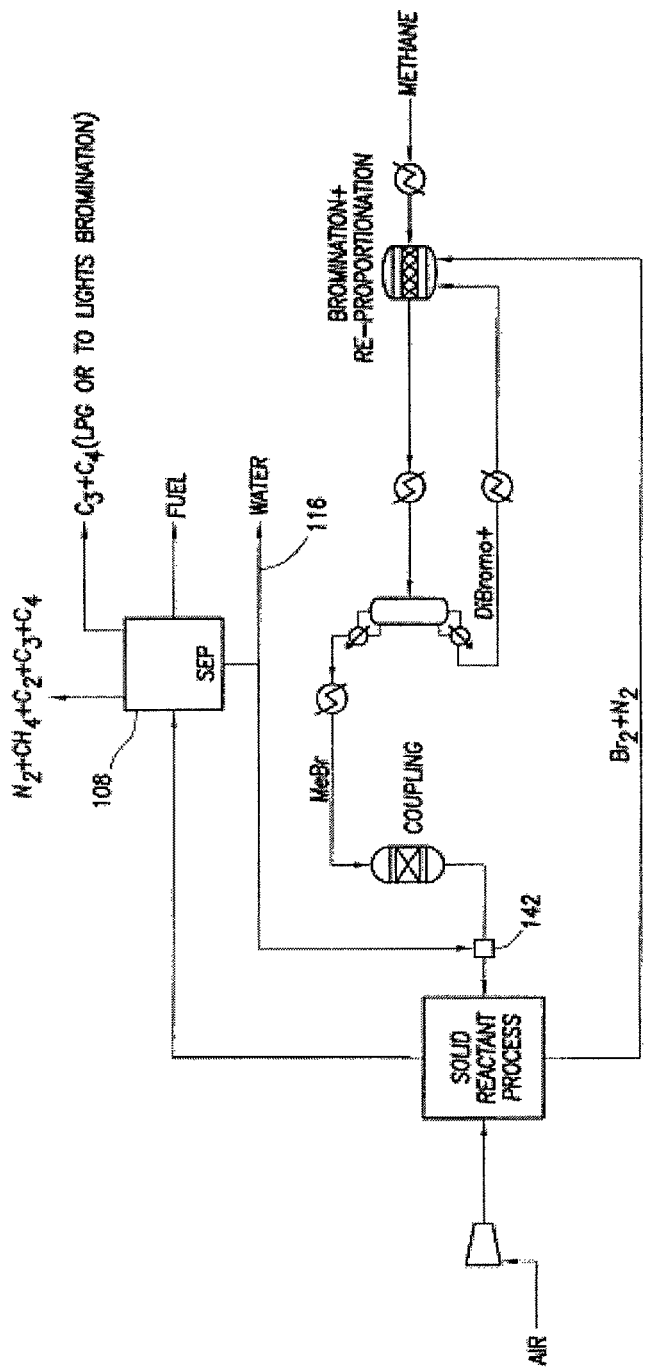
FIG. 18 is a schematic view of one embodiment of a product separation sub-system, for use in the practice of the invention.

The aqueous phase stream may exit the process or be utilized for various processes within the system. For example, the water may be used as a water source for another process within the system, such as a water source or makeup water source for an aqueous hydrogen halide absorption process. In another embodiment shown in FIG. 18, some of the water 116 recovered in the product recovery section 108 may be mixed with the coupling product stream in a quench column 142 and recycled to the hydrogen halide capture sub-process (e.g., a solid reactant HBr capture sub-process). In an embodiment, the quench column 142 may be a packed bed, spray tower, or equivalent unit operation. The amount of water recycled may be chosen such that the temperature of the mixed coupling product stream as well as the product gas stream leaving the hydrogen halide capture sub-process, may be above their respective dew points to insure that little to no liquid condensation occurs in the hydrogen halide capture sub-process. This embodiment may improve the economics of the entire process by reducing the cooling load in the hydrogen halide capture sub-process and transferring it to the product recovery system. This may result in a process with a lower capital cost as the materials of construction used for the heat transfer surfaces in the solid reactant sub-process may be significantly more expensive than those used in the product recovery system due to the presence of a hydrohalic acid. Further, the mixing may reduce the range of the temperature cycling in the hydrogen halide capture sub-process, which may be useful if a solid based reactant process is used in the hydrogen halide capture sub-process.

Referring to FIG. 17, the vapor stream 120 may be primarily composed of light gases such as $N_2$, methane, and other light hydrocarbons (e.g., $C_2$, $C_3$, $C_4$), and may be saturated with higher hydrocarbons (e.g., $C_5+$) and water. For embodiments using relatively large gas flowrates in the process, the vapor stream 120 may contain a significant fraction of the total liquid hydrocarbon product (e.g., $C_5+$). In some embodiments, the vapor stream 120 may then flow to an absorber 122 where a solvent may be used to absorb at least some of the higher hydrocarbons (e.g., $C_5+$). The solvent may be either a pure non-volatile hydrocarbon (e.g., $C_{12}H2_6$, mesitylene ($C_9H_{12}$), etc.) or a mixture of non-volatile hydrocarbons (e.g., diesel, a mixture of high boiling coupling products, etc.). In addition to absorbing at least some of the $C_5$ and higher hydrocarbons, the solvent may also absorb some of the $C_3$ and $C_4$ hydrocarbons, along with small amounts of the light hydrocarbons and gases. The gas stream 124 leaving the absorber 122 may contain most of the $N_2$, $CH_4$, $C_2$, and potential some $C_3$ and $C_4$. Stream 124 may be recycled if the amount of nitrogen is not excessive, or it may be flared, vented, recycled to the solid reactant sub process as a diluent for purposes of mitigating the temperature rise in the reactors, or otherwise used within the system, for example as a fuel stream. The liquid stream from the absorber 126 may pass to a separation sub-system 128, which may comprise one or more distillation sequences for recovering (a) the solvent for recycle to the absorber, (b) any $C_3$ and $C_4$ which may be further refined to LPG or recycled to lights bromination; and (c) any liquid hydrocarbon products (e.g., $C_5+$). While this separation process may be feasible at both low and high pressure, high pressure may be preferred in order to minimizing the solvent flowrate and use cooling water, rather than refrigeration, in any distillation columns condensers.

Figure 19:
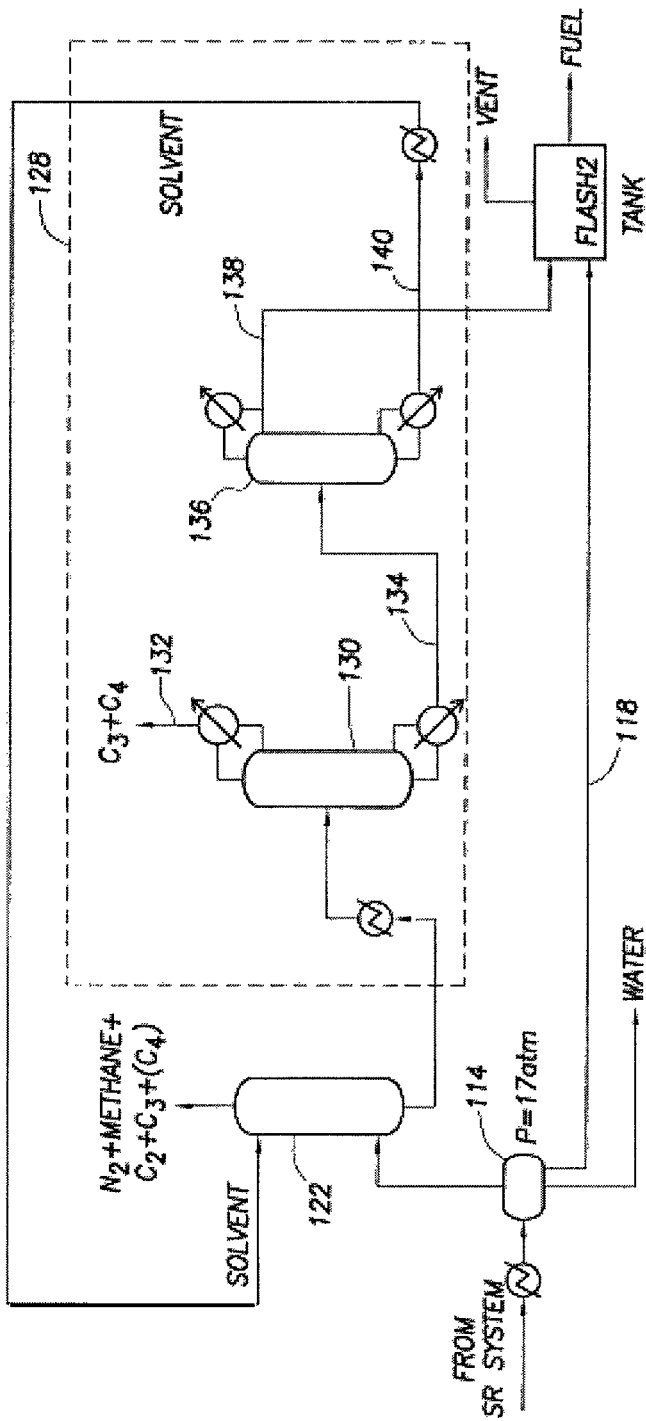
FIG. 19 is a schematic view of one embodiment of a product separation sub-system, for use in the practice of the invention.

An embodiment of a product recovery system with a distillation sequence is shown in FIG. 19. In this embodiment, two distillation columns may be used to sequentially recover the light hydrocarbons, the heavy hydrocarbons, and the solvent. In the first column 130 at least some of the light hydrocarbons comprising $C_3$ and $C_4$ may be separated as a vapor stream 132. The heavier hydrocarbons, which may have some $C_3$ and $C_4$ dissolved therein, may be passed to a second distillation column 136. The second distillation column 136 in this embodiment may separate any remaining product hydrocarbons as a liquid stream 138 and the solvent as a liquid stream 140. The liquid stream comprising the products 138 may be combined with the organic phase stream 118 from the initial separation vessel 114 in the product separation sub-process. The solvent stream 140 from the second distillation column 136 may be recycled back to the absorber 122. Distillation columns 130 and 136 may use a total or partial condenser such that the light hydrocarbon stream 132 and the product hydrocarbon stream 138 and may be either a vapor or liquid depending on the operating conditions. The operating pressures for the two distillation columns are selected so as to minimize the reboiler temperatures, minimize the use of any refrigerants in the column condensers, and maximize the opportunity for energy integration with other sub processes in the system. Using this process and diesel as a solvent, may result in a recovery of about 100% of the $C_5+$ hydrocarbons, about 50% of $C_4$, and about 17% of $C_3$. The resulting overall carbon efficiency may be up to about 60%.

Figure 20:
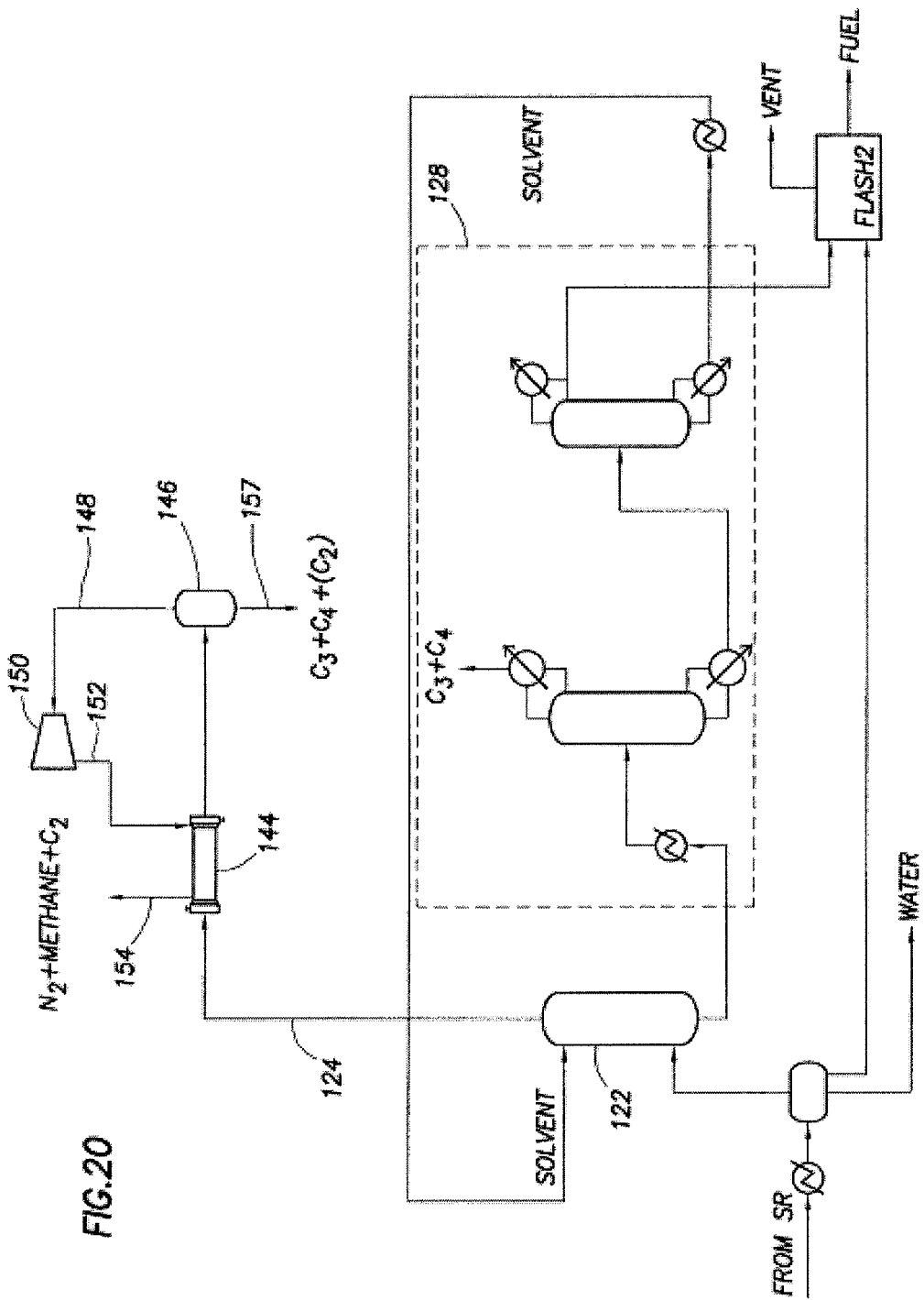
FIG. 20 is a schematic view of one embodiment of a product separation sub-system, for use in the practice of the invention.

Still another embodiment is shown in FIG. 20. In this embodiment, feedback expansion cooling may be used to obtain a high recovery of the light hydrocarbons. As used herein, the term "high recovery of the light hydrocarbons" may refer to a separation process capable of recovering more than about 60% of the $C_4$, and more than about 25% of the $C_3$ in the inlet stream. In this process, the stream 124 may first pass through a dehydration bed (not shown), and then leaving the absorber 122 may be at high pressure. In an embodiment, stream 124 may be at a pressure greater than about 10 atm, or alternatively greater than about 20 atm. This stream 124 may be cooled using a cold process stream in a heat exchanger 144 and phase separated in a separation vessel 146 to yield a liquid stream 157 comprising $C_3$ and $C_4$, along with some $C_2$ and $C_1$ and a vapor stream 148 containing $N_2$, $CH_4$ and $C_2$ hydrocarbons. The pressure of vapor stream 148 may be reduced from the high pressure to a much lower pressure using an expansion turbine 150, resulting in a significant decrease in the temperature of the stream. In an embodiment, the pressure of stream 148 may be reduced to between about 1 atm to about 5 atm in the expansion turbine 150. The resulting cold gas stream 152 may be used to cool the absorber exit gas stream 124 in the heat exchanger 144. The low pressure stream 154 may then be vented, recycled if the nitrogen content is not excessive, recycled to the solid reactant sub process as a diluent for purposes of mitigating the temperature rise in the reactors, or otherwise used within the process, for example as a fuel stream. The cold liquid stream 157 may also be used to provide some of the cooling required to cool the absorber exit stream 124 in heat exchanger 144. In another embodiment, especially in the case where the amount of the nitrogen in the absorber exit stream in not excessive, the expansion turbine 150 may be replaced by a Joule-Thompson valve. In yet another embodiment, the order of the expansion turbine, or the Joule-Thompson valve, and the separation vessel 146 may be reversed. The feedback cooling mechanism may allow the absorber gas outlet stream 124 to be cooled to a temperature low enough to condense at least some $C_3$ and $C_2$, without the use of refrigeration. Using this process, it may be possible to increase the overall recovery of any $C_4$ hydrocarbons to about 99%, any $C_3$ to greater than about 95%, and any $C_2$ to greater than about 30%. The resulting overall carbon efficiency may be up to about 75%.

Figure 21:
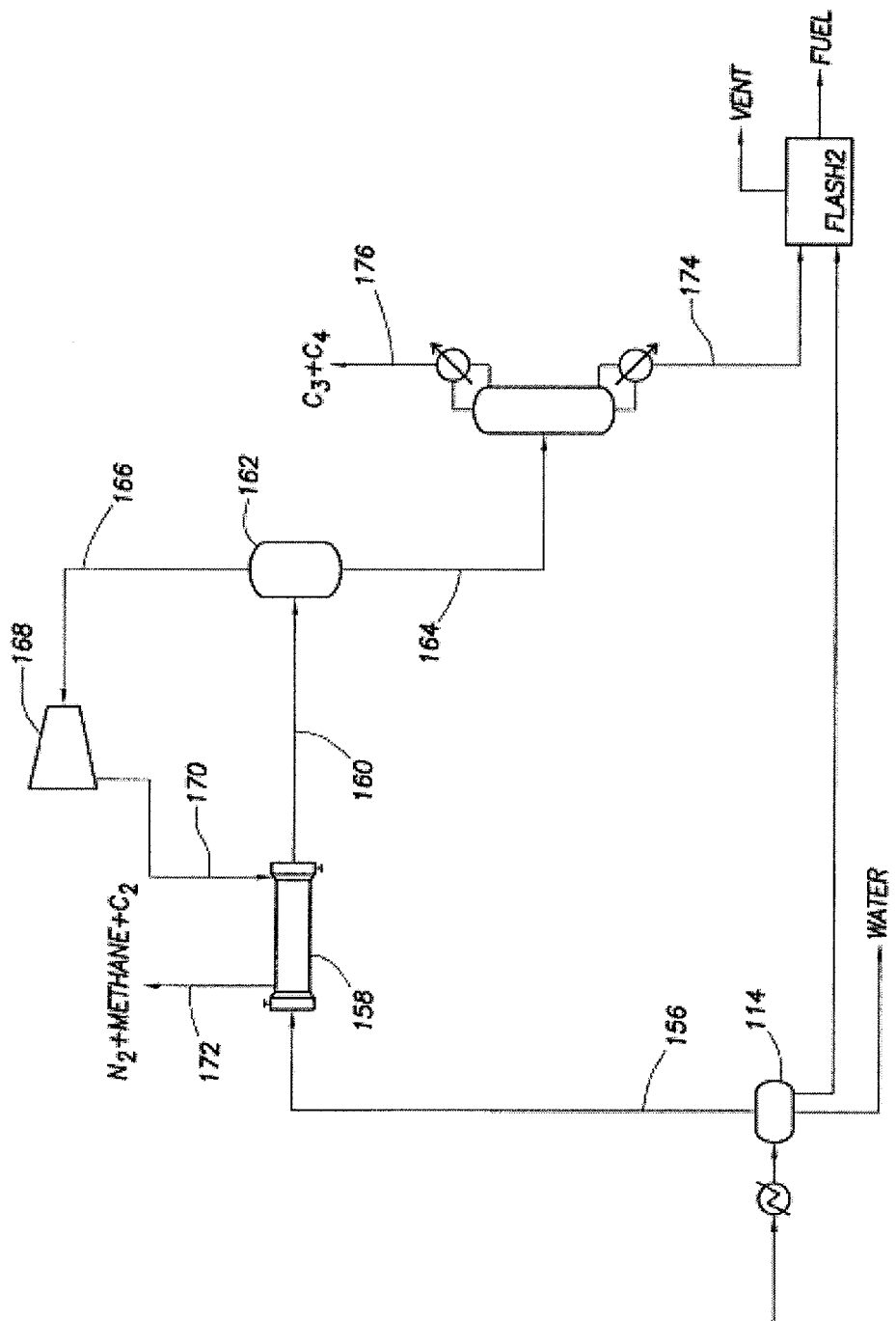
FIG. 21 is a schematic view of one embodiment of a product separation sub-system, for use in the practice of the invention.

Another embodiment of the product recovery sub-process is shown in FIG. 21. In this embodiment, feedback expansion cooling may be used to achieve the products separation without a solvent based absorption sub-process. The high pressure gas stream 156 leaving the flash drum 114 may first pass through a dehydration bed (not shown), and then may be cooled using a heat exchanger 158 and a flash drum 162 to recover a substantial portion of the $C_3+$ hydrocarbons in the liquid phase. In this embodiment, a network of heat exchangers and flash drums may be used to sequentially cool and separate the hydrocarbons. The plurality of heat exchangers and flash drums may be used to prevent heavy hydrocarbons from crystallizing in heat exchangers. The required cooling for this process may be provided by expansion cooling of the gas stream 166 leaving the heat exchanger/flash network, and optionally the heating and vaporization of the cold liquid stream 164. In the case where the amount of the nitrogen in the absorber exit stream 156 in not excessive, the expansion turbine 168 may be replaced by one or a series of Joule-Thompson valves. In addition, the order of some of the flash drums and the expansion turbine (or Joule Thompson valve) may be reversed. The resulting liquid stream 164 from the feedback expansion cooling process may be distilled in one or more columns to yield a liquid stream 174 comprising a hydrocarbon product (e.g., $C_5+$) and a vapor stream 176 comprising the LPG stream (e.g., $C_3$ and $C_4$).

In an embodiment, the product separation process may utilize some heat integration with other sub-processes in the system. For example, the separation process may not require any external heat as all of the energy required in the process may be provided by other process streams. One source of potential heat may be solid reactant sub-process if it is used to remove the hydrogen halide from the product stream.

Construction of Critical Process Elements with Unique Corrosion-Resistant Materials Corrosion induced by any halogen-containing process, whether in the condensed phase or the vapor phase, presents a significant challenge in the selection of durable materials for the construction of reactors, piping, and ancillary equipment. Ceramics, such as alumina, zirconia, and silicon carbides, offer exceptional corrosion resistance to most conditions encountered in the process described herein. However, ceramics suffer from a number of disadvantages, including lack of structural strength under tensile strain, difficulty in completely containing gas phase reactions (due to diffusion or mass transport along jointing surfaces), and possibly undesirable thermal transport characteristics inherent to most ceramic materials. Constructing durable, gas-tight, and corrosion resistant process control equipment (i.e. shell and tube type heat-exchangers, valves, pumps, etc.), for operation at elevated temperatures and pressures, and over extended periods of time, may likely require the use of formable metals such as Au, Co, Cr, Fe, Nb, Ni, Pt, Ta, Ti, and/or Zr, or alloys of these base metals containing elements such as Al, B, C, Co, Cr, Cu, Fe, H, Ha, La, Mn, Mo, N, Nb, Ni, 0, P, Pd, S, Si, Sn, Ta, Ti, V, W, Y, and/or Zr.

According to one embodiment of the invention, the process and subprocesses described herein may be carried out in reactors, piping, and ancillary equipment that are both strong enough and sufficiently corrosion-resistant to allow long-term continued operation. Selection of appropriate materials of construction depends strongly on the temperature and environment of exposure for each process control component.

Suitable materials for components exposed to cyclic conditions (e.g. oxidizing and reducing), as compared to single conditions (oxidizing or reducing), may differ greatly. Non-limiting examples of materials identified as suitable for exposure to cyclic conditions, operating in the temperature range of from about 150° C. to about 550° C., include Au and alloys of Ti and Ni, with the most suitable being Al/V alloyed Ti (more specifically Ti Grd-5) and Ni—Cr—Mo alloys with high Cr, low Fe, and low C content (more specifically ALL- COR®, Alloy 59, C-22, 625, and HX). Nonlimiting examples of materials identified as suitable for exposure to either acid halide to air, or molecular halogen to air cyclic conditions, in the temperature range about 150° C. to about 550° C., either acid halide to air, or molecular halogen to air include alloys of Fe and Ni, with the most suitable being alloys of the Ni—Cr—Mo, and Ni—Mo families. Nonlimiting examples of materials identified as suitable for single environment conditions, in the temperature range of from about 100° C. to about 550° C., include Ta, Au, and alloys of Fe, Co, and Ni. For lower temperature conditions (<about 280° C.), suitable polymer linings can be utilized such as PTFE, FEP, and more suitably PVDF. All materials may be used independently or in conjunction with a support material such as coating, cladding, or chemical/physical deposition on a suitable low-cost material such as low-alloy steels.

Additional Process Configurations

Figure 22:
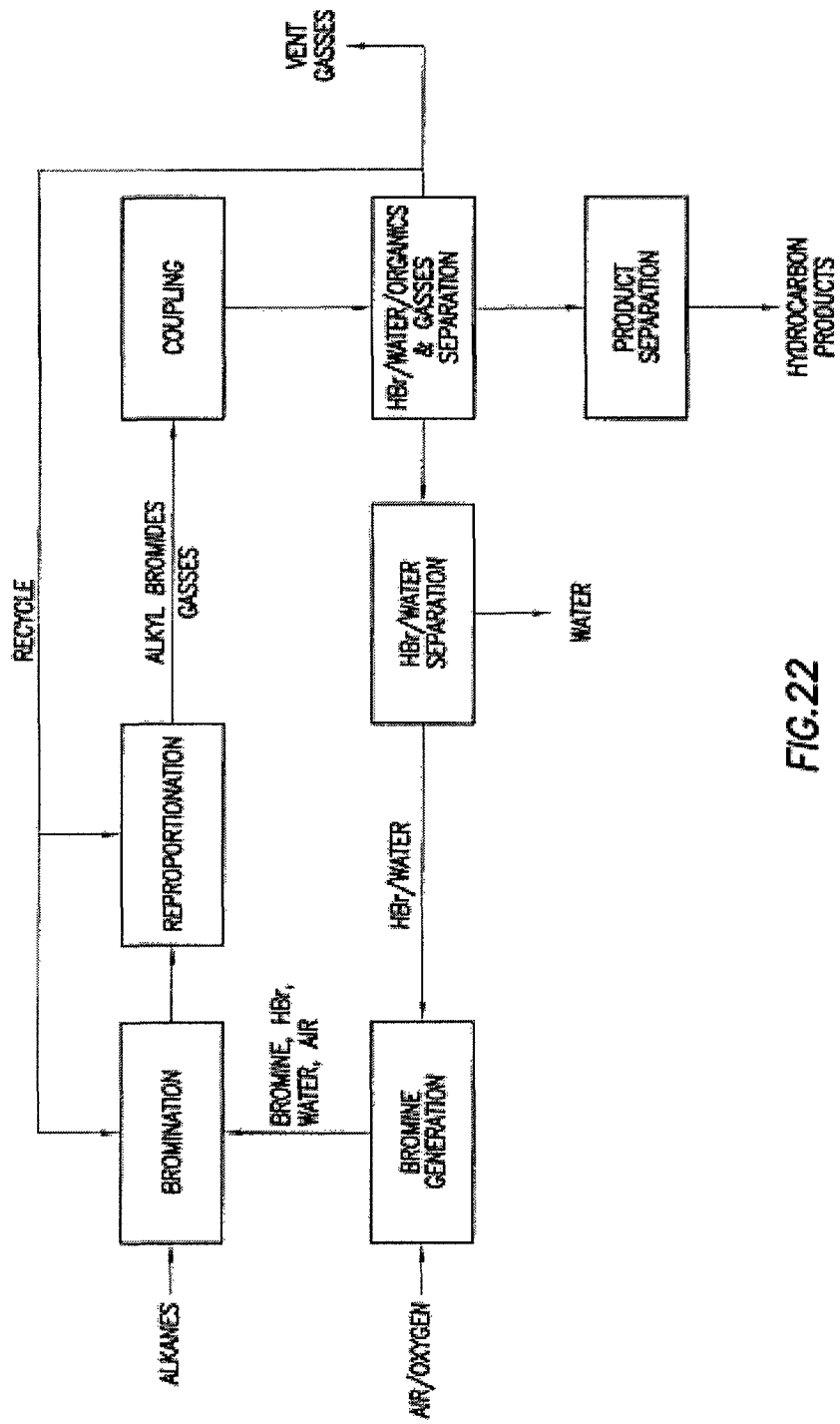
FIG. 22 is a simplified block diagram of one embodiment of a continuous process for converting alkanes into hydrocarbon products according to the invention, wherein water is separated from hydrocarbon products.

FIG. 22 schematically illustrates an alternate mode of operation for a continuous process for converting methane, natural gas, or other alkane feedstocks into higher hydrocarbons. Alkanes may be brominated in the bromination section in the presence of water formed during bromine generation, including recycled water. The bromination products may pass either through a reproportionation reactor or through the reproportionation section of the bromination reactor, where the light gases may be reproportionated to form olefins and alkyl bromides by using the polybromides as brominating agents. The reproportionation products, which include olefins, alkyl monobromides, some polybromides, and HBr, along with any unreacted alkanes, may then be sent to the coupling reactor. The coupling products may be sent to a vapor-liquid-liquid flash. Higher hydrocarbon products may be removed as an organic phase from the vapor-liquid-liquid flash, while aqueous HBr may be removed as the heavier phase. The gas stream from the flash may be sent to a separation system to recover methane and light gases, which may be recycled back to the bromination and reproportionation sections, respectively.

Nitrogen must be removed from the gas recycle stream if air is used as an oxidant in bromine generation. The aqueous HBr stream coming out of the vapor-liquid-liquid flash may be sent to the HBr/water separation system, where water may be recovered. The separation may be carried out in a distillation column, where pure water may be taken out as a distillate and the bottoms stream may be an aqueous solution of HBr (having a higher concentration of HBr than the feed to the distillation column). The aqueous HBr stream may be sent back to the bromine generation section, where bromine may be generated from aqueous HBr in the presence of air or oxygen.

Alternatively, extractive distillation may be used to separate HBr from water. The separated HBr may be sent to the bromine generation reactor and bromine may be generated from aqueous HBr in the presence of air or oxygen. Complete conversion of HBr is not necessary in the bromine generation reactor. Periodic decoking may be carried out for the bromination, reproportionation, and/or coupling reactors, with the bromine-containing decoking product stream being routed to the bromine generation reactor.

Figure 23:
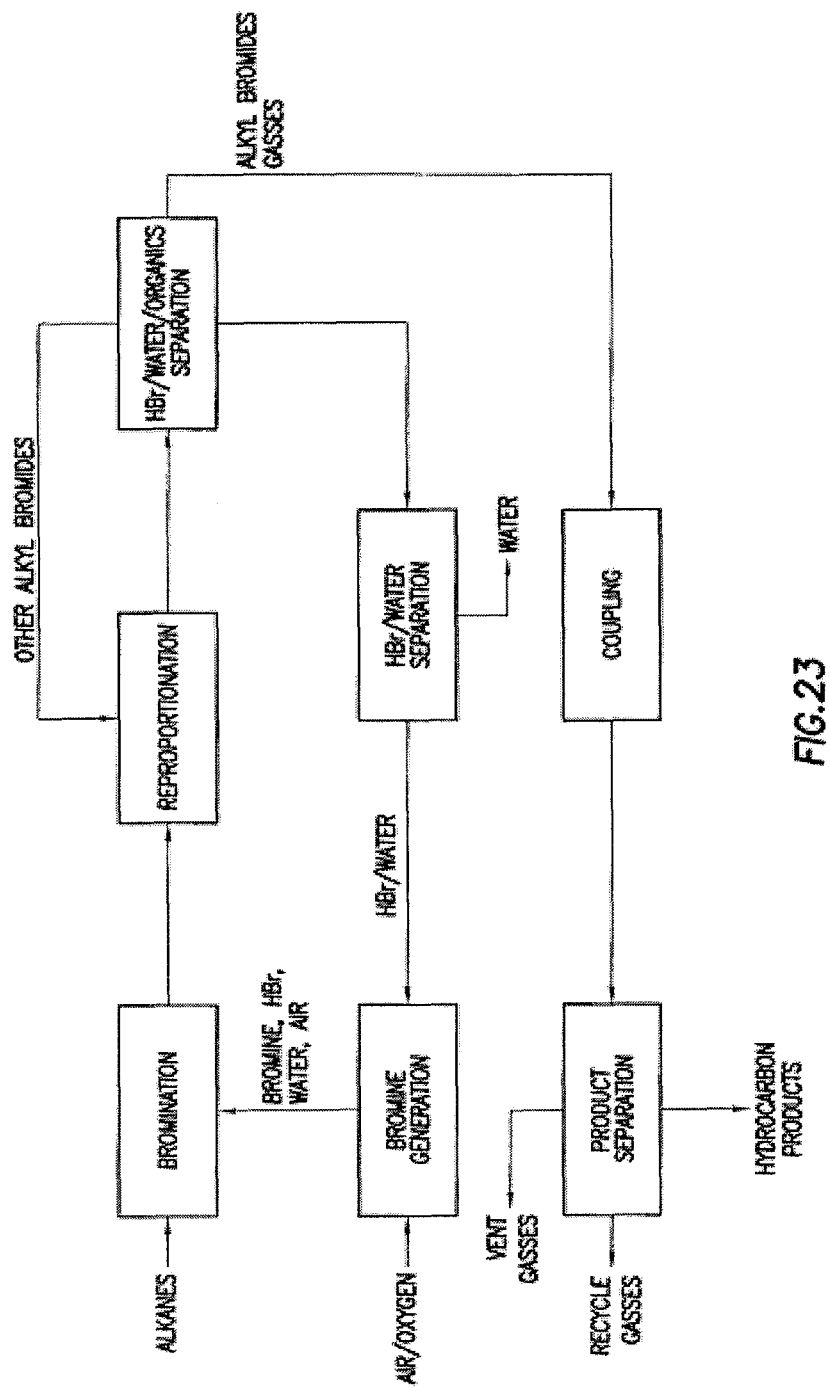
FIG. 23 is a simplified block diagram of one embodiment of a continuous process for converting alkanes into hydrocarbon products according to the invention, wherein water is separated after the alkane bromination step.

Another continuous process alternative is shown in FIG. 23. Alkanes may be brominated in the bromination section in the presence of water formed during bromine generation, including recycled water. The bromination products (which include monobromides and polybromides) may pass through either a reproportionation reactor or the reproportionation section of the bromination reactor, where the light gases may be reproportionated to form alkyl bromides, using the polybromides as brominating agents. The reproportionation products—alkyl monobromides, olefins, a small amount of polybromides, and HBr—and any unreacted alkanes may then be sent to a separation unit where aqueous HBr may be separated from the alkyl bromides. Monobromides in the alkyl bromide stream may be separated from the polybromides. The polybromides may be recycled to the reproportionation section where polybromides may react with the recycle gases to form olefins and monobromides.

The aqueous HBr separation from the alkyl bromides may be carried out in a distillation column coupled with a liquid-liquid flash. The alkyl bromide stream may contain HBr. The monobromides may be fed into the coupling section, and the products may be sent to a water absorption column where HBr produced in the coupling reactor is removed from the products and unconverted gas. The liquid outlet of the absorption column may be fed to a vapor-liquid-liquid flash separation unit, where higher hydrocarbon products may be removed as an organic phase and aqueous HBr may be removed as the heavier phase. The gas outlet from the absorption column may be sent to a separation system to separate methane from the light gases. The recovered methane may be recycled back to the bromination section, while the light gases may be recycled to the reproportionation section.

Nitrogen may be separated before the gases are recycled if air is used as an oxidant in bromine generation. The aqueous HBr stream from the vapor-liquid-liquid flash may be combined with the aqueous HBr stream from the alkyl bromide separation section and sent to the HBr/Water separation system. The separation may be carried out in a distillation column, where pure water may be taken out as a distillate and the bottoms stream may be an aqueous solution of HBr having a higher concentration of HBr compared with the feed to the distillation column. The aqueous HBr stream may be sent back to the bromine generation section, where bromine may be generated from aqueous HBr in the presence of air, oxygen or enriched air.

Alternatively, extractive distillation may be used to separate HBr from water. The separated HBr may be sent to the bromine generation reactor, where bromine may be generated from aqueous HBr in the presence of air, oxygen, or enriched air. Complete conversion of HBr to bromine is not required during bromine generation. Periodic decoking of the bromination, reproportionation and coupling reactors may be carried out, with the bromine-containing decoking product stream being routed to the bromine generation reactor.

Another continuous process configuration is shown in FIG. 3. In this embodiment a non-redox active solid reactant may be used to capture and regenerate the hydrogen halide generated in the halogenation reactor and the coupling reactor. In this embodiment, an alkane feedstock stream 41 may be brominated in a bromination reactor 43. The bromination products 44 may be separated in a separator 45 to allow the monobrominated stream 47 to pass to the coupling reactor 48, while the polybrominated stream 46 may be recycled to a reproportionation reactor (not shown) or a reproportionation section of the bromination reactor 43. If a separation and reproportionation scheme is used, the light gases may be reproportionated to form olefins and alkyl bromides through the use of the polybrominated species as brominating agents. The reproportionated products, which may include olefins, alkyl monobromides, some polybromides, and HBr, along with any unreacted alkanes, may then be sent to the coupling reactor 48. The coupling reactor products 49 may then be sent to an HBr capture reactor 55 that contains a solid reactant. The solid reactant may capture the HBr by forming a metal bromide corresponding to the metal-oxide solid reactant. The product stream 50 from the HBr capture reactor 55 may be substantially free of HBr and may pass to a products separation unit 51. The product stream 50 may be dehydrated to remove any water 54, such as any water produced during the reaction of the HBr with the solid reactant. The product stream 50 may be further separated to allow methane 53 or other light hydrocarbons to be separated from a heavier products stream 52 and be recycled to the inlet of the process or used as fuel.

The halogen capture process shown in the embodiment depicted in FIG. 3 may generate a metal bromide 56. The metal bromide 56 may be regenerated to the original metal oxide solid reactant in a regeneration reactor 57 through the introduction of air or oxygen 58. The air or oxygen 58 may react with the metal bromide 56 entering the regeneration reactor 57 to generate a regeneration products stream 59 containing elemental bromine along with any inert gases contained in the air or oxygen containing stream 58. The regeneration product stream 59 may be separated in a separator 60 in order to remove and any inert gases 61 from the process, such as nitrogen if air is used as the oxygen source. The separator 60 may also result in an elemental bromine stream 62 that may be passed back to the bromination reactor 43 in order to brominate the incoming alkane feedstock 41, recycled hydrocarbons, or any combination thereof. The regenerated metal oxide solid reactant may be transported back to the HBr capture reactor 55 through recycle line 63. The metal bromide conversion to metal oxide and regeneration cycle in the embodiment shown in FIG. 3 may be carried out in any type of reactor capable of containing a solid reactant material. Reactor configurations that may be used include, but are not limited to, fixed beds, fluidized beds, and moving beds.

In another embodiment, the solid reactant may be contained in three or more alternating fixed bed reactors in parallel (not shown). At any given time, one of the reactors is on-line for hydrogen halide capture/neutralization; one of the reactors is on-line for elemental halide regeneration; while the remaining reactors are offline for purge, and cooling/heating of the fixed bed reactors to the desired capture and regeneration temperatures. In this manner the overall process can be operated continuously without interruption.

In an embodiment illustrated in FIG. 3, the coupling reactor 48, which may contain a coupling catalyst, may be carried out in any type of reactor. Reactor configurations that may be used to create higher hydrocarbons include, but are not limited to, fixed beds, fluidized beds, and moving beds. In an embodiment, the coupling reactor 48 may be contained in a plurality of alternating fixed bed reactors (not shown). While a given reactor is off-line for decoking, the overall process can, nevertheless, be operated without interruption by using a reserve reactor, which is arranged in parallel with its counterpart reactor. For example, twin coupling reactors may be utilized, with process gasses being diverted away from one, but not both, reactors.

In an embodiment illustrated in FIG. 3, the coupling reactor 48 may be a moving bed reactor or a fluidized bed reactor. In this embodiment, the coupling reactor 48 may receive a regenerated coupling catalyst 64 and contact the regenerated coupling catalyst 64 with a brominated hydrocarbon stream 47. Coke may be produced during the coupling reaction resulting in decreased reactivity of the coupling catalyst. In order to restore the catalytic reactivity of the coupling catalyst, a decoking process may be carried out in a decoking reactor 65 that may receive the coked catalyst stream 68 and air or oxygen 66 to facilitate the removal of the coke from the coupling catalyst. The decoking products stream 67, which may contain bromine, may be routed to the bromine generation reactor 57. The regenerated coupling catalyst 64 may be transported back to the coupling reactor 48 to complete the cycle.

Figure 24:
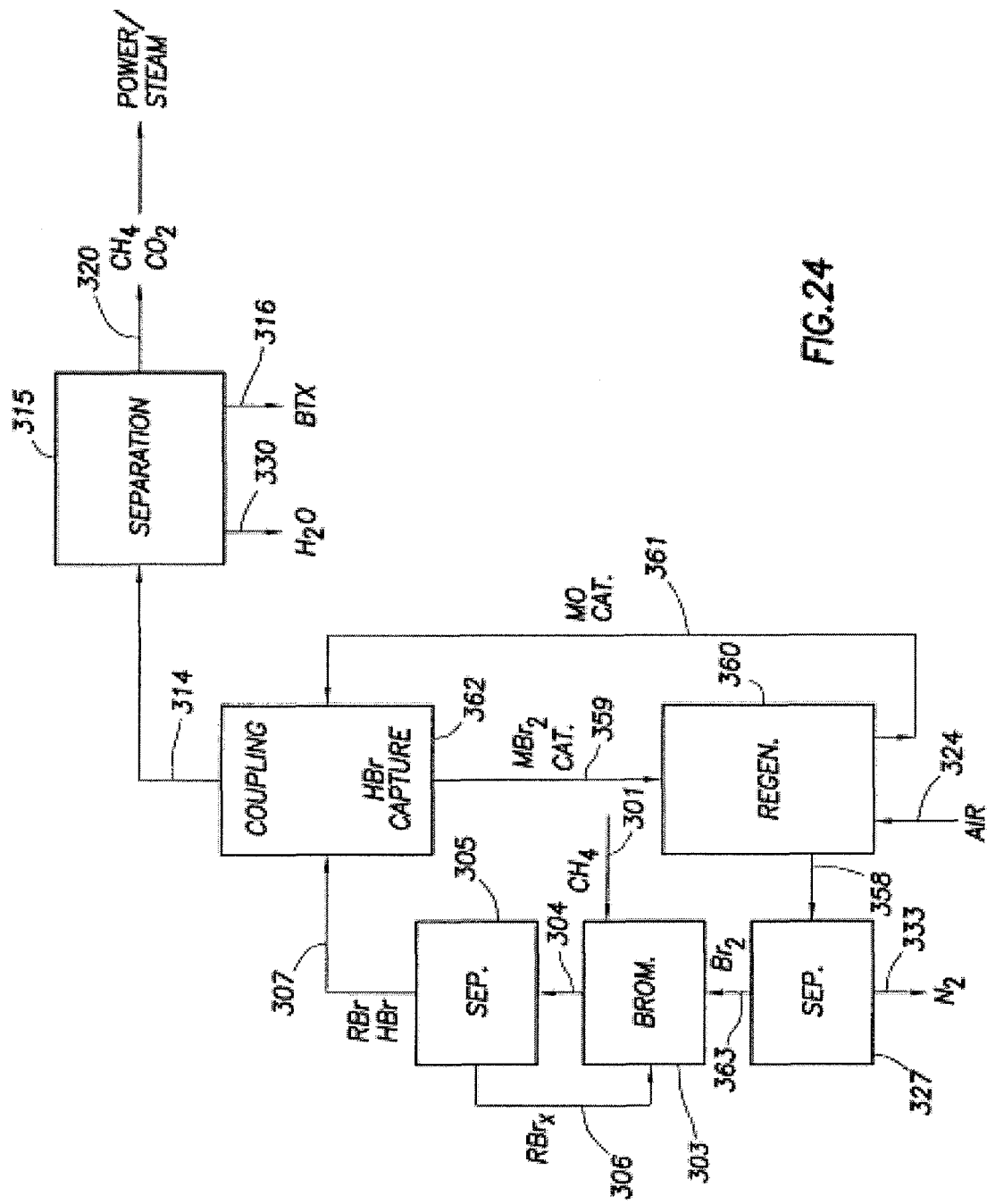
FIG. 24 is a simplified block diagram of one embodiment of a continuous process for converting alkanes into hydrocarbon products according to the invention, wherein a cataloreactant is used.

Still another continuous process configuration is shown in FIG. 24. In this embodiment, a single reactor may be used to couple the alkyl bromide reactants and capture the HBr generated during the bromination reaction and the coupling reaction. In this embodiment, the catalyst used may act as both a coupling catalyst and solid reactant for capturing HBr, which may be a non-redox active solid reactant. For example, a alumino silicate zeolite catalyst with wet-impregnated metal oxide may be used. In another embodiment, separate materials may be used. For example, a zeolite without a metal oxide may be used to act as a catalyst for coupling and a separate metal oxide doped zeolite may be used to capture HBr. This embodiment may allow the separate materials to incorporated into the reactor as a uniform mixture of the materials, or allow for layering of the materials to form zones within the reactor. In an embodiment in which the reactor is a fluidized bed or moving bed reactor and separate materials are used to couple the alkyl bromides and capture the produced HBr, the particles may be similarly sized to avoid separation of the material into distinct phases during transport or use. The catalyst may regenerated in the regeneration section by oxidation of coke, and the solid reactant may be regenerate to release bromine in the reaction of the metal bromide with air or oxygen.

In the embodiment shown in FIG. 24, an alkane feedstock stream 301 may be brominated in a bromination reactor 303. The bromination products 304 may be separated in a separator 305 to allow the monobrominated stream 307 to pass to the coupling reactor 309, while the polybrominated stream 306 may be recycled to a reproportionation reactor (not shown) or a reproportionation section of the bromination reactor 303. If a separation and reproportionation scheme is used, the light gases may be reproportionated to form olefins and alkyl bromides through the use of the polybrominated species as brominating agents. The reproportionated products, which may include olefins, alkyl monobromides, some polybromides, and HBr, along with any unreacted alkanes, may then be sent to the coupling reactor 362 that may also contain a solid reactant for capturing HBr.

In the embodiment shown in FIG. 24, the coupling reactor may also contain a solid reactant for capturing any HBr in the incoming brominated stream and any HBr produced during the coupling reaction. The product stream from the coupling reactor 362 may be substantially free of HBr and may pass to a products separation unit 315. The products may be dehydrated to remove any water 330 contained in the system, such as the water produced during the reaction of the HBr with the solid reactant. The products 314 may be further separated to allow methane 320 or light hydrocarbons to be recycled to the inlet of the process or used as fuel.

In an embodiment in which the coupling reactor also contains a solid reactant for capturing HBr, the coupling reaction may deactivate the coupling catalyst and convert the solid reactant to a metal bromide phase solid reactant. The coupling catalyst may be deactivated due to a number of reasons including, but not limited to, coke formation on the catalyst or within the interstitial space between the catalyst particles.

In order to regenerate the coupling catalyst and the solid reactant, the material may be regenerated in a regeneration reactor 360 through the introduction of air or oxygen 324. The air or oxygen may react with any coke to generate $CO_2$ along with a number of other combustion products including brominated species, and the metal bromide solid reactant may react to form a metal oxide and elemental bromine. The product stream 358 from the regeneration reactor may be separated in a separator 327 in order to remove and any inert gases 333 from the process, such as nitrogen if air is used as the oxygen source. The $CO_2$ generated in the regeneration reactor may be removed in separator 327 or may pass through the process to be removed in the products separation reactor 315. The separator 327 may also result in an elemental bromine stream that may be passed back to the bromination reactor 303 in order to brominate the incoming alkane feedstock, recycled hydrocarbons, or any combination thereof.

In the embodiment shown in FIG. 24, the coupling reaction, HBr capture reaction, and regeneration reaction cycle may be carried out in any type of reactor capable of containing a solid coupling catalyst and solid reactant material. Reactor configurations that may be used include, but are not limited to, fixed beds, fluidized beds, and moving beds.

In another embodiment, the solid reactant may be contained in three or more alternating fixed bed reactors in parallel (not shown). At any given time, one of the reactors is on-line for hydrogen halide capture/neutralization; one of the reactors is on-line for elemental halide regeneration; while the remaining reactors are offline for purge, and cooling/heating of the fixed bed reactors to the desired capture and regeneration temperatures. In this manner the overall process can be operated continuously without interruption.

In an embodiment illustrated in FIG. 24, a moving bed reactor configuration or a fluidized bed reactor configuration may be utilized where the solid reactant is cyclically transported from the coupling reactor 362 to the regeneration reactor 360 and back. In this embodiment, the coupling reactor 362 may receive a regenerated material stream 361 comprising a regenerated coupling catalyst, solid reactant, or combination thereof and contact the regenerated material with a brominated hydrocarbon stream 307. The coupling catalyst may be deactivated in the coupling reactor and the solid reactant may be converted to a metal bromide in a reaction with any HBr present. The deactivated coupling catalyst and the metal bromide solid reactant may exit the reactor as a deactivated catalyst stream 359, which may be transported to a regeneration reactor 323 to be regenerated and decoked with an air or oxygen stream 324. After regeneration, a regenerated catalyst stream 361 may be transported back to the coupling reactor 350 to complete the cycle.

Figure 25:
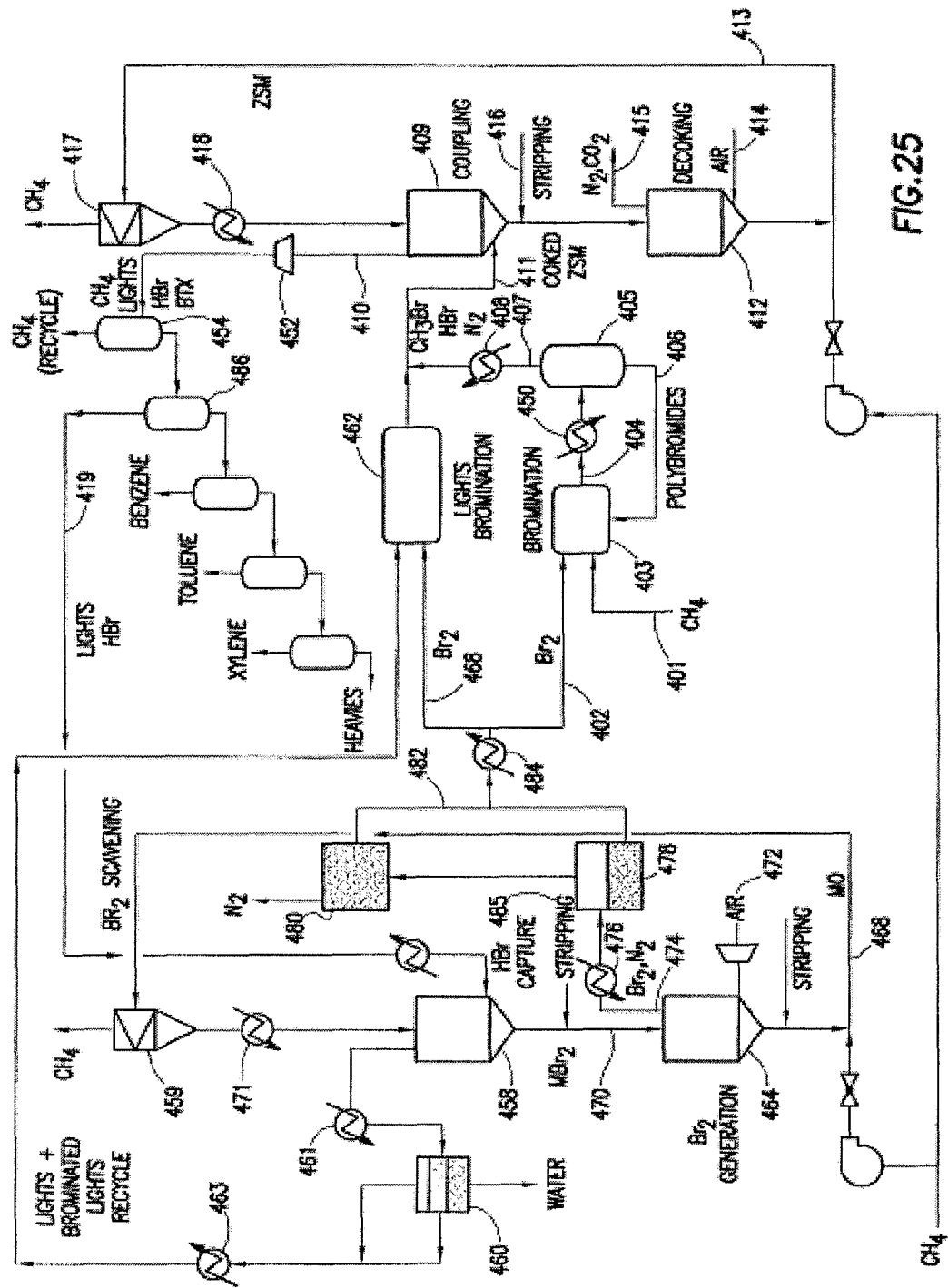
FIG. 25 is a schematic view of one embodiment of a continuous process for converting methane or natural gas into hydrocarbon chemicals according to the invention.

In an embodiment shown in FIG. 25, a redox active solid reactant material may be used in a process for making higher hydrocarbons. In this embodiment, natural gas or another hydrocarbon feedstock and molecular bromine may be carried by separate lines 401, 402 into a heated bromination reactor 403 and allowed to react. Products (e.g., HBr, alkyl bromides, olefins, etc.), and possibly unreacted hydrocarbons, may exit the reactor and may be carried by a line 404 into a first separation unit 405, where monobrominated hydrocarbons and HBr may be separated from polybrominated hydrocarbons. The products may pass through a heat exchanger 450 between the bromination reactor 403 and the first separation unit 405 depending on the product stream temperature desired in the first separation unit 405. The polybromides may be carried by a line 406 back to the bromination reactor, where they may undergo "reproportionation" with methane and/or other light hydrocarbons, which may be present in the natural gas and/or introduced to the bromination reactor as described below. For large scale production of higher hydrocarbons, additional separation units may be employed, which may further purify the feed stream to the coupling reactor by separating and recycling the polybromides, thereby reducing the amount of coke and the overall bromine requirement.

In reference to FIG. 25, unreacted hydrocarbon feedstock, HBr, monobromides, and (optionally) olefins formed in the bromination reactor 403 may be carried by a line 407, through a heat exchanger 408, and enter a heated coupling reactor 409, where at least some of the monobromides (and, optionally, any olefins present) may react in the presence of a coupling catalyst to form higher hydrocarbons. The coupling reactor products stream comprising HBr, higher hydrocarbons, and (possibly) unreacted hydrocarbons and alkyl bromides may exit the coupling reactor and be carried by a line 410, through an optional compressor 452, if required, and enter a products separation train. Any number or type of separation units, which may employ pressure- or temperature-swing adsorption, membrane-based separation, cryogenic distillation that may be preferable for large scale production, or another suitable separation technology, may be used to generate a desired product distribution. Unreacted methane may be separated in a first products separation unit 454 to allow the methane to be recycled to the inlet of the process or used for fuel. A second products separation unit 456 may be employed to separate other light hydrocarbons and HBr from the products stream. One or more additional product separation units as described above may be used to yield final hydrocarbon products.

In reference to FIG. 25, the coupling reactor 409 may have a fixed bed, circulating moving bed, or circulating fluidized bed reactor configuration. In an embodiment, a fixed bed configuration (not shown in FIG. 25) may be used to perform the coupling reaction. In this embodiment, a plurality of reactors may be used with the brominated product stream 411 being diverted from one reactor while the other may receive air or oxygen to decoke the coupling catalyst. The process flows may then be cycled so that the coupling process may be operated continuously.

In an embodiment shown in FIG. 25, the coupling reactor 409 may be operated using a moving bed reactor configuration or a fluidized bed reactor configuration. In this embodiment, the coupling catalyst may be cyclically transported between the coupling reactor 409 and a decoking reactor 412. In this embodiment, coupling reactor 409 may receive a regenerated coupling catalyst 413 and contact the regenerated coupling catalyst with the brominated products stream 411 to form a coupling reactor products stream 410. The coupling catalyst may form at least some coke during the coupling reaction. The coked coupling catalyst may exit the coupling reactor and be transported to the decoking reactor 412 where air or oxygen 414 may be introduced to decoke at least a portion of the coupling catalyst. A stripping gas stream 416 (e.g., steam, hydrocarbons, etc.) may be introduced into the coked coupling catalyst as it is transported between the coupling reactor 409 and the decoking reactor 412 to remove any hydrocarbons from the coked coupling catalyst prior to the coked coupling catalyst being contacted with a stream containing air or oxygen 414. Gas stripping may be done by a discrete piece of hardware, or it may be part of the pneumatic transport system between zones. The decoking reaction may produce carbon dioxide as any coke and remaining hydrocarbons adsorbed on the coupling catalyst combusts (i.e., oxidizes). These combustion products may pass out of the decoking reactor 412 along with any inert components of the air or oxygen stream, such as nitrogen if air is used, in a decoking products stream 415. The decoking products stream may be sent to the regeneration reactor 464 or another scrubbing section in order to recover any bromine adsorbed on the coked coupling catalyst. The regenerated coupling catalyst 413 may be transported back to the coupling reactor 409 to complete the cycle. A coupling catalyst vessel 417 may be used to hold the decoked coupling catalyst from the decoking reactor 412 before being transported to the coupling reactor 409. A heat exchanger 418 may be used to heat or cool the coupling catalyst to a desired temperature at which the coupling reaction may occur.

As shown in FIG. 25, the HBr and light hydrocarbons may be carried by line 419 into an HBr capture reactor 458 after the HBr and the light hydrocarbons are separated from the hydrocarbon products in the products separation train. The conditions of the HBr capture reactor containing a redox active solid reactant may result in a metal bromide being generated along with bromine, which may react with the light gases to produce alkyl bromides. Using cobalt oxide, a redox active solid reactant, as an example, the following overall reaction occurs during HBr capture:

$$Co_3O_4 + 8HBr \rightarrow 3CoBr_2 + Br_2 + 4H_2O \quad \text{(Equation 26)}$$

$$C_2H_6 + Br_2 \rightarrow C_2H_5Br + HBr \quad \text{(Equation 27)}$$

$$C_3H_8 + Br_2 \rightarrow C_3H_7Br + HBr \quad \text{(Equation 28)}$$

Alkyl bromides from the HBr capture reactor 458 may pass through a heat exchanger 461, if necessary, before being separated from water by liquid-liquid or liquid-liquid-vapor phase separation 460 and sent to a lights bromination reactor 462, which may also receive additional bromine from line 468. Heat exchanger 463 may be a heater or cooler, as necessary, to bring the stream from the separator 460 to the appropriate temperature for the lights bromination reactor 462. The products of the lights bromination reactor 462 may be combined with the products of the bromination reactor 403 before entering the coupling reactor 409.

As shown in FIG. 25, the metal bromide produced in the HBr capture reactor 458 may be regenerated with air or oxygen to regenerate the original solid reactant materials. In an embodiment, the metal bromide may be sent to the bromine regeneration reactor 464, where the following overall reaction occurs:

$$3CoBr_2 + 2O_2 \rightarrow Co_3O_4 + 3Br_2 \quad \text{(Equation 29)}$$

The products stream 474 from the regeneration reactor may contain bromine and any inert gases contained in the air or oxygen stream 472, such as nitrogen. The products stream 474 may pass through a heat exchanger 476 to cool the stream prior to entering a separator 478. In an embodiment, the bromine may be separated from any other components using liquid-vapor separation, for example, using a flash tank. As the bromine may have a boiling point well below that of other components of the stream, the bromine may condense and form a liquid phase. The liquid phase may be drawn off and passed through a heat exchanger 484 before being routed to the lights bromination reactor 462, the bromination reactor 403, or both. In another embodiment, the liquid bromine may be passed to the reactor and vaporized within the reactor vessels. The vapor stream leaving the liquid vapor separator 478 may pass through a bromine scavenging unit 480 prior to exiting the system. Any bromine recovered in the bromine scavenging unit may be recycled to the system, such as for example passing through line 482 to be combined with the liquid bromine stream for use in the bromination reactors.

A fixed bed, circulating moving bed, or circulating fluidized bed reactor configuration may be used for HBr capture and bromine regeneration. In an embodiment, a fixed bed configuration (not shown in FIG. 25) may be used to perform HBr capture and regeneration. In this embodiment, a plurality of reactors may be used with the stream containing the light hydrocarbons and HBr from the products separation train being diverted from one reactor while the other may receive air or oxygen to regenerate the solid reactant. The process flows may then be cycled so that the process may be operated continuously.

In an embodiment shown in FIG. 25, a moving bed reactor configuration or a fluidized bed reactor configuration may be utilized where the solid reactant is physically cycled between the HBr capture reactor 458 and the regeneration reactor 464. In this embodiment, an HBr capture reactor 458 may receive a regenerated solid reactant 468 and contact the regenerated solid reactant with the stream containing the light hydrocarbons and HBr 419 from the products separation train. The regenerated solid reactant 468 may be converted to a metal bromide in the HBr capture reactor 458 and may produce water as a byproduct. Any hydrocarbons entering the HBr capture reactor 458 may react with any bromine generated by a redox active solid reactant. The solid reactant that is converted in the HBr capture reactor 458 may exit the HBr capture reactor as a metal bromide stream 470. The metal bromide stream 470 may be transported to a regeneration reactor 464 where air or oxygen 472 may be introduced to regenerate at least a portion of the metal bromide to the original solid reactant. A stripping gas stream 485 may be introduced into the metal bromide as it is transported between the HBr capture reactor 458 and the regeneration reactor 464 to remove any lights or brominated lights from the metal bromide prior to the metal bromide being contacted with a stream containing air or oxygen 472. The regenerated solid reactant stream 468 may be transported back to the HBr capture reactor 458 to complete the cycle. A solid reactant vessel may be used to hold the regenerated solid reactant 468 from the regeneration reactor 464 before being transported to the HBr capture reactor. A heat exchanger 471 may be used to heat or cool the regenerated solid reactant to a desired temperature at which the HBr capture reaction may occur.

In the embodiment shown in FIG. 25, a process gas stream may be used pneumatically transport a catalyst or solid reactant stream if a moving bed or fluidized bed reactor design is used. For example, the process gas stream may be a portion of the hydrocarbon stream used as the input into the process. In another embodiment, an inert gas such as nitrogen may be used to transport the catalyst or solid reactant. After the material is transported to the desired location, the process gas stream may be recycled within the process, used as a feed to the process, used as a fuel stream, vented, or any combination thereof.

Figure 26:
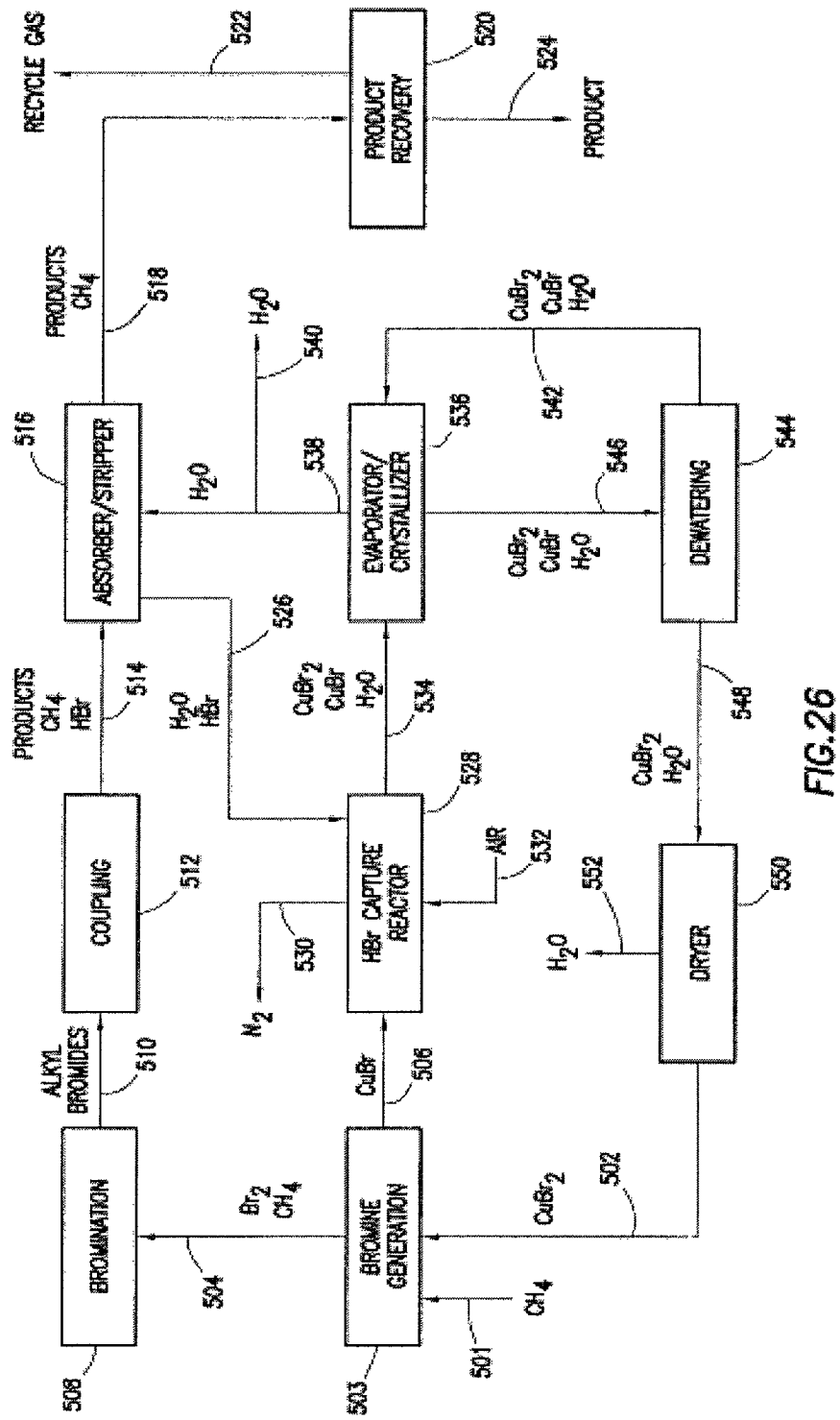
FIG. 26 is a simplified block diagram of one embodiment of a continuous process for converting alkanes into hydrocarbon products according to the invention, wherein a copper bromine capture agent is used.

As shown in FIG. 26, the HBr to $Br_2$ conversion process using copper bromides may be applied to a process for the conversion of alkanes to higher liquid hydrocarbons. In an embodiment, natural gas or another hydrocarbon feedstock may be carried by line 501 into a heated bromine generation reactor 503. Solid $CuBr_2$ may be carried by line 502 into the bromine generation reactor 503 where it may be heated to about 275° C. or higher to release elemental bromine, resulting in the conversion of the $CuBr_2$ to CuBr. The bromine generation reactor products may include a vapor stream 504 comprising the entering hydrocarbon feedstock and the elemental bromine and a solids stream 506 comprising CuBr and any unconverted $CuBr_2$. The solids stream may pass to a HBr capture reactor, as discussed in more detail below. In an embodiment, the bromine generation reactor 503 may be, without limitation, a moving bed reactor or a fluidized bed reactor.

The vapor stream 504 may pass to a bromination reactor 508 where the hydrocarbon feedstock may be allowed to react with the elemental bromine to form various bromination products including, but are not limited to, HBr, alkyl bromides, olefins, and possibly unreacted hydrocarbons. In an embodiment, a reproportionation scheme may be used with the bromination reactor as described in more detail herein. In this embodiment, The bromination products may exit the reactor and be enter a separation unit where monobrominated hydrocarbons and HBr may be separated from polybrominated hydrocarbons. In some embodiments, the polybromides may be carried back to the bromination reactor, where they may undergo reproportionation with methane, other light hydrocarbons, or a combination thereof, which may be present in the natural gas and/or introduced to the bromination reactor. In another embodiment, a separate reactor may be utilized for bromination of any $C_2$ or heavier hydrocarbons. In some embodiments, the bromine generation reactor and the bromination reactor may take place in the same vessel, which may be operated as a moving bed or fluidized bed reactor.

In the embodiment shown in FIG. 26, any unreacted hydrocarbon feedstock, HBr, monobromides, and any olefins formed in the bromination reactor may be carried by a line 510 to coupling reactor 512, where the monobromides, olefins, or any combination thereof may react in the presence of a coupling catalyst to form higher hydrocarbons. In an embodiment, a heat exchanger may be used to adjust the temperature of the brominated products stream 510 to a desired inlet temperature to the coupling reactor 512. The coupling reactor products may include HBr, higher hydrocarbons, unreacted hydrocarbons, alkyl bromides, or any combination thereof. The coupling reactor products may exit the coupling reactor 512 and be carried by a line 514 to an HBr separation unit 516. The coupling reactor products may pass through another heat exchanger as necessary to adjust the temperature of the coupling products stream to a desired inlet temperature to the HBr separation unit 516.

HBr may be separated from the hydrocarbons using any suitable separation techniques. In an embodiment, the HBr may be separated from the HBr coupling reactor products using aqueous absorption. In this embodiment, the HBr coupling reactor products may be contacted with an aqueous solution to absorb any HBr in the vapor stream. The resulting substantially HBr-free products stream may pass by line 518 to a products recovery unit, numerous embodiments of which are disclosed herein. In general, any light hydrocarbons contained in the product stream may be separated and directed through line 522. Any recovered methane may be returned to the bromination reactor and other light hydrocarbons may be returned to a lights bromination reactor if present. Alternately, the light gases may be added to the downstream zone of the bromination reactor where they may reproportionate with polybromides to form the corresponding alkyl bromides. In still another embodiment, the light hydrocarbons may be directed to a fuel line for use in generating any desired energy for the process. A final products stream may be directed through line 524 to pass out of the process.

The aqueous HBr stream leaving the absorber may be carried by a line 526 to an HBr capture reactor. Air or oxygen may be fed into the unit through line 532 and a solid CuBr stream may be fed into the unit through line 506 from the bromine generation reactor 503. HBr may be captured through the reaction of HBr and oxygen with the CuBr to yield $CuBr_2$ and water. Any inert gases contained in the feed streams, such as $N_2$ if air is used as the oxygen source, may exit the reactor through vent line 530. The vent line may pass through a scrubbing unit to remove any trace HBr prior to being released from the process. In another embodiment, an aqueous solution of $CuBr/CuBr_2$ may be utilized as the absorbent in the absorption step. Alternatively, a slurry consisting of CuBr and $CuBr_2$ crystals in solution saturated with respect to CuBr and $CuBr_2$ may be used as the absorbent.

The resulting slurry generated in the HBr Capture Reactor 530 may contain $CuBr_2$, any unreacted CuBr, water, and potentially trace amounts of HBr. The slurry may be subjected to evaporative crystallization or other suitable technique to remove excess water formed in the reaction and to form additional CuBr2 crystals. Separation of CuBr2 crystals from the slurry may be accomplished by filtration, centrifugation, or any other suitable solids/liquids separation technique. The evaporated water may pass through line 538 to be used as a contact absorbent in the absorber 516, to pass out of the system, or any combination thereof.

The slurry containing the solid phase crystals may pass through line 546 to a dewatering unit to further remove any excess water from the solid phase CuBr and $CuBr_2$ crystals. The dewater unit may be any type of process capable of removing additional water from the CuBr and $CuBr_2$ crystals. For example, the dewatering unit may be a filtration unit, a centrifugal separator, or a heating unit capable of thermally driving off the water. The aqueous stream leaving the dewatering unit 544 may be saturated with respect to both CuBr and $CuBr_2$ and may contain small amounts of solid crystals suspended in the fluid. The aqueous stream 542 may pass back to the crystallizer 536 through line 542. Alternatively the aqueous stream 542 may go to the absorber/stripper 516 and serve as the HBr absorbent.

The $CuBr_2$ and CuBr crystals, which may still contain water, may be dried in a drying unit 550 at a temperature low enough to avoid bromine release. In an embodiment, the drying temperature may be below about 200° C. Any remaining water in the CuBr and $CuBr_2$ crystals may be driven off and leave the system through line 552. The water vapor may pass through a scavenging unit to capture any bromine generated during drying. The dried $CuBr_2$ crystals may then be sent to a bromine generation unit through line 502.

Figure 27:
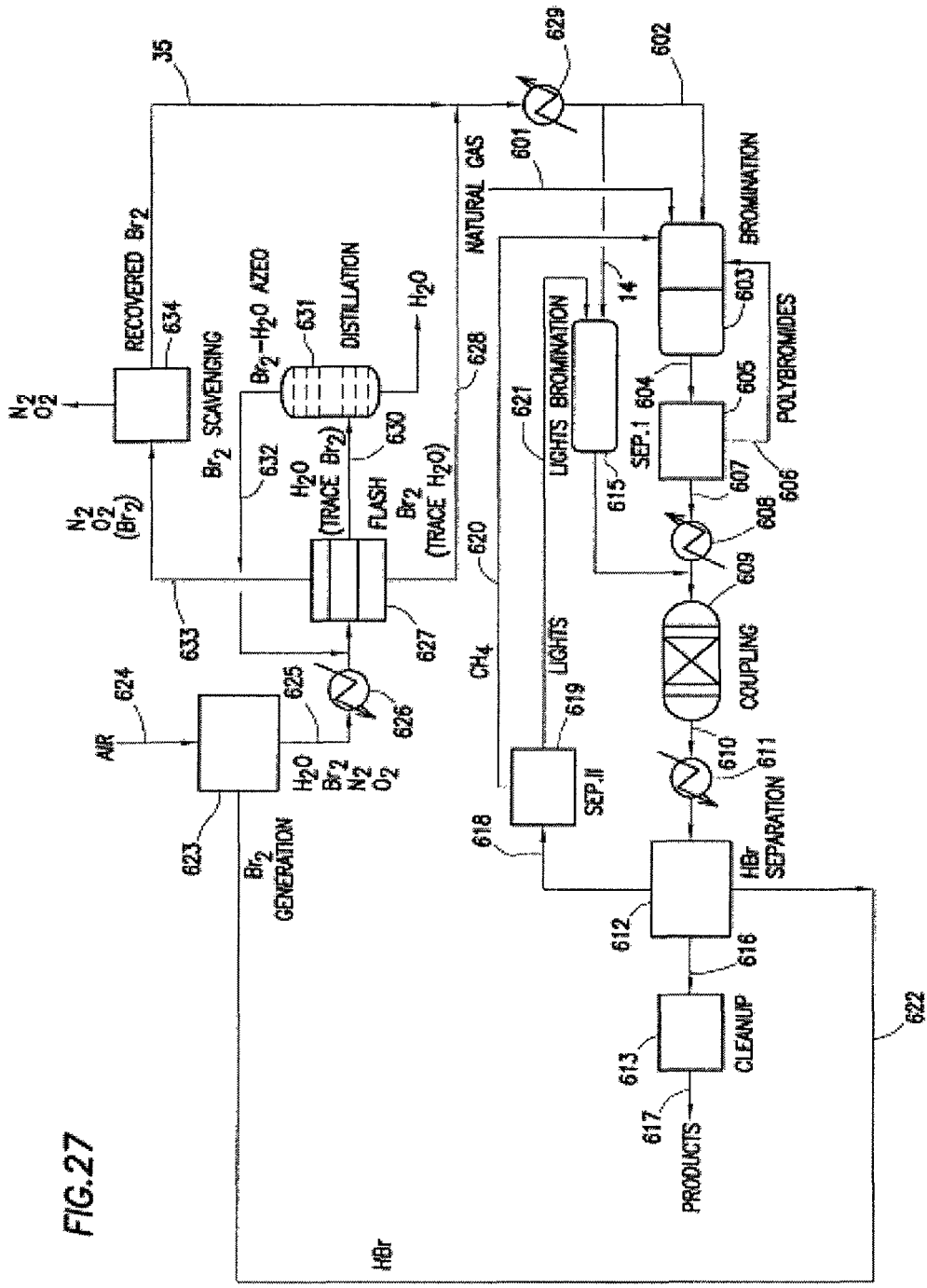
FIG. 27 is a schematic view of one embodiment of a continuous process for converting methane or natural gas into hydrocarbon chemicals according to the invention.

As shown in FIG. 27, an aqueous HBr to $Br_2$ conversion process may be applied to a process for the conversion of alkanes to higher liquid hydrocarbons. In an embodiment, natural gas (or another hydrocarbon feedstock) and molecular bromine may be carried by separate lines 601, 602 into a heated bromination reactor 603 and allowed to react. Bromination products may include, but are not limited to, HBr, alkyl bromides, olefins, and possibly unreacted hydrocarbons. The bromination products may exit the reactor and be carried by a line 604 into a first separation unit 605, where monobrominated hydrocarbons and HBr may be separated from polybrominated hydrocarbons. In some embodiments, the polybromides may be carried by a line 606 back to the bromination reactor, where they may undergo reproportionation with methane and/or other light hydrocarbons, which may be present in the natural gas and/or introduced to the bromination reactor. Light gases such as ethane, propane and butane may be carried by line 621 and may be allowed react with bromine in a light hydrocarbon bromination reactor 615 to produce alkyl halides and HBr.

In the embodiment shown in FIG. 27, any unreacted hydrocarbon feedstock, HBr, monobromides, and any olefins formed in the bromination reactor may be carried by a line 607 to coupling reactor 609, where the monobromides, olefins, or any combination thereof may react in the presence of a coupling catalyst to form higher hydrocarbons. In an embodiment, a heat exchanger 608 may be used to adjust the temperature of the brominated products stream 607 to a desired inlet temperature to the coupling reactor 609. The coupling reactor products may include HBr, higher hydrocarbons, unreacted hydrocarbons, alkyl bromides, or any combination thereof. The coupling reactor products may exit the coupling reactor 609 and be carried by a line 610 to an HBr separation unit 612. The coupling reactor products may pass through another heat exchanger 611 as necessary to adjust the temperature of the coupling products stream to a desired inlet temperature to the HBr separation unit 612. HBr can be separated from the hydrocarbons using a number of different methods as previously described herein. For example, HBr may be separate using pressure-swing absorption, temperature-swing absorption, temperature-swing adsorption, membrane-based separation, distillation, or any combination of separation techniques, or another suitable separation technology. Specific descriptions of these technologies are included herein.

The liquid hydrocarbon products may then be carried by a line 16 to a product clean-up unit 613, to yield final hydrocarbon products 617. After HBr is separated from the hydrocarbon products and any light hydrocarbons that may be present in the HBr separation unit 612, the light hydrocarbons may be carried by a line 618 into a second separation unit 619, which may employ pressure- or temperature-swing adsorption, membrane-based separation, cryogenic distillation or any other suitable separation technology. Methane may be returned to the bromination reactor 604 via one or more line 620 and other light hydrocarbons may be returned to the lights bromination reactor 615 via line 621. Alternately, the light gases may be added to the downstream zone of the bromination reactor where they may reproportionate with polybromides to form the corresponding alkyl bromides.

The HBr stream that evolves from the HBr separation unit 612 may be carried by a line 622 to a bromine generation unit 623. Air or oxygen may be fed into the unit through line 624. Bromine may regenerated by reacting HBr with oxygen in the presence of a suitable catalyst such as an aqueous solution of selenium bromide or oxybromides ($SeOBr_2$, $Se_2Br_2$, etc.), as described above.

The resulting stream 625 from bromine generation reactor 623 may contain water, molecular bromine, oxygen, nitrogen, and possibly other gases if air was used as the source of oxygen. This product stream 625 may be carried through a heat exchanger system 626 into a flash vaporization unit 627, which may separate most of the molecular bromine from water, oxygen, nitrogen, and other gases that are present. Molecular bromine containing no more than a trace of $H_2O$, either as a liquid or vapor, may be carried by a line 628 to a heat exchanger 629, and then returned to the bromination reactor 603, the lights bromination reactor 615, or both.

Water from the flash vaporization unit (containing up to about 3% by weight of molecular bromine) may be sent by a line 630 to a distillation unit 631, which may yields water as the bottoms stream and bromine or bromine-water azeotrope as a distillate. The distillate may be returned through a line 632 back to the flash vaporization unit. An embodiment of this invention may utilize pH control in the distillation column 631 to prevent the hydrolysis reaction between water and bromine. The hydrolysis reaction may produce HBr, which may be lost in the bottoms stream of the distillation column in the absence of pH control. A pH of lower than about 3 may be desired to reduce or eliminate the hydrolysis reaction. Conventional acids such as sulfuric acid, hydrochloric acid, or phosphoric acid may be used for pH control.

The gaseous products of the flash vaporization unit may contain no more than a minor or trace amount of bromine and may carried by a line 633 to a bromine scavenging unit 634, which may separate molecular bromine from the other gases. As described above, adsorbents or reactants capable of capturing bromine may be used for bromine scavenging.

Figure 28:
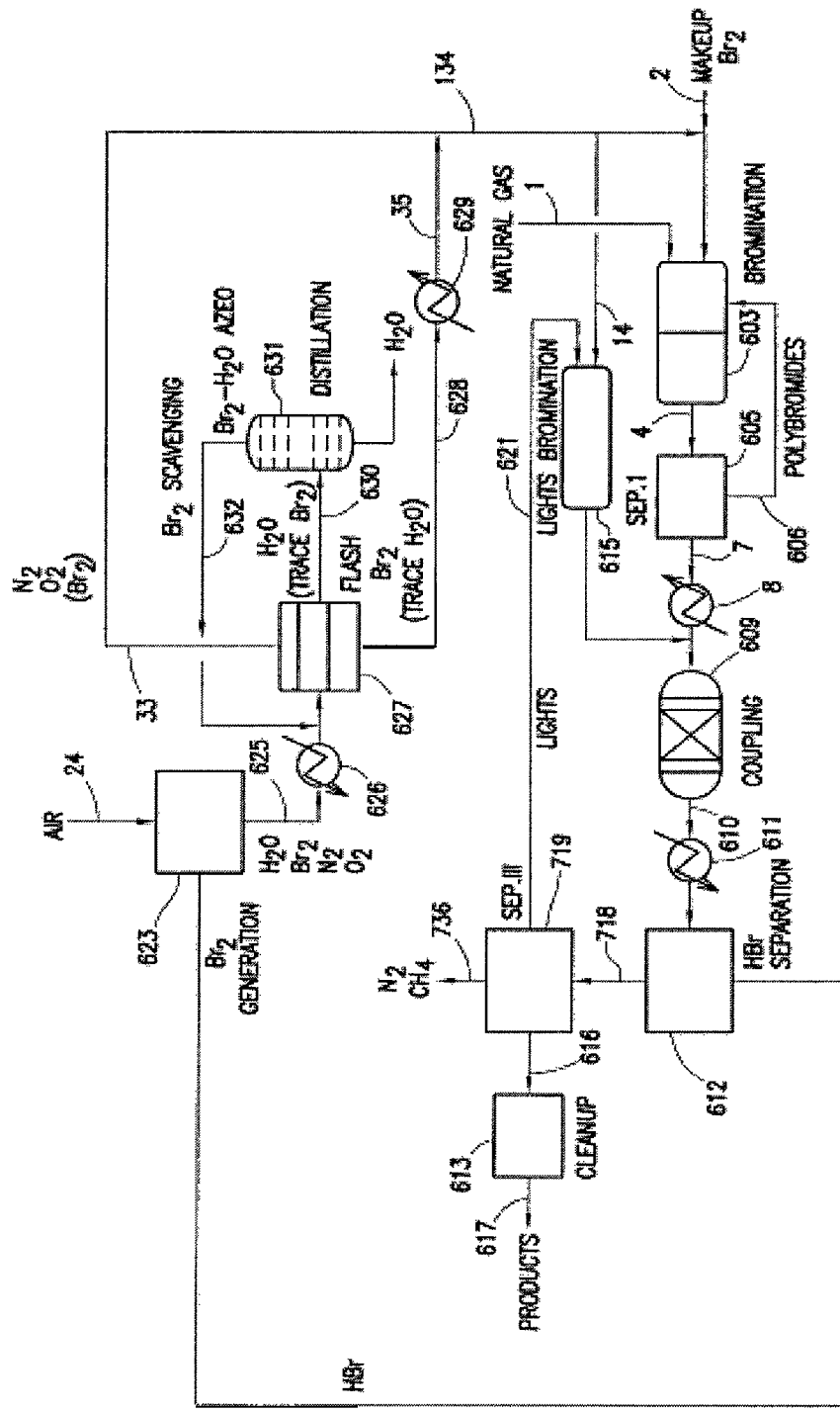
FIG. 28 is a schematic view of one embodiment of a continuous process for converting methane or natural gas into hydrocarbon chemicals according to the invention.

Another embodiment of the process for converting gaseous alkanes into liquid hydrocarbons utilizing the conversion of HBr into elemental bromine in the presence of selenium or tellurium is shown in FIG. 28. In this process configuration, the operating pressure of the $Br_2$ generation unit 623 may be greater than the pressure in the bromination reactor 603. As in the previous case, stream 625 from bromine generation reactor 623 may contain water, molecular bromine, oxygen, nitrogen, and possibly other gases if air was used as the source of oxygen. This product stream 625 may be carried through a heat exchanger system 626 into a flash vaporization unit 627, which may separate most of the molecular bromine from water, oxygen, nitrogen, and any other gases that may be present. Liquid molecular bromine, containing no more than a trace of $H_2O$, may be carried by a line 628 to a heat exchanger 629, and then returned to the bromination reactor. Water from the flash vaporization unit, which may contain up to about 3% by weight of molecular bromine, may be sent by a line 630 to a distillation unit 631, which may yield water as the bottoms stream and bromine or bromine-water azeotrope as a distillate. The distillate may be returned through a line 632 back to the flash vaporization unit.

The gaseous products of the flash vaporization unit may be returned to the bromination reactor 603, the lights bromination reactor 615, or both. In this embodiment, the bromination reactor 603, the polybromide separation unit 605, the lights bromination reactor 615, and the coupling reactor 609 may be the same as in the previous embodiment, except that all product and feed streams, with the exception of stream 606, may also contain $N_2$.

The coupling product stream 610, which may contain hydrocarbons, HBr, and $N_2$, may be cooled in heat exchanger 611, and then go to the HBr separation unit 612. The HBr separation unit 612 may selectively separate HBr from the other components and transport the HBr via line 622 to the bromine generation unit 623. A number of different methods may be used to achieve the desired separation (e.g., distillation, adsorption, etc.). In some embodiments, temperature swing absorption may be used to separate the HBr from the coupling products stream, as described above.

Stream 718, which may contain only hydrocarbons and $N_2$, may be transported to a product recovery unit 719. The product recovery unit 719 may produce a liquid hydrocarbon product stream 616, which may be sent to a product cleanup unit 613 to yield the final hydrocarbon products 617; a light gases stream 621 containing primarily $C_3$ and $C_4$ hydrocarbons, which may be further refined to product LPG product or sent to lights bromination unit 615; and a gas stream 736, which may contain $N_2$, unconverted $CH_4$, and possibly some $C_2$ and $C_3$ hydrocarbons. The gas stream 736 may be used as fuel for generating any energy (e.g., heat, electricity, etc.) that may be required for the process.

A number of different methods may be used to achieve the desired separation in the product recovery unit 719. In some embodiments, a heavy organic solvent (either a pure component (e.g., $C_{12}H_{26}$) or a mixture (e.g., diesel)) may be used to absorb all the $C_5$ and heavier hydrocarbons, along with significant amounts of $C_4$ and $C_3$ hydrocarbons present in stream 718. A distillation sequence may then be used to recover the liquid hydrocarbon product and light gases (e.g., $C_4$ and $C_3$ hydrocarbons) from the solvent, which may then be recycled to the absorber. Any $C_4$ and lighter hydrocarbons may be recovered from the gas stream leaving the absorber using techniques such as cryogenic distillation, expansion cooling, absorption, membrane, pressure/temperature swing adsorption, etc.

This embodiment may allow the bromine scavenging unit to be eliminated and allow cooling water, rather than brine or refrigeration, to be used in the flash separation unit 627. However, due to the presence of $N_2$, the bromination reactor 603, the polybromide separation unit 605, the lights bromination reactor 615, and the coupling reactor 609 may be larger. This embodiment may be economically attractive for small scale processes such as those producing less than about 3,000 barrels of liquid hydrocarbons per day. In another embodiment, this embodiment may be attractive for processes producing less than about 2,000 barrels per day.

Figure 29:
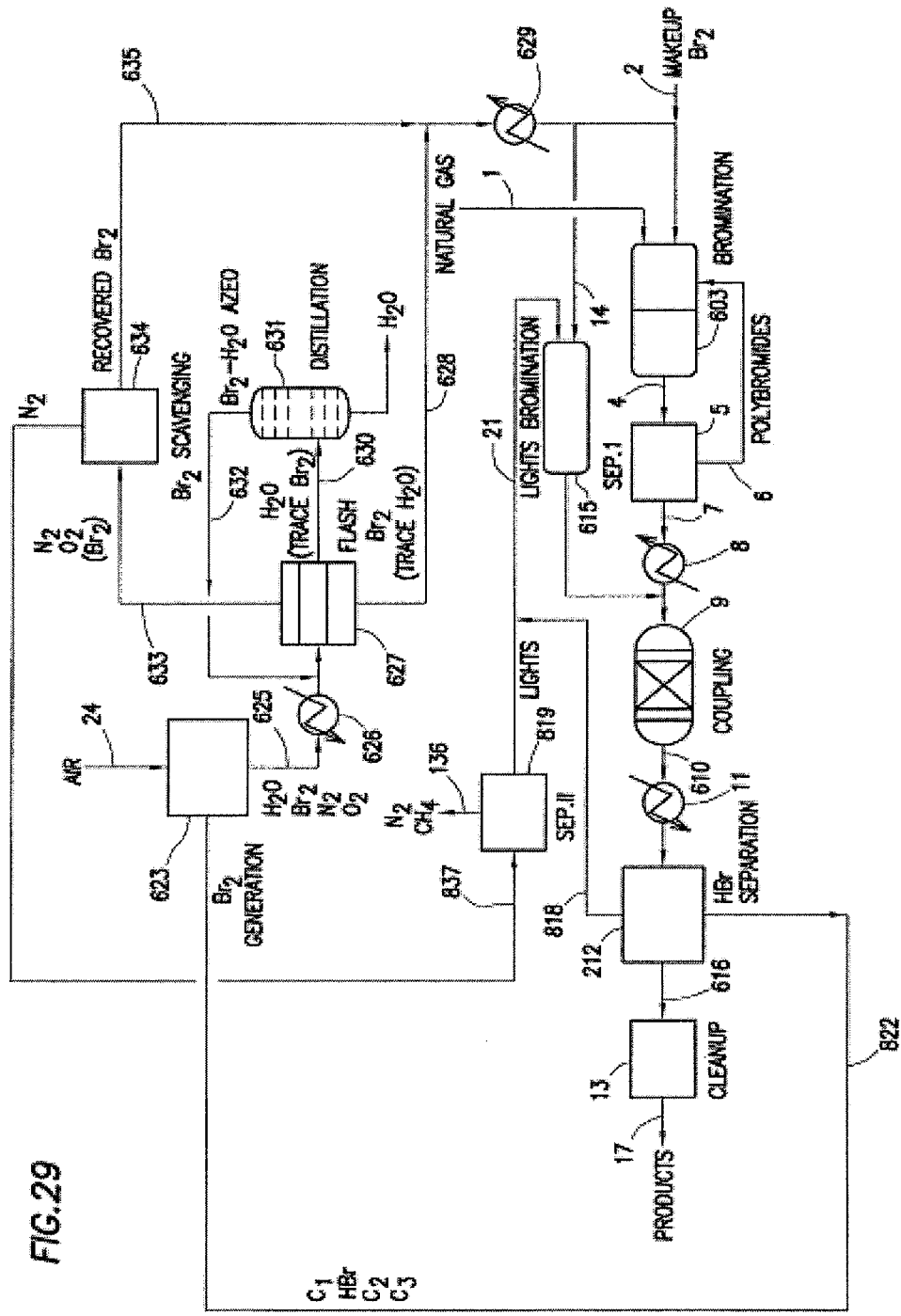
FIG. 29 is a schematic view of one embodiment of a continuous process for converting methane or natural gas into hydrocarbon chemicals according to the invention.

Another embodiment of the process is shown in FIG. 29. Due to the difficulty in obtaining a high purity HBr stream with a high recovery as a result of the VLE behavior of ethane-HBr and HBr-propene, a different separation process may be used to remove HBr from the coupling products stream 610. In this embodiment, the cooled coupling product stream 610, which may contain hydrocarbons and HBr, may be separated to yield a vapor stream 822 containing HBr, $C_3$, and lighter hydrocarbons; a liquid hydrocarbon stream 616; and a $C_4$ hydrocarbon stream 818, which may also contain some $C_3$ as well. A number of different methods may be used to achieve the separation including, but not limited to, distillation, a solvent absorption based process, or both. Stream 822 may be transported to the bromine generation unit 623 where HBr may be converted to $Br_2$ in the presence of selenium or tellurium, as described above. The light hydrocarbons may pass through the process unreacted. Stream 625 from bromine generation reactor 623 may contain water, molecular bromine, oxygen, nitrogen if air was used as the source of oxygen, and any $C_3$ and lighter hydrocarbons that entered the bromine generation reactor. The product stream 625 may be carried through a heat exchanger system 626 into a flash vaporization unit 627, which may separate most of the molecular bromine from the water, oxygen, nitrogen, and any light hydrocarbons that may be present. Liquid molecular bromine containing no more than a trace of $H_2O$ may be carried by a line 628 to a heat exchanger 629, and then returned to the bromination reactor 603, the lights bromination reactor 615, or both. Water from the flash vaporization unit containing up to about 3% by weight of molecular bromine may be sent by a line 630 to a distillation unit 631, which may yield water as the bottoms stream and bromine or bromine-water azeotrope as a distillate. The distillate may be returned through a line 632 back to the flash vaporization unit.

The gaseous products of the flash vaporization unit (e.g., oxygen, nitrogen, light hydrocarbons, and no more than a minor or trace amount of bromine) may be carried by a line 633 to a bromine scavenging unit 634, which may separate molecular bromine from any other gases present. Any of the techniques described above may be used for bromine scavenging. The recovered bromine may be carried by a line 365 through a heat exchanger 629 and reintroduced into the bromination reactor 603, the lights bromination reactor 615, or both. The remaining gases, which may include oxygen, nitrogen, and light hydrocarbons, may be transported via line 837 to a separation unit 819, where any hydrocarbons including, but not limited to, $C_2$, $C_3$, and heavier hydrocarbons, may be recovered and sent, along with stream 818, to lights bromination reactor 615. The remaining gases including, but not limited to, oxygen, nitrogen, methane and some light hydrocarbons, may be used as fuel for generating energy for the process. Any standard separation technology including, but not limited to, distillation, expansion cooling, absorption, membrane, and pressure/temperature swing adsorption, may be used to achieve the desired separation.

Continuous Flow Zone Reactor Configurations (CFZR)

Figure 30:
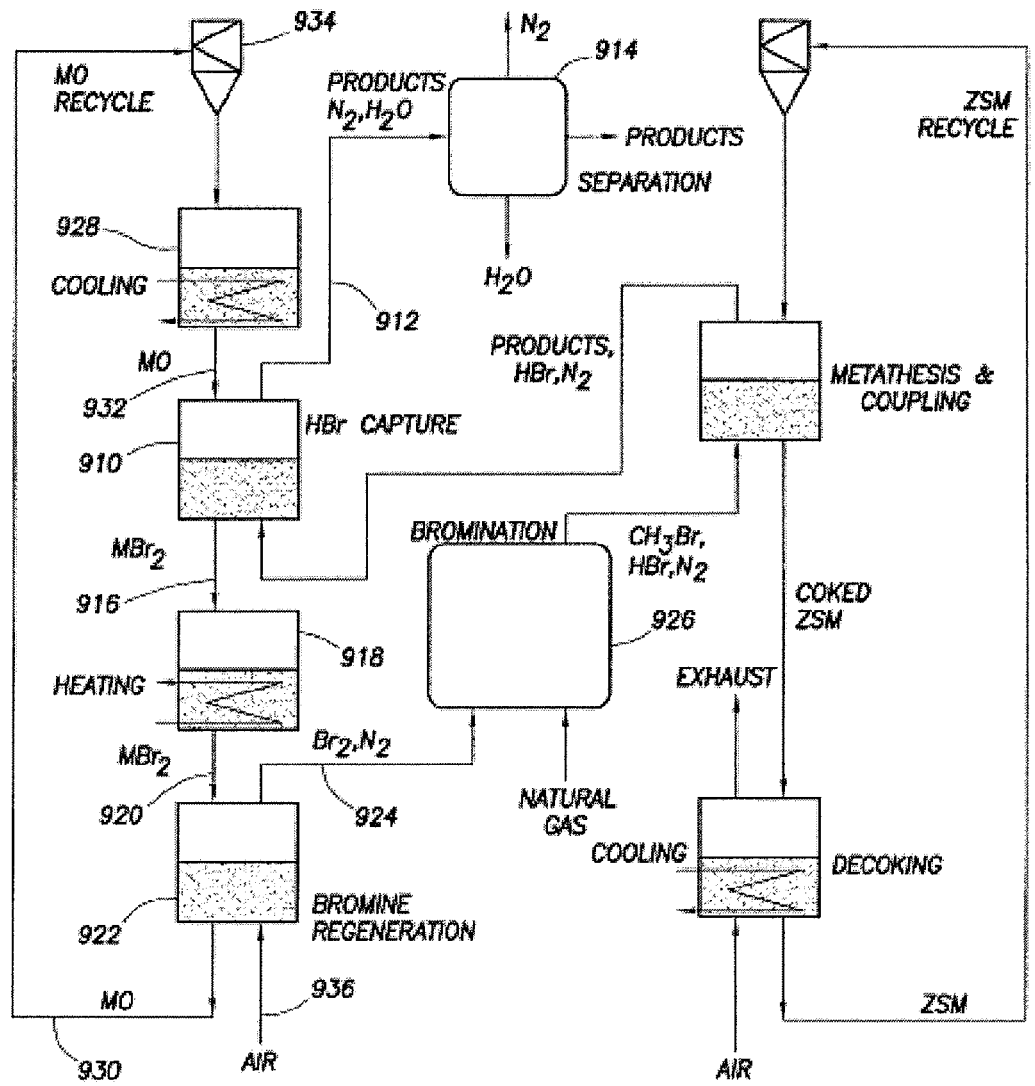
FIG. 30 is a schematic view of one embodiment of a continuous process for converting methane or natural gas into hydrocarbon chemicals according to the invention using a continuous flow zone reactor configuration.

In an embodiment that utilizes a solid reactant to capture hydrogen halide, a continuous flow zone reactor (hereinafter CFZR) may be used to carry out the method of converting hydrocarbon feedstocks into useful products. The CFZR comprises of two or more zones in which the solid catalyst particulates (e.g., comprising cataloreactants) may be transported between the zones by gravity, pneumatic conveyance, or any other direct transport means as are known in the art for fluidized or moving bed reactor designs, or any combination thereof. An embodiment of the CFZR is shown in FIG. 30 with a plurality of reactor zones. The solid reactant particles may react with hydrogen halide (e.g., HBr) in the hydrogen halide neutralization zone 910 to make water and metal bromide, which may pass along with the products and any inert gases in the outlet stream 912 to a products separation sub-process 914, as described in more detail above. The catalytic solids may leave the neutralization zone as a metal bromide stream 916. In order to prevent hydrogen halide breakthrough in the neutralization zone, the solids flowrate may contain a metal oxide in an amount exceeding the stoichiometric requirement to neutralize the entering hydrogen halide. As a result, the metal bromide stream 916 leaving the hydrogen halide neutralization zone 910 may comprise metal bromide and metal oxide.

As shown in FIG. 30, the metal bromide stream 916 may be heated in a heating zone 918 using any known method for heating a solid particulate. Non-limiting examples may include heat transfer through direct contact with inert gases or by indirect contact through heat transfer tubes in a fluidized bed. The resulting heated metal bromide stream 920 may leave the heating zone 918 and pass into a bromine generation reactor 922. The metal bromide, which may contain some metal oxide, may be contacted with an air or oxygen stream 936 to generate elemental bromine in the bromine generation reactor 922. Any residual hydrocarbons or brominated hydrocarbons adsorbed on the solid catalyst may also be oxidized by contact with air. The combustion products may include $CO_2$, $N_2$, and potentially some trace hydrogen halide. These products may pass out of the bromine generation reactor 922 as a bromine stream 924, which may pass to a bromination reactor 926 for use in the formation of alkyl bromides, as described in more detail above. Upon contact with the air or oxygen source, the metal bromide may be converted to a metal oxide for reuse in the process. Depending on the reaction conditions, the metal oxide stream 930 may comprise some solid catalyst as a metal bromide in order to avoid oxygen breakthrough into the bromine stream 924.

The metal oxide stream 930 leaving the bromine generation reactor may be conveyed to a cooling zone 928, where the catalyst may be cooled using any known method for cooling a solid particulate. Non-limiting examples may include heat transfer through direct contact with inert gases or by indirect contact through heat transfer tubes in a fluidized bed. The cooled metal oxide stream 932 may then pass out of the cooling zone 928 and into the hydrogen halide neutralization zone 910 to complete the solid catalyst recycle loop. An optional metal oxide storage vessel 934 may be utilized before or after the cooling zone to store the metal oxide solid reactant prior to metering a desired amount back into the process. In an embodiment utilizing a storage vessel, the storage vessel may be capable of storing the entire amount of metal oxide in the event of a process shutdown.

In the embodiment shown in FIG. 30, both bromine generation reactor 922 and the hydrogen halide neutralization zone 910 may be adiabatic reactors. The HBr neutralization zone 910 may be a dense moving bed or a fluidized bed reactor, or a combination of both. The Bromine regeneration reactor may be either a dense moving bed reactor, a fluidized bed reactor, or a combination of both. The moving bed reactors may be configured with gas flowing upward against the flow of solids, or downward, parallel to the flow of solids. Solid flow from each reactor may be regulated by a looping seal valve, a rotary valve, or by other mechanical means. Although FIG. 30 shows a particular vertical alignment of the zone reactor, other configurations are feasible.

In another embodiment of the CFZR, an additional gas stream (not shown in FIG. 30) may also be added to the neutralization zone 910. This stream may be substantially hydrogen halide free, and may be primarily composed of light gases such as $N_2$, methane and other light hydrocarbons (e.g., $C_2$, $C_3$, and C4). In addition is may also include water and small amounts of higher hydrocarbons ($C_5$+). The purpose of this stream is to reduce the temperature rise in the neutralization zone, and this stream may be either added directly to the neutralization zone, or mixed with the feed stream to the neutralization zone. This stream may be external to the system, or it may be an appropriate stream from another part of the system (e.g., an appropriate gas stream in the separation sub-process). This embodiment may improve the economics of the entire process by reducing or eliminating the cooling load in cooling section of the CFZR and transferring it to the product recovery system. This may result in a process with a lower capital cost as the materials of construction used for the heat transfer surfaces in the CFZR may be significantly more expensive than those used in the product recovery system due to the presence of a hydrohalic acid. In addition, this embodiment also decreases the change in the temperature of the catalytic solids as it passes through the different zones of the CFZR, which may in turn increase the overall life of the catalytic solid.

Other embodiments may also be possible. For example, the solid catalytic reactant may remain stationary, while moving the zone from one location to the next, in a continuous loop, in the configuration of a simulated moving bed. In this embodiment, a series of control valves may be used to sequentially direct flow from one zone to the next. This has the advantage of near continuous operation without the additional complexity of moving the solids between zones. In a similar manner, the zone reactor may be configured as rotating wheel, in which case the solids may be moved in a dense plug from one location to another in tangential movement. The gases in each zone are fed continuously, while solids are pushed from one zone to the next in a circular pathway around the wheel.

To facilitate a better understanding of the present invention, the following examples of certain aspects of some embodiments are given. In no way should the following examples be read to limit, or define, the scope of the invention.

EXAMPLE 1

Reproportionation of Dibromomethane with Propane

Methane (11 sccm, 1 atm) was combined with nitrogen (15 sccm, 1 atm) at room temperature via a mixing tee and passed through a room temperature bubbler full of bromine. The $CH_4/N_2/Br_2$ mixture was plumbed into a preheated glass tube at 500° C., and bromination of the methane took place with a residence time ("$t_{res}$") of 60 seconds, producing primarily bromomethane, dibromomethane, and HBr. The stream of nitrogen, HBr, and partially brominated hydrocarbon was combined with propane (0.75 sccm, 1 atm) in a mixing tee and passed into a second glass reactor tube at 525° C. with a residence time ("$t_{res}$") of 60 s. In the second reactor tube, polybrominated hydrocarbons (e.g., $CH_2Br_2$, $CHBr_3$) react with the propane to produce bromopropanes. The reproportionation is idealized by the following reaction:

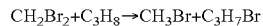

$CH_2Br_2 + C_3H_8 \rightarrow CH_3Br + C_3H_7Br$

As products left the second reactor, they were collected by a series of traps containing 4 M NaOH (which neutralized the HBr) and hexadecane (containing octadecane as an internal standard) to dissolve as much of the hydrocarbon products as possible. Volatile components like methane and propane were collected in a gas bag after the HBr/hydrocarbon traps. All products were quantified by gas chromatography. The results ("Ex. 1") are summarized in Table 1. For comparison, the reactions were also run with two reactors, but without reproportionation with propane ("Control A"), and with only the first reactor and without propane ("Control B").

TABLE 1

Reproportionation of Dibromomethane

| | Ex. 1 (bromination/ reproportionation) | Control A (bromination) | Control B (bromination) |
|---|---|---|---|
| Bromination $t_{res}$ | 60 | 60 | 60 |
| Reproportionation $t_{res}$ | 60 | 60 | 0 |
| $CH_4$ conversion | 40% | 47% | 45% |
| $CH_3Br/(CH_3Br + CH_2Br_2)$ | 93% | 84% | 74% |
| $C_3H_8$ conversion | 85% | N/A | N/A |
| Carbon balance | 96% | 97% | 96% |

EXAMPLE 2

Separation of Anhydrous HBr 20 ml stock HBr aqueous solution were added to 20 g $CaBr_2H_2O$ followed by heating to 70° C. A significant evolution of HBr gas was observed (determined by $AgNO_3$ precipitation and the $NH_3$ fuming test). The released HBr was not quantified as the reaction was carried out in an open vessel.

EXAMPLE 3

Separation of Anhydrous HBr

Dehydration with $H_2SO_4$ was attempted by adding a concentrated solution of $H_2SO_4$ to HBr. Qualitative tests were conducted in which different concentration of $H_2SO_4$ were added to HBr for determination of the threshold concentration where oxidation of HBr no longer occurs: $2HBr + H_2SO_4 \rightarrow Br_2 + SO_2 + 2H_2O$ It was determined that the $H_2SO_4$ concentration below which no oxidation is apparent is about 70 wt. %. 30 ml 70% $H_2SO_4$ was added to 30 ml stock HBr azeotrope (48 wt. %) and the mixture was heated to boiling. The HBr content was determined quantitatively by $AgNO_3$ precipitation and gravimetric determination of AgBr from a solution aliquot at the moment of mixing, after 15 min and after 30 min boiling.

EXAMPLE 4

Metathesis of Brominated Methane Over Selected Catalysts

A series of experiments were conducted in which methane was brominated in a manner substantially the same as or similar to that described in Example 1 (10 sccm methane bubbled through room temperature bromine, followed by passage of the mixture through a reactor tube heated to 500° C.), and the bromination products were then passed over various metal-ion exchanged or impregnated zeolite catalysts, at atmospheric pressure (total pressure), at a temperature of from 350° C. to 450° C., with a residence time of 40 seconds. Table 2 summarizes the distribution of metathesis products. Catalysts are denoted by metal ion (e.g., Ba, Co, Mn, etc.) and by type of Zeolyst Int'l. zeolite (e.g., 5524, 58, 8014, etc.). The mass (mg) of each product, as well as the total mass of products is given for each run. The abbreviations, B, PhBr, T, X, and M refer to benzene, phenyl bromide, toluene, xylene, and mesitylene, respectively.

TABLE 2

Metathesis of Brominated Methane Over Selected Catalysts

| T (C.) | Catalyst | B | PhBr | T | X | M | Total (mg) |
|---|---|---|---|---|---|---|---|
| 350 | Ba 5524 | 0.25 | 0 | 0.96 | 2.58 | 3.14 | 6.93 |
| 350 | Ba 58 | 0.31 | 0 | 1.48 | 3.2 | 3.11 | 8.11 |
| 350 | Ba 8014 | 0.3 | 0 | 1.3 | 2.87 | 3.15 | 7.6 |
| 350 | Ca 58 | 0.2 | 0 | 0.81 | 2.44 | 3.09 | 6.53 |
| 350 | Co 2314 | 1.22 | 0.02 | 3.05 | 2.18 | 0.56 | 7.04 |
| 350 | Co 3024 | 0.36 | 0 | 2.06 | 4.21 | 3.47 | 10.1 |
| 350 | Co 58 | 0.2 | 0 | 1.05 | 2.91 | 3.34 | 7.5 |
| 350 | Mg 3024 | 0.31 | 0 | 1.53 | 3.59 | 3.89 | 9.32 |
| 350 | Mg 58 | 0.28 | 0 | 1.41 | 3.3 | 3.43 | 8.42 |
| 350 | Mn 2314 | 1.07 | 0.03 | 2.86 | 2.26 | 0.65 | 6.86 |
| 350 | Mn 3024 | 0.53 | 0 | 2.92 | 4.8 | 3.02 | 11.27 |
| 350 | Mn 58 | 0.17 | 0 | 0.88 | 2.7 | 3.62 | 7.37 |
| 350 | Ni 2314 | 1.12 | 0.05 | 2.94 | 2.44 | 0.74 | 7.29 |
| 350 | Ni 3024 | 0.61 | 0 | 2.82 | 3.85 | 2.13 | 9.41 |
| 375 | Ba 5524 | 0.32 | 0 | 1.32 | 2.82 | 2.57 | 7.04 |
| 375 | Ba 58 | 0.4 | 0 | 1.84 | 2.93 | 2.4 | 7.57 |
| 375 | Ba 8014 | 0.32 | 0 | 1.23 | 2.84 | 2.95 | 7.34 |
| 375 | Ca 58 | 0.2 | 0 | 0.96 | 2.55 | 2.93 | 6.64 |
| 375 | Co 3024 | 0.47 | 0 | 2.3 | 3.52 | 2.18 | 8.48 |
| 375 | Co 58 | 0.3 | 0 | 1.54 | 2.83 | 2.42 | 7.1 |
| 375 | Mg 3024 | 0.37 | 0 | 1.81 | 3.26 | 2.78 | 8.22 |
| 375 | Mg 58 | 0.34 | 0 | 1.67 | 3.04 | 2.74 | 7.8 |
| 375 | Mn 3024 | 0.62 | 0 | 2.91 | 3.9 | 2.17 | 9.59 |
| 375 | Mn 58 | 0.22 | 0 | 1.18 | 2.71 | 2.83 | 6.94 |
| 375 | Pd 2314 | 1.54 | 0 | 3.1 | 1.83 | 0.37 | 6.85 |
| 400 | Ba 5524 | 0.46 | 0 | 2.37 | 4.16 | 2.95 | 9.94 |
| 400 | Ba 58 | 0.7 | 0 | 3.15 | 3.91 | 2.7 | 10.47 |
| 400 | Ba 8014 | 0.38 | 0 | 1.57 | 3.81 | 3.77 | 9.53 |
| 400 | Ca 58 | 0.41 | 0 | 1.89 | 3.43 | 2.81 | 8.54 |
| 400 | Co 3024 | 0.78 | 0 | 3.42 | 4.14 | 2.26 | 10.6 |
| 400 | Co 58 | 0.62 | 0 | 2.71 | 3.36 | 2.31 | 8.99 |
| 400 | Mg 3024 | 0.76 | 0 | 3.26 | 4.11 | 2.64 | 10.76 |
| 400 | Mg 58 | 0.71 | 0 | 3.04 | 3.74 | 2.59 | 10.08 |
| 400 | Mn 3024 | 0.98 | 0 | 4.1 | 4.38 | 2.06 | 11.52 |
| 400 | Mn 58 | 0.48 | 0 | 2.26 | 3.44 | 2.64 | 8.82 |
| 400 | Ni 3024 | 0.81 | 0 | 3.15 | 3.35 | 1.72 | 9.04 |
| 400 | Pb 2314 | 1.2 | 0.03 | 3.25 | 3.27 | 1.2 | 8.94 |
| 400 | Pb 3024 | 1.07 | 0.04 | 2.77 | 3.63 | 1.66 | 9.17 |
| 400 | Pd 2314 | 2.44 | 0 | 3.16 | 1.22 | 0.18 | 7.01 |
| 400 | Sr 2314 | 2.13 | 0.01 | 4.05 | 2.29 | 0.46 | 8.94 |
| 400 | Sr 3024 | 1.93 | 0.05 | 4.03 | 2.67 | 0.65 | 9.32 |
| 425 | Ag 3024 | 2.79 | 0.02 | 4.16 | 1.78 | 0.29 | 9.04 |
| 425 | Ag 8014 | 3.09 | 0.02 | 3.52 | 1.09 | 0.16 | 7.88 |
| 425 | Ba 5524 | 0.54 | 0 | 2.67 | 3.67 | 2.33 | 9.22 |
| 425 | Ba 58 | 0.79 | 0 | 3 | 2.94 | 1.75 | 8.48 |
| 425 | Bi 2314 | 3.13 | 0.03 | 4.47 | 1.61 | 0.23 | 9.48 |
| 425 | Co 2314 | 3.39 | 0.03 | 4.34 | 1.59 | 0.25 | 9.6 |
| 425 | Co 3024 | 1.07 | 0 | 3.42 | 2.79 | 1.09 | 8.38 |
| 425 | Cu 2314 | 2.89 | 0.02 | 4.74 | 2.13 | 0.37 | 10.15 |
| 425 | Li 5524 | 1.51 | 0.04 | 3.31 | 3.27 | 1.12 | 9.24 |
| 425 | Mg 3024 | 0.99 | 0 | 3.28 | 2.85 | 1.37 | 8.48 |
| 425 | Mg 58 | 0.81 | 0 | 2.62 | 2.16 | 1.11 | 6.7 |
| 425 | Mn 3024 | 1.22 | 0 | 3.9 | 3.01 | 1.14 | 9.27 |
| 425 | Mo 2314 | 3.06 | 0.04 | 4.02 | 1.46 | 0.24 | 8.82 |
| 425 | Ni 3024 | 0.97 | 0 | 3.38 | 2.85 | 1.32 | 8.51 |
| 425 | Sr 3024 | 2.53 | 0.02 | 4.36 | 2.22 | 0.43 | 9.56 |
| 450 | Ag 3024 | 3.84 | 0.02 | 4.27 | 1.36 | 0.18 | 9.67 |
| 450 | Bi 2314 | 3.9 | 0.01 | 3.59 | 0.67 | 0.06 | 8.23 |
| 450 | Ca 2314 | 3.64 | 0.02 | 4.1 | 1 | 0.16 | 8.92 |
| 450 | Co 2314 | 4.12 | 0.01 | 3.77 | 0.77 | 0.08 | 8.75 |
| 450 | Cu 2314 | 3.65 | 0 | 4.3 | 1.1 | 0.14 | 9.19 |
| 450 | Fe 2314 | 4.42 | 0.02 | 3.43 | 0.74 | 0.09 | 8.69 |
| 450 | Fe 3024 | 3.61 | 0.01 | 2.96 | 0.63 | 0.08 | 7.28 |
| 450 | Fe 5524 | 3.99 | 0.03 | 3.63 | 0.85 | 0.11 | 8.6 |
| 450 | La 2314 | 3.48 | 0.01 | 3.81 | 0.87 | 0.12 | 8.29 |
| 450 | Li 8014 | 1.74 | 0.02 | 2.61 | 2.67 | 0.84 | 7.89 |
| 450 | Mg 2314 | 4.2 | 0.02 | 3.84 | 0.76 | 0.1 | 8.92 |
| 450 | Mn 2314 | 3.78 | 0.02 | 3.9 | 0.88 | 0.12 | 8.7 |
| 450 | Mo 2314 | 3.88 | 0.01 | 3.26 | 0.58 | 0.06 | 7.79 |
| 450 | Ni 2314 | 4.39 | 0.01 | 3.12 | 0.44 | 0.03 | 8 |
| 450 | Pb 2314 | 2.58 | 0.01 | 4.68 | 2.31 | 0.45 | 10.02 |
| 450 | Pb 3024 | 2.08 | 0.01 | 4.44 | 2.87 | 0.7 | 10.1 |
| 450 | Pb 5524 | 1.89 | 0.02 | 3.58 | 2.71 | 0.73 | 8.93 |
| 450 | Pd 2314 | 4.03 | 0 | 1.58 | 0.14 | 0 | 5.76 |
| 450 | Sr 2314 | 3.71 | 0 | 4.78 | 1.68 | 0.21 | 10.39 |
| 450 | Sr 3024 | 2.51 | 0.01 | 3.76 | 1.61 | 0.26 | 8.14 |

EXAMPLE 5

Hydrodehalogenation of Bromobenzene, and Catalyst Regeneration

A test solution (1.5 ml/hr), which includes 1.9 wt % bromobenzene (PhBr) dissolved in dodecane, diluted by $N_2$ (1.1 ml/min) was fed into a tubular quartz reactor in which 3.6 g of highly dispersed precious metal catalyst ($Pd/Al_2O_3$, 0.5 wt %) was loaded. The reaction was carried out at 325° C. with a residence time of 15 s. The reaction effluent was trapped in a bubbler with 8 ml 4M NaOH solution pre-added. The carrier gas as well as the gaseous product were collected in a gas bag. All of the carbon-based products in the gas phase and oil phase in the liquid product were subjected to GC analysis. For the base trap solution, the HBr concentration was measured with an ion-selective electrode. Based on all of these measurements, carbon and bromine balances were calculated.

The experiment was continuously run for over 300 hours until the conversion of PhBr dropped from 100% in the initial 70 hrs to below 30% (FIG. 31). Hydrodebromination of PhBr took place over the catalyst bed with the formation of benzene ("BZ") and HBr as the major products, accompanied with some light hydrocarbons ($C_3$-$C_7$) being detected as byproducts, which originated from solvent decomposition. Carbon deposition was recognized as the primary reason for deactivation of the catalyst. The catalyst proved to be re-generable via decoking at 500° C. with $O_2$ oxidation (5 ml/min) for 10 hrs, followed by $H_2$ reduction (20 ml/min) at 400° C. for 3 hrs. The regenerated catalyst was identified to be as effective as the fresh catalyst, as confirmed by its ability to catalyze the same hydrodebromination reaction without activity loss in the first 70 hours (FIG. 32).

EXAMPLE 6

The gas flow rate inlet to the HBr absorption process is 700,000 $m^3$/h at a temperature of 50° C. and includes HBr and hydrocarbons. The molar concentration of HBr is more than 70% of the feed mixture. The gas is fed to an absorption column that is cooled externally with liquid recirculation through a heat exchanger. The liquid inlet to the absorption column is an aqueous HBr stream also at a temperature of 50° C. and has a flowrate of 7,600,000 kg/h, with the HBr concentration of 50% by weight. The liquid outlet stream from the HBr absorption column has a flow rate of 10,800,000 Kg/h with a HBr concentration of 65% by weight. The liquid outlet is then sent to the evaporation section where 3,200,000 kg/h of HBr is recovered by heating the liquid stream to a temperature of 120° C. The liquid outlet from the evaporator is returned to the absorption column. Two absorption columns are required in the exemplary embodiment, each with a diameter of 8 meters and a height of 8 meters. Packing material can be used in the column to improve the absorption process.

EXAMPLE 7

The gas flow rate inlet to the HBr absorption process is 700,000 m$^3$/h at a temperature of 100° C. and includes HBr and hydrocarbons. The molar concentration of HBr is more than 70% of the HBr and hydrocarbons feed mixture. A distillation scheme is used to separate HBr from hydrocarbons. The distillation system operates at a pressure between 10 atm and 30 atm. A first distillation column separates methane and $C_2$ from the rest of the components and requires 24 theoretical stages. The condenser duty for this column is 310 MMkcal/h and the condenser temperature is −35° C. The reboiler duty is 112 MMkcal/h and the reboiler temperature is −7° C. A second distillation column separates methane from $C_2$ and HBr. The bottoms stream consists of $C_2$ with a small amount of HBr. This column requires 18 theoretical stages. The third distillation column separates HBr from other components heavier than HBr. The distillate is HBr with more than 99% purity. This column requires 37 theoretical stages. The condenser duty for the column is 290 MMkcal/h and the condenser temperature is −9° C. The reboiler duty is 440 MMkcal·h and the reboiler temperature is −36° C. The fourth distillation column separates light gases from the rest of the components and requires 10 theoretical stages. The condenser duty for this column is 30 MMkcal/h and the condenser temperature is −28° C. The reboiler duty is 65 MMkcal/h and the reboiler temperature is 233° C.

EXAMPLE 8

The gas outlet from the coupling reactor has HBr weight fraction of 72%. This stream is cooled down to 29° C., and vapor-liquid flash separation is used to remove heavy hydrocarbons. The vapor outlet from the flash is at a pressure of 3 atm and a flow rate of 26870 m3/hr. The aq. HBr inlet to the absorption column has 52% HBr by weight and a flow rate if 339512 kg/hr. The concentrated HBr at the bottom of the absorption column has 65% HBr by weight and a flow rate of 471950 kg/hr. Eight stages are required for the absorption column. The concentrated HBr stream is sent to a stripper where the column with six stages operates at a pressure of 15 atm. The reboiler temperature is 187° C. Dehydrated HBr leaves the top of the stripping column with 99% HBr by weight with 1% water by weight and the bottoms stream of the stripper consists of Aq. HBr with 52% HBr by weight and is returned back to the absorption column.

EXAMPLE 9

Bromine Recovery Using Chilled Brine

The test setup consisted of three test vessels that were connected in series. The first contained liquid bromine at 15° C. and atmospheric pressure. The second contained a brine solution consisting of 100 ml of 24.7% by weight NaCl in water. The third vessel contained 30 ml of 4 M NaOH as a bromine trap to capture any bromine passing through the chilled brine vessel. A nitrogen carrier stream was introduced into the bottom of the bromine vessel at 10 sccm and allowed to bubble through the liquid bromine. The bromine partial pressure at this temperature was 0.18 atm. The nitrogen and bromine then passed in series to the bottom of the chilled brine and sodium hydroxide solutions in order to ensure proper gas to liquid contact.

Three tests were conducted using the test setup. The first test was conducted using a chilled brine at a temperature of −5° C. with a bromine flow for 3 hours. The second test used a chilled brine at −10° C. and was conducted for 2.5 hours. The results of the first two absorption tests are shown in Table 3. The last test measured the absorption characteristics of the system over time. This test measured the absorption amounts at six times over a 12 hour absorption run. The results of the 12 hour absorption test are shown in Table 4a. Bromine breakthrough to the NaOH trap increases with time on stream as shown in Table 4b. This is a result of saturating the brine solution with bromine, thereby, reducing the capture capacity of the chilled brine.

TABLE 3

$Br_2$ Recovery Using Chilled Brine

|  | $Br_2$ Absorbed (g/hr-L) | $Br_2$ Distribution (%) |
|---|---|---|
| Brine at −5° C. (Trapping for 3 hr) | | |
| Brine | 7.6 | 95.1 |
| NaOH | 0.4 | 4.9 |
| Br Balance (%) | | 94.5 |
| Brine at −10° C. (Trapping for 2.5 hr) | | |
| Brine | 7.9 | 98.5 |
| NaOH | 0.1 | 1.5 |
| Br Balance (%) | | 92.2 |

TABLE 4a

Average $Br_2$ Recovery Using Chilled Brine

|  | $Br_2$ Absorbed (g/hr-L) | $Br_2$ Distribution (%) |
|---|---|---|
| Brine at −5° C. (Trapping for 12 hr) | | |
| Brine | 7.8 | 88.1 |
| NaOH | 1.1 | 11.9 |
| Br Balance (%) | | 101.3 |

TABLE 4b

Time Dependence of Bromine Breakthrough in Base Trap

| Time | Bromine breakthrough Percentage in base Trap |
|---|---|
| 0-2 | 2.5 |
| 2-4 | 7.5 |
| 4-6 | 9.3 |
| 6-8 | 13.9 |
| 8-10 | 19.6 |
| 10-12 | 19.6 |

EXAMPLE 10

In this example, 0.5 g $SeO_2$ was loaded into two bubbler containers. A 3.06 ml 48 wt. % aqueous HBr solution (2.187 g HBr, 4.56 g soln.) was added in the first container, and a 4.08 ml of the same solution (2.917 g HBr, 6.08 g soln.) was added in the second container at room temperature. The samples were submerged in a preheated oil bath at 100° C. A 3 ml/min. oxygen stream was passed over the containers with the gas leaving the containers passed through 15 ml 4 M NaOH solution that captured all bromine vapors. The NaOH traps were changed every hour and the bromine content was determined by iodometric titration with standard 0.1000 M $Na_2S_2O_3$. The results are shown in Table 5 below.

TABLE 5

| Time, h | Sample 1 | Sample 2 | mol Br/hour(1) | mol Br/hour(2) | mmol $Br_2$/ml * min(1) | mmol $Br_2$/ml * min(2) |
|---|---|---|---|---|---|---|
| 1 | 7.6 | 6.97 | 0.00076 | 0.000697 | 0.002069717 | 0.001424 |
| 2 | 7.82 | 5.4 | 0.000782 | 0.00054 | 0.00212963 | 0.001103 |
| 3 | 4.35 | 2.78 | 0.000435 | 0.000278 | 0.001184641 | 0.000568 |
| 4 | 3.92 | 7 | 0.000392 | 0.0007 | 0.001067538 | 0.00143 |
| 5 | 4.3 | 5.5 | 0.00043 | 0.00055 | 0.001171024 | 0.001123 |
| 6 | 3.28 | 4.58 | 0.000328 | 0.000458 | 0.000893246 | 0.000935 |
| 7 | 3.7 | 5.09 | 0.00037 | 0.000509 | 0.001007625 | 0.00104 |

EXAMPLE 11

In this example, 1 g $SeO_2$ was loaded into two bubbler containers. A 3.06 ml, 62 wt. % aqueous HBr solution was added to the first one (2.915.6 g HBr, 4.7 g soln.), and 3.67 ml of the same solution to the second one (3.645 g HBr, 5.88 g soln.) at room temperature. The samples were submerged in a preheated oil bath at 100° C. A 3 ml/min. oxygen stream was passed over the containers with the gas leaving the containers passed through 15 ml 4 M NaOH solution that captured all bromine vapors. The NaOH traps were changed every hour and the bromine content was determined by iodometric titration with standard 0.1000 M $Na_2S_2O_3$. The results are shown in Table 6 below.

TABLE 6

| Time, h | Sample 1 | Sample 2 | mol Br/hour(1) | mol Br/hour(2) | mmol $Br_2$/ml * min(1) | mmol $Br_2$/ml * min(2) |
|---|---|---|---|---|---|---|
| 1 | 16.8 | 20 | 0.00168 | 0.002 | 0.004667 | 0.004505 |
| 2 | 16.24 | 17.58 | 0.001624 | 0.001758 | 0.004511 | 0.003959 |
| 3 | 12.65 | 15 | 0.001265 | 0.0015 | 0.003514 | 0.003378 |
| 5 | 15.89 | 16.7 | 0.001589 | 0.00167 | 0.004414 | 0.003761 |

EXAMPLE 12

In this example, 1 g $SeO_2$ was loaded into two bubbler containers. A 5.12 ml, 68 wt. % aqueous HBr solution was added to the first one (5.83 g HBr, 8.81 g soln.), and 7.16 ml of the same solution to the second one (7.29 g HBr, 12.60 g soln.) at room temperature. The samples were submerged in preheated oil bath at 100° C. A 3 ml/min. oxygen stream was passed over the containers with the gas leaving the containers passed through 15 ml 4 M NaOH solution that captured all bromine vapors. The NaOH traps were changed every hour and the bromine content determined by iodometric titration with standard 0.1000 M $Na_2S_2O_3$. The results are shown in Table 7 below.

TABLE 7

| Time, h | Sample 1 | Sample 2 | mol Br/hour(1) | mol Br/hour(2) | mmol $Br_2$/ml * min(1) | mmol $Br_2$/ml * min(2) |
|---|---|---|---|---|---|---|
| 1 | 45.6 | 53.63 | 0.00456 | 0.005363 | 0.0076 | 0.006242 |
| 2 | 28.05 | 55.9 | 0.002805 | 0.00559 | 0.004675 | 0.006506 |
| 3 | 16.13 | 33.2 | 0.001613 | 0.00332 | 0.002688 | 0.003864 |
| 4 | 15.2 | 22.31 | 0.00152 | 0.002231 | 0.002533 | 0.002597 |

EXAMPLE 13

In this example, 1 g $SeO_2$ was loaded in a bubbler container. A 5 ml, 68 wt. % aqueous HI solution was added to the bubbler container (5.83 g HI, 8.81 g soln.) at room temperature. The sample was submerged in preheated oil bath at 100° C. A 3 ml/min. oxygen stream was passed over the container with the gas leaving the container passed through 15 ml 4 M NaOH solution that captured all iodine vapors. The NaOH traps were changed every hour and the iodine content determined by titration with standard 0.1000 M $Na_2S_2O_3$.

EXAMPLE 14

In this example, three samples of 20 grams of H-exchanged zeolite was refluxed at 100° C. with 300 mL 0.1 M, 1 M and saturated $H_2C_2O_4$ (~1.15 M) correspondingly for 2 hours. The zeolite was filtered, washed and dried slowly. The resulted ZSM-5 modified materials were exchanged with 0.1 M $Mn(NO_3)_2$ for at least eight hours, filtered, washed and dried. The three samples were tested for coupling of methyl bromide at 425° C. with a residence time of 3 seconds. The data is summarized in Table 8 shown below.

TABLE 8

| Catalyst | Benzene/BTX, % | BTX, % | Coke, % | C-Bal. % | $[H_2C_2O_4]$, mol/l |
|---|---|---|---|---|---|
| Mn3024_0 De-Al | 19.1 | 39.4 | 5.4 | 97.9 | N/A |
| Mn3024_1 De-Al | 25.5 | 42.4 | 5.4 | 94.7 | 0.1 |
| Mn3024_2 De-Al | 26.7 | 41.5 | 5.2 | 94.6 | 1.0 |
| Mn3024_3 | 30.8 | 40.8 | 6.5 | 93.6 | 1.15 |

EXAMPLE 15

In this example, the effect of water vapors on the catalytic conversion of methyl bromide conversion to BTX products using conditions typical for a BTX process (425° C., 0.5 atm. methyl bromide partial pressure, 5 s residence time) were examined. The results are summarized below in Table 9, showing the trend of the coke generated as a function of water added. It is important to note that the products distribution is relatively unchanged by the water addition to the reaction mixture.

TABLE 9

| | T Bubbler (° C.) | | | | | |
|---|---|---|---|---|---|---|
| | None | 0 | 10 | 19 | 36 | 58 |
| % $H_2O$ | 0.0 | 0.3 | 0.6 | 1.0 | 2.9 | 8.3 |
| % C Bal | 100 | 98.2 | 103.4 | 100.1 | 107.5 | 105.9 |
| % MeBr Conv. | 99.0 | 99.3 | 99.4 | 99.2 | 99.3 | 99.2 |

TABLE 9-continued

| | T Bubbler (° C.) | | | | | |
|---|---|---|---|---|---|---|
| | None | 0 | 10 | 19 | 36 | 58 |
| % Coke | 7.4 | 6.7 | 5.5 | 6.3 | 4.8 | 4.5 |
| % BTX | 35.8 | 36.6 | 34.8 | 34.3 | 32.8 | 32.2 |
| % B/BTX | 19.6 | 21.3 | 20.8 | 19.0 | 18.4 | 16.1 |
| % C2-C6 | 41.5 | 42.3 | 45.3 | 45.1 | 49.8 | 50.4 |
| % MDN+ | 13.5 | 13.2 | 13.4 | 13.0 | 11.4 | 11.5 |

EXAMPLE 16

In this example, a modified ZSM-5 catalyst was used to produce mesitylene from methylbromide. 1.0 gram of 7% CuO/0.5% ZnO impregnated ZSM-5 catalyst was loaded into a test cell with operating conditions as follows: a reaction temperature of 400° C., a reaction time of 1 hour, a residence time of 0.8 sec, a flow rate of MeBr vapor of 12.28 sccm, and a total gas flow rate of 25 sccm. The main aromatic products were mesitylene, 49.3 wt %, and xylene, 23.1 wt %. Benzene production was suppressed: 2.5 wt %.

EXAMPLE 17

Catalyst Preparation of SAPO-34 Based Catalysts

A solution of 12.6 g of 85% phosphoric acid, 1.6 g of 37% HCl and 20.3 g of de-ionized water was added to 27.2 of aluminum isopropoxide in a PE bottle. The bottle was shaken for 1 min, after which 4.0 g of Ludox SM-30 (manufacturer) colloidal silica was added, and the bottle was shaken again for 1 min. Then 56.2 g 35% TEAOH (tetraethylamine hydroxide) and 9.1 g water were added and the bottle was shaken for 1 min. The mixture was then transferred to a Teflon-lined autoclave, and left for 48 h under constant agitation at room temperature. The composition of the resulting gel, expressed in terms of the molar ratios, was TEAOH:$Al_2O_3$:0.89 $P_2O_5$: 0.3 $SiO_2$:0.2 HCl:64$H_2O$. The temperature was then increased to 215° C., and the mixture was heated for 100 h at this temperature. After washing the precipitate with de-ionized water followed by drying at 120° C. and calcination at 600° C. for 6 h, a powder sample was obtained. The pure SAPO-34 phase (CHA) was identified from XRD measurements. Partial framework substitution with metals such as Co, Ni, Fe, Mn or Ga was conducted by mixing the individual nitrate salt into the starting mixture solution with a molar ratio of metal/$Al_2O_3$~0.02.

EXAMPLE 18

Catalyst Preparation of ZSM-5 Based Catalysts

Commercially available HZSM-5 materials with different $SiO_2$/$Al_2O_3$ ratios purchased from ZEOLYST International were used as the initial materials in this work. A representative example is CBV 8014, abbreviated here as 8014. 8014 is an H-exchanged type ZSM-5 with a $SiO_2/Al_2O_3$ ratio of 80. The materials were modified by loading various metals via wet impregnation starting from their salt solutions. The doped or exchanged metals involves Mg, Ca, Sr, Ba, K, Ag, P, La, or Zn and the loading amounts varied in the range of 0.1 to 10% by weight. The metal doped catalysts were further activated by calcination in the temperature range of 500 to 800° C. for 6 h prior to use. XRD patterns for the initial material and the ones with metal doped were obtained to verify the compositions. The loading of Mg or Ca slightly affected the peak strengths but did not change the zeolite structures.

EXAMPLE 19

Some non ZSM-5 and non SAPO-34 materials such as ferrierite structure zeolite and a aluminophosphate (AlPO-5) can also be applied in the conversion of $CH_3Br$ to light olefin. These materials are either commercial available or were synthesized in our lab. AlPO-5 was synthesized following the procedure described in IZA website with small modifications. The synthesis procedure is as follows.

(1) Mix 7 g water with 3.84 g 85% phosphoric acid
(2) Add 2.07 g triethylamine (TEA) drop wise to (1)
(3) Add 5.23 g aluminum isopropoxide to (2) in small amounts at 0° C. with intense stirring then stir the mixture at room temperature for 2 h
(4) Add 0.83 g 40% HF (in water) and 89.2 g water to (3), stir for 2 h
(5) Hydrothermal synthesis at 180° C. (preheated oven) for 23 h
(6) Wash the precipitate with DI water
(7) Dry the precipitate at 120° C. for 10 h
(8) Calcine the powder at 600° C. for 6 h The XRD measurement confirmed that a pure AFI phase that belongs to AlPO-5 was obtained.

EXAMPLE 20

High Ethylene Mode

High light olefin yields as well as high ethylene/propylene ratios can be achieved by using narrow pore zeolite materials and conducting the reactions at elevated temperature. Two typical results were obtained over SAPO-34 or CoSAPO-34 at 500° C. with 2.0 sec residence time and 0.2 atm. partial pressure of $CH_3Br$. The $CH_3Br$ conversion, combined $C_2+C_3$ yield (C base), combined ethylene+propylene yield (C base) and ethylene/propylene (weight ratio.) reached 91.4%, 61.9%, 58.7% and 1.7 for SAPO-34 with 8.1% coke formation (C base) and 97.9%, 65.6%, 60.2%, 1.7 for CoSAPO-34 with 11.7% coke.

A typical product selectivity and C mole yield for different products obtained from SAPO-34 at 500° C., 0.2 sec and 0.2 atm $CH_3Br$ are shown in Table 10.

TABLE 10

CH3Br Coupling over SAPO-34 at 500° C., 0.2 sec and 0.2 atm CH₃Br Catalyst, SAPO-34
Condition, 500° C., 0.2 sec, 0.2 atm CH₃Br

| C mol Selectivity, % | | C mol Breakdown, % | |
|---|---|---|---|
| $CH_4$ | 8.2 | | |
| $C_2H_4$ | 40.2 | | |
| $C_2H_6$ | 1.0 | | |
| $C_3H_6$ | 24.1 | $C_2^= + C_3^=$ | 58.7 |
| $C_3H_8$ | 2.4 | other $C_1$-$C_6$ | 16.5 |

TABLE 10-continued

CH3Br Coupling over SAPO-34 at 500° C., 0.2 sec and 0.2 atm CH₃Br Catalyst, SAPO-34
Condition, 500° C., 0.2 sec, 0.2 atm CH₃Br

| C mol Selectivity, % | | C mol Breakdown, % | |
|---|---|---|---|
| $C_{4-6}$ | 6.5 | BTXM+ | 3.4 |
| BTXM+ | 3.7 | $CH_3Br$ | 8.6 |
| RBr | 5.1 | RBr | 4.7 |
| Coke | 8.9 | coke | 8.1 |

$CH_3Br$ conversion, % 91.4
$C_2^=/C_3^=$ (wt) 1.67
C Balance, % 100.3

EXAMPLE 20

High Propylene Mode

High combined light olefin yield and high propylene selectivity was obtained from ZSM-5 based catalyst at relative lower temperature, 400° C. and short residence time, <1 sec. The catalysts modified by loading alkaline earth metals (e.g. Mg, Ca, Sr or Ba) show excellent performance.

Using a ZSM-5 based catalyst with 5% Mg loading, 5% Mg/8014-750, 98.3% $CH_3Br$ conversion, 54.3% LO yield with ethylene/propylene weight ratio 0.10 were achieved at 400° C. with 0.5 sec residence time and 0.1 atm $CH_3Br$. Much lower coke formation (0.6%) was measured compared with SAPO-34 based materials. The catalyst also showed excellent reproducibility during the test of over 20 cycles. The product selectivity and C mole yield for different products obtained using this catalyst are shown in Table 11.

TABLE 11

CH₃Br Coupling over 5% Mg/8014-750 at 400° C., 0.5 sec and 0.1 atm. CH₃Br
Catalyst, 5% Mg/8014-750
Condition, 400° C., 0.5 sec, 0.1 atm CH₃Br

| C mol Selectivity, % | | C mol Breakdown, % | |
|---|---|---|---|
| $CH_4$ | 0.0 | | |
| $C_2H_4$ | 4.8 | | |
| $C_2H_6$ | 0.0 | | |
| $C_3H_6$ | 50.5 | $C_2^= + C_3^=$ | 54.3 |
| $C_3H_8$ | 0.0 | other $C_1$-$C_6$ | 16.5 |
| $C_{4-6}$ | 29.3 | BTXM+ | 3.4 |
| BTXM+ | 7.7 | $CH_3Br$ | 1.8 |
| RBr | 6.9 | RBr | 6.8 |
| Coke | 0.6 | coke | 0.6 |

$CH_3Br$ conversion, % 98.3
$C_2^=/C_3^=$ (wt) 0.1
C Balance, % 92.1

EXAMPLE 21

Moderate Ethylene Mode

High light olefin yield, >50%, flexible ethylene and propylene fractions (ethylene/propylene weight ratio, 0.3 to 1.3) can be achieved either by using SAPO-34 and ZSM-5 based catalysts independently at a wide temperature condition or by using the two types of materials sequentially. Initially, the feed was allowed to contact SAPO-34, where high ethylene/propylene ratio and incomplete $CH_3Br$ conversion (70-80%) were achieved, and then let the product gasses pass through the second catalyst bed where highly active ZSM-5 based catalyst was loaded, which substantially consumed all unconverted $CH_3Br$ and produce more propylene than ethylene as a compromise. As a results, a high $CH_3Br$ conversion and acceptable ethylene/propylene fraction can be achieved from this mixed catalyst system. It is expected that this combinational method still has large room for further improvement through optimizing the conditions for the two catalyst beds.

From a sequential mixed catalyst system SAPO-34 B+5% Sr/8014-750, the $CH_3Br$ conversion, light olefin yield and ethylene/propylene ratios reached 93.3%, 51.7% and 0.7 respectively at 475° C., with 2.1 sec residence time (2.0 sec over SAPO 34-B and 0.1 sec over 5% Sr/8014-750) and 0.2 atm $CH_3Br$.

One typical result obtained from SAPO-34 B+5% Sr/ZSM-5 are shown in Table 12.

TABLE 12

$CH_3Br$ Coupling over SAPO-34B + 5% Sr/8014-750 at 475° C., 2.1 sec and 0.2 atm. $CH_3Br$
Catalyst, SAPO-34B + 5% Sr/8014-750
Condition, 475° C., 2.1 sec, 0.2 atm $CH_3Br$

| C mol Selectivity, % | | C mol Breakdown, % | |
|---|---|---|---|
| $CH_4$ | 7.3 | | |
| $C_2H_4$ | 22.8 | | |
| $C_2H_6$ | 0.7 | | |
| $C_3H_6$ | 32.1 | $C_2^- + C_3^-$ | 51.3 |
| $C_3H_8$ | 3.0 | other $C_1$-$C_6$ | 20.4 |
| $C_{4-6}$ | 10.7 | BTXM+ | 8.6 |
| BTXM+ | 9.2 | $CH_3Br$ | 6.6 |
| RBr | 6.3 | RBr | 5.9 |
| Coke | 7.8 | coke | 7.3 |

$CH_3Br$ conversion, % 93.3
$C_2^-/C_3^-$ (wt) 0.71
C Balance, % 100.9

Table 13 summarizes more results on the three operation modes.

TABLE 13

Summary of the Results for Three Modes of Operation: (1) High ethylene, (2) High Propylene, and (3) Moderate Ethylene

| Mode | Catalyst | Temp/C. | (sec)$^\tau$ | P$CH_3Br$ | Conv. % | LO Yield, % | $C_2^-/C_3^-$ (wt) | Coke, % | C-Balance, % |
|---|---|---|---|---|---|---|---|---|---|
| High $C_2^-$ | SAPO-34 | 500 | 2.0 | 0.2 | 91.4 | 58.7 | 1.7 | 8.1 | 100.3 |
|  | CoSAPO-34 | 500 | 2.0 | 0.2 | 97.9 | 60.2 | 1.7 | 11.7 | 100.4 |
| High $C_3^-$ | 5% Mg/ZSM-5 | 400 | 0.5 | 0.1 | 98.3 | 54.2 | 0.1 | 0.6 | 95.6 |
| Moderate $C_2^-$ | SAPO-34 | 475 | 2.0 | 0.2 | 88.1 | 54.2 | 1.3 | 7.6 | 99.9 |
|  | Co-SAPO-34 | 450 | 2.0 | 0.2 | 96.2 | 50.6 | 1.0 | 10.8 | 98.3 |
|  | CoSAPO-34 | 475 | 2.0 | 0.2 | 96.8 | 58.4 | 1.3 | 9.9 | 99.8 |
|  | Mixed Catalyst* | 475 | 2.1 | 0.2 | 93.3 | 51.7 | 0.7 | 7.3 | 100.9 |

*SAPO-34-B + 5% Sr/8014-750 (1.55 g + 0.1 g)

EXAMPLE 22

Ferrierite

A non ZSM-5, non-SAPO-34 materials, with 2-dimensional and 10-ring ferrierite structure was tested under the conditions for coupling reactions. A commercial available ferrierite, CP914 (Zeolyst) with $SiO_2/Al_2O_3$ ratio of 55 was tested at 475° C., 0.2 atm $CH_3Br$ with a residence time 15 of 1.0 sec. The catalyst exhibited moderate activity towards the reaction and moderate ethylene selectivity. The $CH_3Br$ conversion, light olefin yield and ethylene/propylene ratio reached 49.8%, 14.8% and 0.89% respectively. The results are shown in Table 14.

TABLE 14

$CH_3Br$ Coupling over Ferrierite at 475° C., 1.0 sec and 0.2 atm. $CH_3Br$ Catalyst, ferrierite (CP914)
Condition, 475° C., 1.0 sec, 0.2 atm $CH_3Br$

| C mol Selectivity, % | | C mol Breakdown, % | |
|---|---|---|---|
| $CH_4$ | 10.9 | | |
| $C_2H_4$ | 13.9 | | |
| $C_2H_6$ | 1.1 | | |
| $C_3H_6$ | 15.8 | $C_2^- + C_3^-$ | 14.8 |
| $C_3H_8$ | 3.4 | other $C_1$-$C_6$ | 18.0 |
| $C_{4-6}$ | 20.7 | BTXM+ | 3.9 |
| BTXM+ | 7.9 | $CH_3Br$ | 50.2 |
| RBr | 14.9 | RBr | 7.4 |
| Coke | 11.4 | coke | 5.7 |

$CH_3Br$ conversion, % 49.8
$C_2^-/C_3^-$ (wt) 0.89
C Balance, % 99.9

EXAMPLE 23

AlPO-5

Another non-ZSM-5 and non-SAPO-34 type zeolite, AlPO-5 was synthesized in the lab following a procedure described on IZA website. XRD measurement confirmed the existence of one dimensional AFI structure in our sample. The coupling reaction was conducted at 400° C., 0.2 atm $CH_3Br$ with a residence time of 2 sec. The catalyst gave 8.8% $CH_3Br$ conversion with light olefin yield of 1.2% and ethylene/propylene weight ratio of 0.62. The results are shown in Table 15.

TABLE 15

$CH_3Br$ Coupling over AlPO-5 at 400° C., 2.0 sec and 0.2 atm $CH_3Br$ Catalyst, C-H-5
Condition, 400° C., 2 sec, 0.2 atm $CH_3Br$

| C mol Selectivity, % | | C mol Breakdown, % | |
|---|---|---|---|
| $CH_4$ | 13.7 | | |
| $C_2H_4$ | 7.9 | | |
| $C_2H_6$ | 0.0 | | |
| $C_3H_6$ | 12.8 | $C_2^- + C_3^-$ | 1.2 |
| $C_3H_8$ | 0.0 | other $C_1$-$C_6$ | 1.1 |
| $C_{4-6}$ | 5.9 | BTXM+ | 0.9 |
| BTXM+ | 15.4 | $CH_3Br$ | 94.3 |

TABLE 15-continued

CH$_3$Br Coupling over AlPO-5 at 400° C., 2.0 sec and
0.2 atm CH$_3$Br Catalyst, C-H-5
Condition, 400° C., 2 sec, 0.2 atm CH$_3$Br

| C mol Selectivity, % | | C mol Breakdown, % | |
|---|---|---|---|
| RBr | 1.2 | RBr | 0.1 |
| Coke | 43.0 | coke | 2.5 |

CH$_3$Br conversion, % 8.8
C$_2^-$/C$_3^-$ (wt) 0.62
C Balance, % 96.8

EXAMPLE 24

Effect of Reaction Temperature Over SAPO-34

Figure 33:
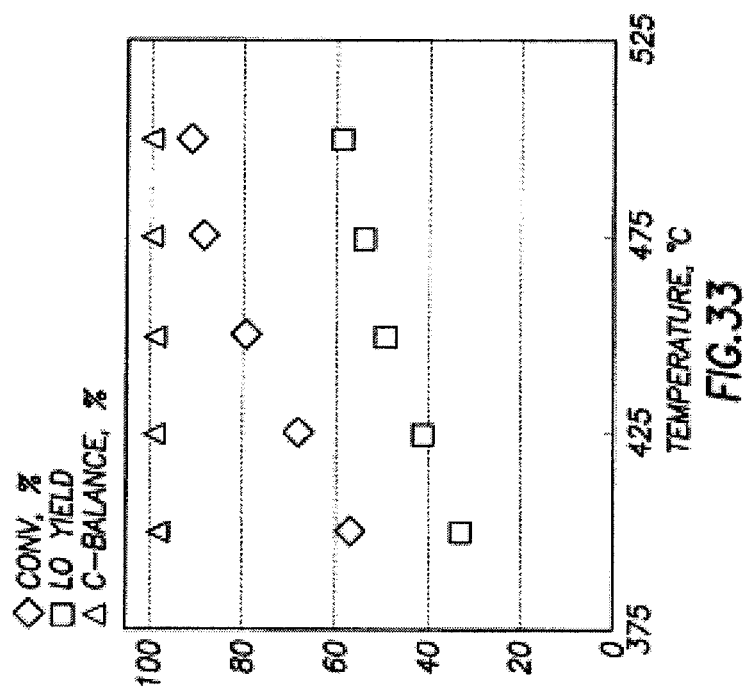
FIG. 33 is a graph of methyl bromide coupling results as a function of temperature, for an experiment conducted according to one embodiment of the invention.

The coupling of bromomethane was conducted over SAPO-34 in a temperature range from 400 to 500° C. It was found that high temperature favors the formation of ethylene and propylene. It was observed that increasing the reaction temperature significantly enhanced CH$_3$Br conversion, light olefin yield and the ethylene/propylene weight ratio. Coke amount also increased from 4.0% at 400° C. to 8.1% at 500° C. At the temperature higher than 475° C., CH$_3$Br conversion exceeded 88%, light olefin yield reached 55% or higher and the ethylene/propylene weight ratios were higher than 1. Examining the product selectivity, it was found that high temperature may promote C$_4$ decomposition, suppresses C$_3$H$_8$ and RBr formation and as a result, produces more ethylene and methane while with less C4 product formation. The results are shown in FIG. 33 and Table 16.

TABLE 16

Effect of Reaction Temperature on Product Selectivity over SAPO-34
Catalyst, SAPO-34
Condition, 2.0 sec, 0.2 atm CH$_3$Br

| | C mol Selectivity, % | | | | |
|---|---|---|---|---|---|
| | 400° C. | 425° C. | 450° C. | 475° C. | 500° C. |
| CH$_4$ | 1.3 | 2.1 | 3.2 | 4.8 | 8.2 |
| C$_2$H$_4$ | 19.4 | 24.3 | 29.7 | 34.4 | 40.2 |
| C$_2$H$_6$ | 0.3 | 0.4 | 0.6 | 0.8 | 1.0 |
| C$_3$H$_6$ | 39.3 | 35.9 | 32.5 | 27.1 | 24.1 |
| C$_3$H$_8$ | 7.0 | 5.2 | 4.8 | 3.6 | 2.4 |
| C$_{4-6}$ | 14.0 | 13.3 | 10.4 | 9.6 | 6.5 |
| BTXM+ | 2.8 | 4.4 | 3.7 | 3.1 | 3.7 |
| RBr | 8.9 | 9.1 | 9.2 | 7.9 | 5.1 |
| Coke | 7.0 | 5.3 | 5.9 | 8.6 | 8.9 |

EXAMPLE 25

Catalyst Stability and Reproducibility

Figure 34:
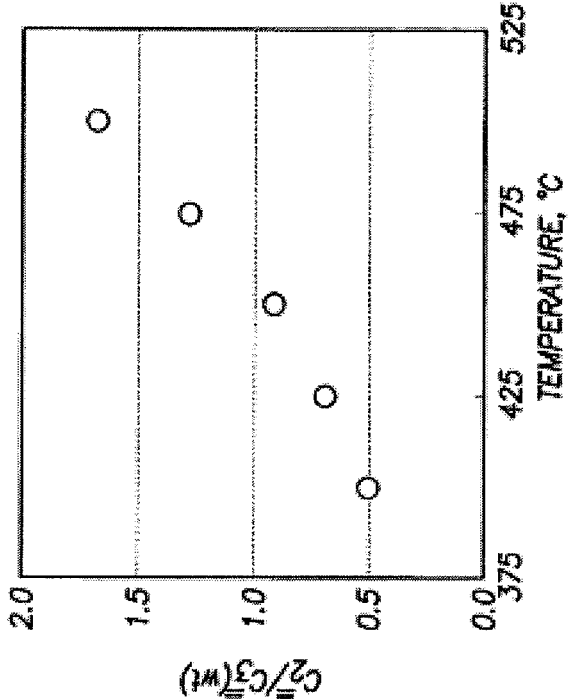
FIG. 34 is another graph of methyl bromide coupling results as a function of temperature, for an experiment conducted according to one embodiment of the invention.

The stability of the catalyst system for at least 10 cycles including reactions has been demonstrated with SAPO-34 catalyst. Reactions were run at 475° C. with 0.2 sec residence time and 0.2 atm. partial pressure CH$_3$Br. Catalyst regeneration (decoking) was done at 500° C. overnight with 5 sccm air. The catalyst showed excellent stability and reproducibility in terms of CH$_3$Br conversions, light olefin yields, ethylene/propylene ratios, coke amounts etc. The results, as a function of cycle number, are displayed in FIG. 34. No noticeable catalyst decay was observed under these conditions and no structure changes were observed in XRD measurements.

EXAMPLE 26

Effect of Residence Time on Product Distribution Over 5% Mg/8014

Figure 35:
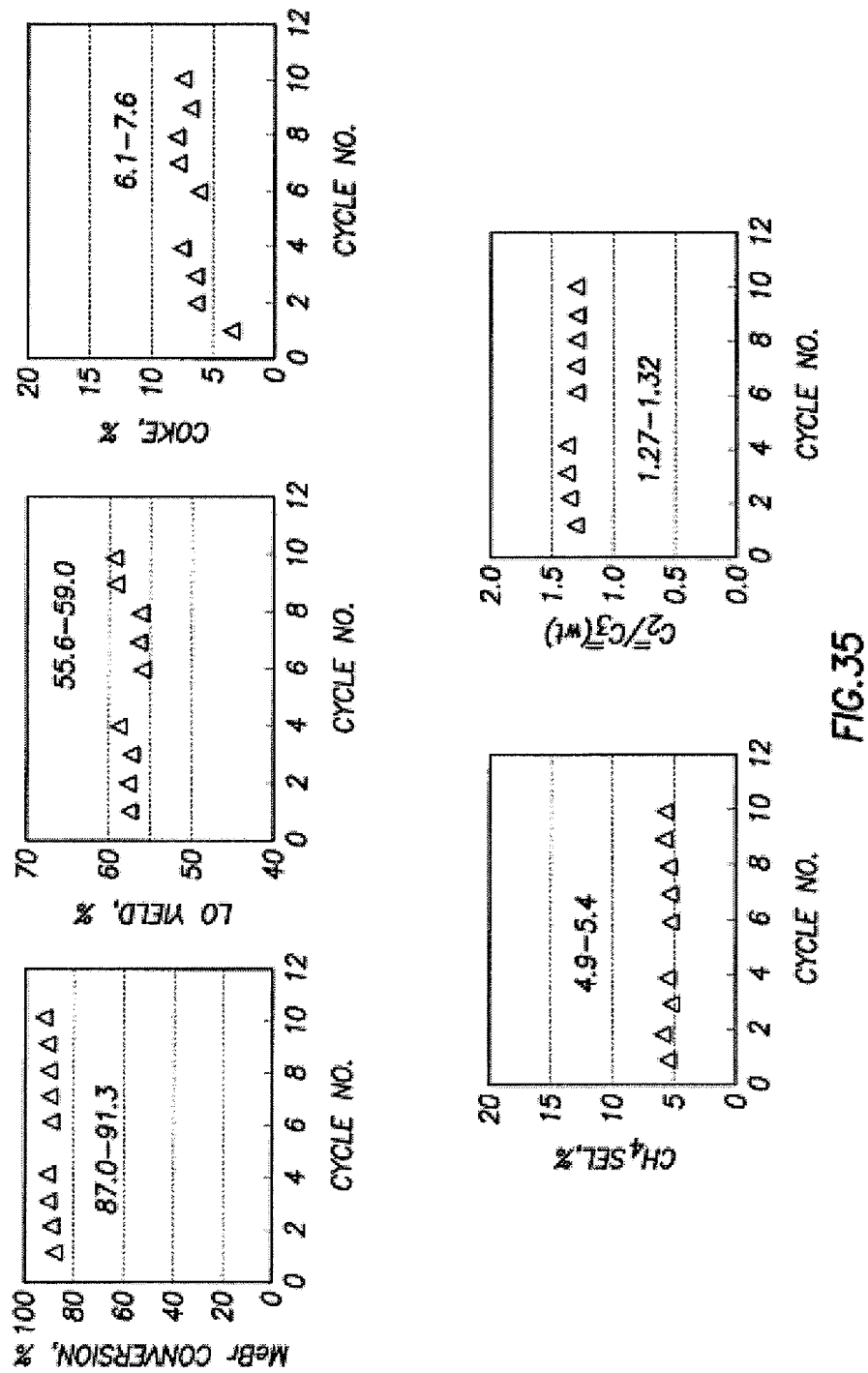
FIG. 35 is a graph of methane selectivity as a function of cycle number, for an experiment conducted according to one embodiment of the invention.

Using the catalyst of 5% Mg/8014 we investigated the effect of residence time by changing the residence time from 0.1 sec to 5 sec. The data, displayed in FIG. 35 show that short residence time (<1 sec) favors the formation of light olefin while longer residence time lead to more BTX and light alkanes (propane and butanes), which contribute to the major component of "other C$_1$-C$_6$."

EXAMPLE 27

Methanol to Light Olefin Comparison

Methanol coupling to light olefin (MTO) experiments were also conducted with two GRT catalysts, 5% Mg/8014, and 5% Ca/8014 and a commercially available MTO catalyst (Grace Davison olefin Oultra). Reactions were run at 400° C., 0.1 atm. partial pressure MeOH and a residence time of 0.5 sec. The results are summarized in Table 17. The GRT catalysts have higher combined ethylene+propylene yield.

TABLE 17

Comparison of GRT catalysts and Grace Davison C.A.O.C
for Conversion of MeOH to Light Olefins at 400° C., 0.1 atm.
MeOH and 0.5 sec

| Catalyst | Utilization | C$_2^-$ + C$_3^-$ | C$_2^-$/C$_2$ | C$_3^-$/C$_3$ |
|---|---|---|---|---|
| 5% Mg/8014 | 93% | 47% (7/40) | 100% | 97% |
| 5% Ca/8014 | 87% | 51% (3/48) | 100% | 100% |
| Olefin Oultra | 95% | 37% (12/25) | 100% | 85% |

EXAMPLE 28

Figure 36:
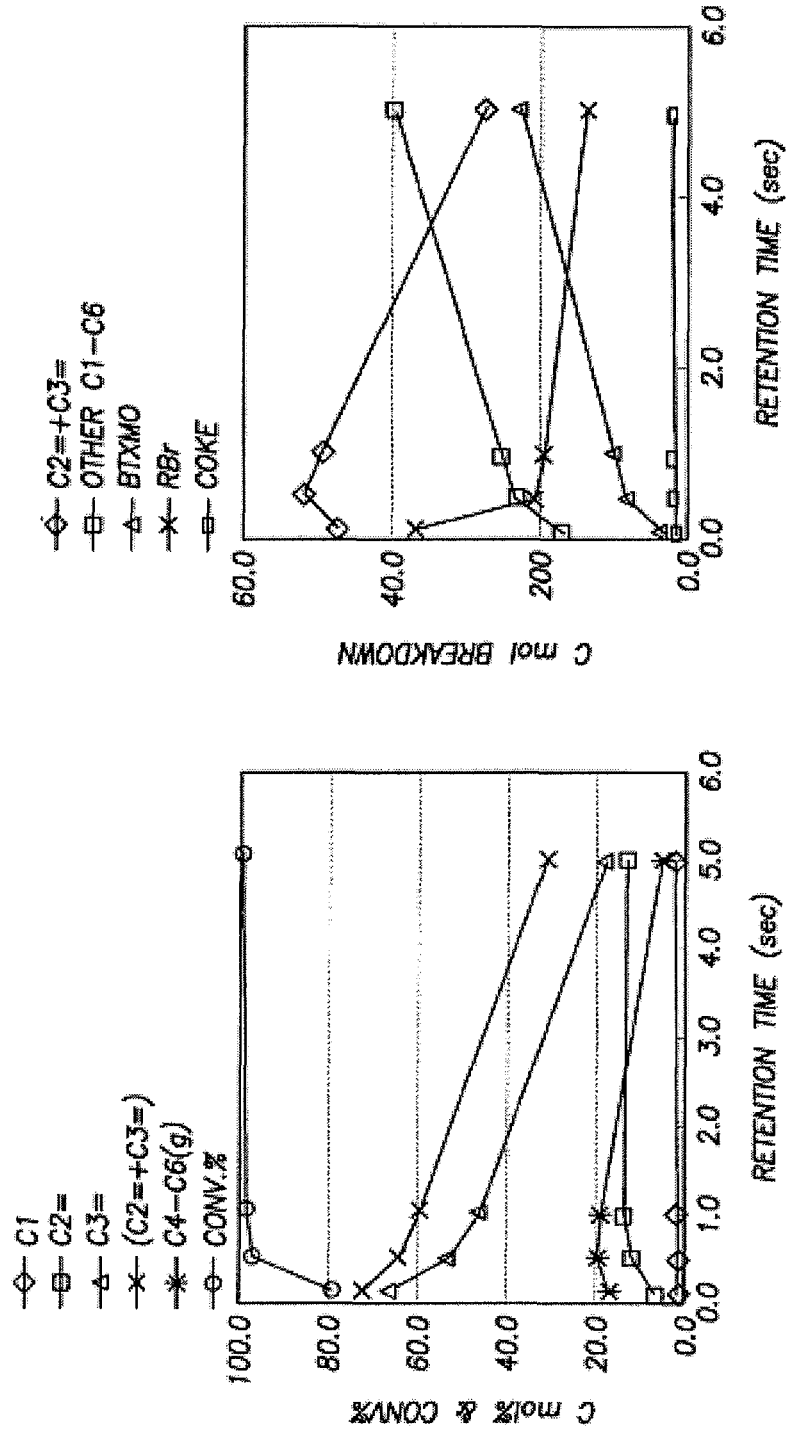
FIG. 36 is a graph of conversion efficiency as a function of retention time, for an experiment conducted according to one embodiment of the invention.
Figure 37:
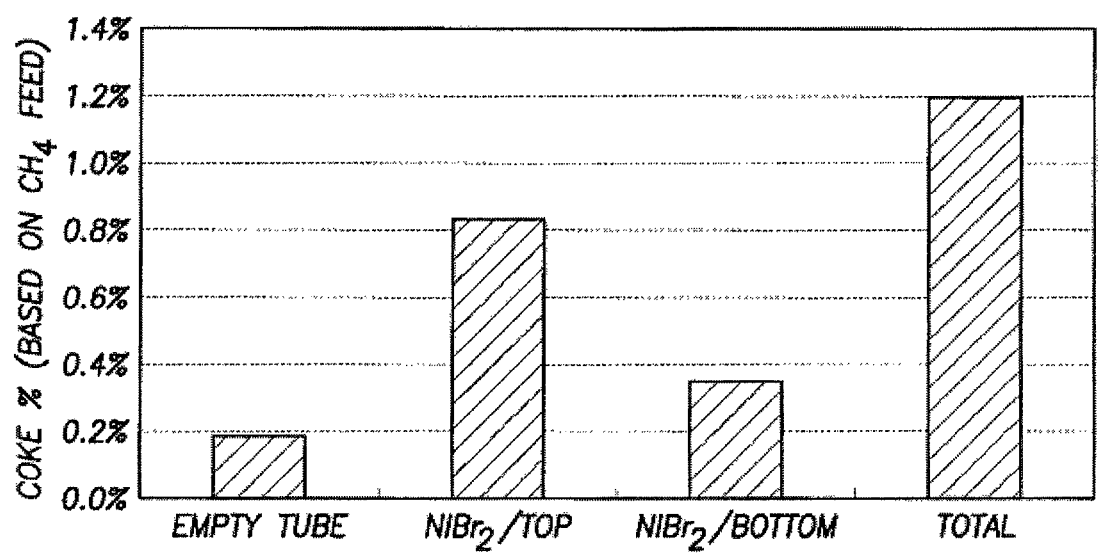
FIG. 37 is a graph of coke production, for an experiment conducted according to one embodiment of the invention.

In order to demonstrate the above expected results, a lab scale setup was used for bromination reaction. Typical bromination reaction conditions of about 500° C., 60 sec residence time, 70% CH$_4$ conversion, 1.5 sccm O$_2$ was run for about 2 hours. The product gasses passed through the Ba(OH)$_2$ solution to precipitate CO$_2$ generated during bromination. After the first reaction cycle, the inlet portion of the reactor appears clean, while the portion disposed downstream of the NiBr$_2$ bed appears to have accumulated coke. The coke deposited downstream of NiBr$_2$ was decoked in the second cycle by switching feed directions. Here the coke from the bottom portion (the downstream portion in the first run) was collected after removal of the NiBr$_2$ from the reactor. The measurements of the amount of coke are shown in FIG. 36. The results indicate that most of the coke oxidized in the first cycle during bromination. The total coke measured in this configuration appears to be greater than an empty tube bromination (based case), which may be due to CH$_2$Br$_2$ conversion into CO$_2$ during bromination in the presence of oxygen.

The invention has been described with references to various examples and preferred embodiments, but is not limited thereto. Other modifications and equivalent arrangements, apparent to a skilled person upon consideration of this disclosure, are also included within the scope of the invention. With reference to FIG. 1 and FIG. 2, in an alternate embodiment of the invention, the products 25 from the bromine generation reactor are fed directly into the bromination reactor 3. The advantage of such a configuration is in eliminating the bromine holdup needed in the flash unit 27, thereby reducing the handling of liquid bromine. Also, by eliminating the bromine scavenging section including units 26, 27, 31 and 34, the capital cost for the process can be reduced significantly. For energy efficiency, it is desirable to have the outlet of bromine generation be equal to the bromination temperature. For bromine generation, cerium-based catalysts are therefore preferred over copper-based catalysts in this embodiment, since cerium bromide has a higher melting point (722° C.) than copper (I) bromide (504° C.). The presence of oxygen in bromination and coupling reduces the selectivity to the desired products; therefore, the bromine generation reactor must consume all of the oxygen in the feed. In this embodiment, the monobromide separation 5 must be modified to remove water using a liquid-liquid split on the bottoms stream of the distillation column 51. The water removed in the liquid-liquid split contains HBr, which can be removed from water using extractive distillation (see, e.g., FIG. 9), and then recycled back to the bromine generation section.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A method comprising:
providing a halogen stream;
providing a first alkane stream;
reacting at least a portion of the halogen stream with at least a portion of the first alkane stream to form a halogenated stream, wherein the halogenated stream comprises alkyl monohalides, alkyl polyhalides, and hydrogen halide; and
contacting at least some of the alkyl monohalides with a coupling catalyst comprising a ZSM-5 zeolite having undergone a dealumination treatment to form a product stream that comprises higher hydrocarbons and hydrogen halide.

2. The method of claim 1 further comprising:
providing a second alkane stream;
reacting at least a portion of the second alkane stream with at least a portion of the alkyl polyhalides to create at least some additional alkyl monohalides; and
contacting at least some of the additional alkyl monohalides with the coupling catalyst to form at least some higher hydrocarbons and hydrogen halide.

3. The method of claim 1 further comprising:
separating the hydrogen halide from the product stream; and
reacting the hydrogen halide with a source of oxygen to regenerate the halogen stream.

4. The method of claim 1 wherein the coupling catalyst comprises a plurality of catalytic materials wherein each catalytic material is disposed in a different reaction vessel.

5. The method of claim 1 further comprising:
providing a Lewis base molecule; and
contacting the Lewis base molecule with the coupling catalyst contemporaneously with the contacting of at least some of the alkyl monohalides with the coupling catalyst to form the product stream.

6. The method of claim 5 wherein the Lewis base molecule is present in an amount less than about 15% by weight of the total feed to the coupling catalyst.

7. The method of claim 1 wherein the dealumination treatment comprises contacting the coupling catalyst with a dealumination agent.

8. The method of claim 7 wherein the dealumination agent comprises at least one material selected from the group consisting of: a mineral acid, hydrochloric acid, hydrofluoric acid, a chelating agent, ethylenediaminetetraacetic acid, oxalic acid, malonic acid; steam, an exchange reagent, $SiCl_4$, $NH_4[SiF_6]$, $NH_4HF_2$, $AlF_3$, a trialkyl phosphate, an organic phosphite, and a combination thereof.

* * * * *